US009157083B2

(12) United States Patent
Bhat et al.

(10) Patent No.: US 9,157,083 B2
(45) Date of Patent: Oct. 13, 2015

(54) MICRORNA COMPOUNDS AND METHODS FOR MODULATING MIR-122

(71) Applicant: REGULUS THERAPEUTICS INC., San Diego, CA (US)

(72) Inventors: Balkrishen Bhat, San Diego, CA (US); Daniel Hogan, San Diego, CA (US)

(73) Assignee: Regulus Therapeutics Inc., San Diego, CA (US)

( * ) Notice: Subject to any disclaimer, the term of this patent is extended or adjusted under 35 U.S.C. 154(b) by 0 days.

(21) Appl. No.: 14/577,481

(22) Filed: Dec. 19, 2014

(65) Prior Publication Data

US 2015/0105449 A1 Apr. 16, 2015

Related U.S. Application Data

(63) Continuation of application No. 14/266,136, filed on Apr. 30, 2014.

(60) Provisional application No. 61/822,112, filed on May 10, 2013, provisional application No. 61/839,550, filed on Jun. 26, 2013, provisional application No. 61/895,784, filed on Oct. 25, 2013, provisional application No. 61/898,704, filed on Nov. 1, 2013, provisional application No. 61/927,897, filed on Jan. 15, 2014, provisional application No. 61/818,432, filed on May 1, 2013.

(51) Int. Cl.

| | |
|---|---|
| ***C12N 15/11*** | (2006.01) |
| ***C07H 19/00*** | (2006.01) |
| ***C12N 15/113*** | (2010.01) |
| ***A61K 31/7125*** | (2006.01) |
| ***A61K 47/48*** | (2006.01) |

(52) U.S. Cl.

CPC ........ *C12N 15/1131* (2013.01); *A61K 31/7125* (2013.01); *A61K 47/48023* (2013.01); *A61K 47/48046* (2013.01); *A61K 47/48053* (2013.01); *A61K 47/48092* (2013.01); *A61K 47/48123* (2013.01); *A61K 47/48238* (2013.01); *A61K 47/48369* (2013.01); *C12N 15/111* (2013.01); *C12N 15/113* (2013.01); *C12N 2310/11* (2013.01); *C12N 2310/113* (2013.01); *C12N 2310/141* (2013.01); *C12N 2310/315* (2013.01); *C12N 2310/321* (2013.01); *C12N 2310/3231* (2013.01); *C12N 2310/351* (2013.01); *C12N 2310/3515* (2013.01); *C12N 2320/30* (2013.01)

(58) Field of Classification Search

None

See application file for complete search history.

(56) References Cited

U.S. PATENT DOCUMENTS

| | | | |
|---|---|---|---|
| 5,994,517 | A | 11/1999 | Ts'o et al. |
| 6,300,319 | B1 | 10/2001 | Manoharan |
| 6,906,182 | B2 | 6/2005 | Ts'o et al. |
| 7,491,805 | B2 | 2/2009 | Vargeese et al. |
| 8,106,022 | B2 | 1/2012 | Manoharan et al. |
| 8,129,515 | B2 | 3/2012 | Esau et al. |
| 8,163,708 | B2 | 4/2012 | Elmen et al. |
| 8,288,356 | B2 | 10/2012 | Obad et al. |
| 8,313,772 | B2 | 11/2012 | Rozema et al. |
| 8,361,980 | B2 | 1/2013 | Kauppinen et al. |
| 8,404,659 | B2 | 3/2013 | Kauppinen et al. |
| 8,426,554 | B2 | 4/2013 | Rozema et al. |
| 8,450,467 | B2 | 5/2013 | Manoharan et al. |
| 8,828,956 | B2 | 9/2014 | Manoharan et al. |
| 2006/0148740 | A1 | 7/2006 | Platenburg |
| 2010/0183639 | A1 | 7/2010 | Uhlmann et al. |
| 2011/0243880 | A1 | 10/2011 | Yurkovetskiy et al. |
| 2012/0122801 | A1 | 5/2012 | Platenburg et al. |
| 2012/0157509 | A1 | 6/2012 | Hadwiger et al. |
| 2013/0178512 | A1 | 7/2013 | Manoharan et al. |
| 2014/0350090 | A1 | 11/2014 | Bhat et al. |

FOREIGN PATENT DOCUMENTS

| | | |
|---|---|---|
| WO | WO 95/30746 | 11/1995 |
| WO | WO 00/76554 | 12/2000 |
| WO | WO 01/25248 | 4/2001 |
| WO | WO 2004094595 | 11/2004 |
| WO | WO 2005013901 | 2/2005 |
| WO | WO 2005061710 | 7/2005 |
| WO | WO 2005107816 | 11/2005 |
| WO | WO 2006/069584 A2 | 7/2006 |
| WO | WO 2006078217 | 7/2006 |
| WO | WO 2006078278 | 7/2006 |
| WO | WO 2006112872 | 10/2006 |
| WO | WO 2007021896 | 2/2007 |

(Continued)

OTHER PUBLICATIONS

Bhat et al., "RG-101, a GalNAC-conjugated anti-miR employing a unique mechanism of action by targeting host factor microRNA-122 (miR-122), demonstrates potent activity and reduction of HCV in preclinical studies," 64th Annual Meeting AASLD, Washington D.C. Nov. 3, 2013, 1 page.

(Continued)

*Primary Examiner* — Tracy Vivlemore
*Assistant Examiner* — Kate Poliakova
(74) *Attorney, Agent, or Firm* — McNeill Baur PLLC

(57) ABSTRACT

Described herein are compositions and methods for the inhibition of miR-122 activity. The compositions have certain nucleoside modifications that yield potent inhibitors of miR-122 activity. The compounds may comprise conjugates to facilitate delivery to the liver. The compositions may be administered to subjects infected with hepatitis C virus, as a treatment for hepatitis C virus and related conditions.

20 Claims, 12 Drawing Sheets

(56) References Cited

FOREIGN PATENT DOCUMENTS

| | | | |
|---|---|---|---|
| WO | WO 2007027775 | | 3/2007 |
| WO | WO 2007027894 | | 3/2007 |
| WO | WO 2007112753 | | 10/2007 |
| WO | WO 2007112754 | | 10/2007 |
| WO | WO 2008091703 | | 7/2008 |
| WO | WO 2008132234 | | 11/2008 |
| WO | WO 2009043353 | | 4/2009 |
| WO | WO 2009068033 | | 6/2009 |
| WO | WO 2009073809 | | 6/2009 |
| WO | WO 2009/091972 | A2 | 7/2009 |
| WO | WO 2010076248 | | 7/2010 |
| WO | WO 2010122538 | | 10/2010 |
| WO | WO 2010/144485 | A1 | 12/2010 |
| WO | WO 2011047312 | | 4/2011 |
| WO | WO 2011130458 | | 10/2011 |
| WO | WO 2012007477 | | 1/2012 |
| WO | WO 2012083046 | | 6/2012 |
| WO | WO 2012089352 | | 7/2012 |
| WO | WO 2012175733 | | 12/2012 |
| WO | WO 2013000855 | | 1/2013 |
| WO | WO 2013000856 | | 1/2013 |
| WO | WO 2013033230 | | 3/2013 |
| WO | WO 2013068347 | | 5/2013 |
| WO | WO 2013068348 | | 5/2013 |
| WO | WO 2013/192576 | A2 | 12/2013 |
| WO | WO 2014/048441 | A1 | 4/2014 |
| WO | WO 2014076195 | | 5/2014 |
| WO | WO 2014118267 | | 8/2014 |
| WO | WO 2014118272 | | 8/2014 |
| WO | WO 2014179445 | | 11/2014 |
| WO | WO 2014179446 | | 11/2014 |
| WO | WO 2014179620 | | 11/2014 |

OTHER PUBLICATIONS

Fabani et al., "miR-122 targeting with LNA/2'-O-methyl oligonucleotide mixmers, peptide nucleic acids (PNA), and PNA-peptide conjugates," RNA, 2008, 14:336-346.

Lehmann et al., "Synthesis and properties of bile acid phosphoramidites 5'-tethered to antisense oligodeoxynucleotides against HCV," Bioorg Med Chem., 2001, 9:1827-1835.

Merwin et al., "Targeted Delivery of DNA Using YEE(GalNAcAH)$_3$, a Synthetic Glycopeptide Ligand for the Asialoglycoprotein Receptor," Bioconjug Chem., 1994, 5:612-620.

Liu et al., "Pharmacokinetics and Pharmacology of RG-101, a Novel Galnac-conjugated Oligonucleotide Targeting MicroRNA-122, in Healthy Volunteers," poster presented at the European Association for the Study of the Liver 50th Annual "The International Liver Congress", Apr. 25, 2015, 1 page.

Neben et al., "Pharmacokinetics, Pharmacodynamics, and Toxicity Profile of RG-101, a Novel Galnac-conjugated Hepatocyte-targeting Inhibitor of MicroRNA-122, in Rodents and Cynomolgus Monkeys," poster presented at the European Association for the Study of the Liver 50th Annual "The International Liver Congress", Apr. 25, 2015, 1 page.

Neben et al., "RG-101, a Novel Galnac-conjugated Inhibitor of MicroRNA-122, Demonstrates Significant Viral Load Reduction and Reduces Liver Steatosis in Human Chimeric Mice Infected with Genotype 1A or Hard-to-treat Genotype 3A Hepatitis C Virus (HCV)," poster presented at the European Association for the Study of the Liver 50th Annual "The International Liver Congress", Apr. 25, 2015, 1 page.

Regulus Thereapeutics Inc., "Regulus to Present Late-Breaking, Expanded RG-101 Data Set for the Treatment of HCV at The International Liver Congress™ 2015 (ILC 2015)," Press Release, Apr. 9, 2015, 3 pages.

Regulus Thereapeutics Inc., "Late-Breaking Oral Presentation at the International Liver Congress™ (ILC 2015) Highlights RG-101's Potent, Durable and Pan-Genotypic Effects in Diverse HCV Population," Press Release, Apr. 25, 2015, 3 pages.

Van Der Ree et al., "A Single Subcutaneous Dose of 2 mg/kg or 4 mg/kg of RG-101, a Galnac-Conjugated Oligonucleotide with Antagonist Activity against miR-122, Results in Significant Viral Load Reductions in Chronic Hepatitis C Patients," presentation at the European Association for the Study of the Liver 50th Annual "The International Liver Congress", Apr. 25, 2015, 20 pages.

Leriche et al., "Cleavable linkers in chemical biology," Bioorg Med Chem., 2012, 20:571-582.

Regulus Theraputics Inc., "RG-101: A Potentially Disruptive Agent to the HCV Treatment Landscape," Presentation, Feb. 9, 2015, 18 pages.

Xanthopoulos, Transcript of Oral Presentation, 12$^{th}$ Annual Needham Healthcare Conference, May 1, 2013, 9 pages.

Bhat et al., "RG-101, a GalNAC-conjugated anti-miR employing a unique mechanism of action by targeting host factor microRNA-122 (miR-122), demonstrates potent activity and reduction of HCV in preclinical studies," AASLD Abstracts, Abstract #LB-28, Hepatology, 2013, 58:1393A.

Bhat et al., "RG-101, a GalNAC-conjugated anti-miR employing a unique mechanism of action by targeting host factor microRNA-122 (miR-122), demonstrates potent activity and reduction of HCV in preclinical studies," 64th Annual Meeting AASLD, Washington D.C. Nov. 3, 2013, 1 page.

Biessen et al., "Targeted delivery of oligodeoxynucleotides to parenchymal liver cells in vivo," Biochem. J., 1999, 340: 783-792.

Biton et al., "DNA photocleavage by DNA and DNA-LNA amino acid-dye conjugates," Bioconjug Chem., 2010, 21:616-621, includes supplemental data, (7 pages).

Duff et al., "Intrabody-Specific Delivery of Antisense Conjugates in Animals: Ligand-Linker-Antisense Oligomer Conjugates," Methods Enzymol., 2000, 313: 297-321.

Fabani et al., "miR-122 targeting with LNA/2'-O-methyl oligonucleotide mixmers, peptide nucleic acids (PNA), and PNA-peptide conjugates," RNA, 2008, 14:336-346.

Gagnon et al., "Antisense and antigene inhibition of gene expression by cell-permeable oligonucleotide-oligospermine conjugates," J Am Chem Soc., 2011, 133:8404-8407.

Gibson et al., "Targeting microRNAs and Biological Networks: An Innovative Approach to Treat Disease," Presentation, Tides Conference, May 15, 2013, 31 pages.

Godeau et al., "Lipid-conjugated oligonucleotides via "click chemistry" efficiently inhibit hepatitis C virus translation," J Med Chem., 2008, 51:4374-4376, includes supplemental data (19 pages).

Hangeland et al., "Cell-Type Specific and Ligand Specific Enhancement of Cellular Uptake of Oligodeoxynucleoside-Methylphosphonates Covalently Linked with a Neoglycopeptide, YEE(ah-GalNAc)$_3$," Bioconjug Chem., 1995, 6:695-701.

Haussecker et al., "miR-122 Continues to Blaze the Trail for MicroRNA Therapeutics," Molecular Therapy, 2010, 18:240-242.

Hogan et al., "Anti-miRs Competitively Inhibit microRNAs in Argonaute Complexes," PLoS One, 2014, 9:e100951, 11 pages.

Horwich et al., "Design and delivery of antisense oligonucleotides to block microRNA function in cultured Drosophila and human cells," Nature Protocols, 2008, 3:1537-1549.

Janssen et al., "Treatment of HCV Infection by Targeting MicroRNA," NEJM, 2013, 368:1685-1694.

Jopling, "Targeting microRNA-122 to Treat Hepatitis C Virus Infection," Viruses, 2010, 2:1382-1393.

Karskela et al., "Synthesis of Cellular Uptake of Fluorescently Labeled Multivalient Hyaluronan Disaccharide Conjugates of Oligonucleotide Phosphorothioates," Bioconjugate Chem., 2008, 19:2549-2558.

Katajisto et al., "Solid-Phase Synthesis of Multiantennary Oligonucleotide Glycoconjugates Utilizing On-Support Oximation," Bioconjugate Chem., 2004, 15:890-896.

Lehmann et al., "Synthesis and properties of bile acid phosphoramidites 5'-tethered to antisense oligodeoxynucleotides against HCV," Bioorg Med Chem., 2001, 9:1827-1835.

Maier et al., "Synthesis of Antisense Oligonucleotides Conjugated to a Multivalent Carbohydrate Cluster fo Cellular Targeting," Bioconjugate Chem., 2003, 14:18-29.

(56) References Cited

OTHER PUBLICATIONS

Makino et al., "Intravenous injection with antisense oligodeoxynucleotides against angiotensinogen decreases blood pressure in spontaneously hypertensive rats," Hypertension, 1998, 31:1166-1170.
Manoharan, "Oligonucleotide Conjugates as Potential Antisense Drugs with Improved Uptake, Biodistribution, Targeted Delivery, and Mechanism of Action," Antisense Nucl. Acid Drug Develop., 2002, 12:103-128.
Merwin et al., " Targeted Delivery of DNA Using YEE(GalNAcAH)$_3$, a Synthetic Glycopeptide Ligand for the Asialoglycoprotein Receptor," Bioconjug Chem., 1994, 5:612-620.
Rajur et al., "Covalent protein-oligonucleotide conjugates for efficient delivery of antisense molecules," Bioconjug Chem., 1997, 8:935-940.
Raouane et al., "Synthesis, characterization, and in vivo delivery of siRNA-squalene nanoparticles targeting fusion oncogene in papillary thyroid carcinoma," J Med Chem, 2011, 54:4067-4076, includes supplemental data (10 pages).
Regulus Thereapeutics Inc., "Regulus Provides Update on 'Road to the Clinic' Strategy and Reports First Quarter 2013 Financial Results and Recent Highlights," Press Release, May 14, 2013, 3 pages.
Regulus Thereapeutics Inc., "Targeting microRNAs and Biological Networks: An Innovative Approach to Treat Disease," Presentation, Tides Conference, May 15, 2013, 31 pages.
Regulus Thereapeutics Inc., "Positive Preclinical Profile of RG-101, a GalNAc-conjugated anti-miR Targeting microRNA-122, Supports Clinical Development for the Treatment of HCV," Press Release, Nov. 4, 2013, 2 pages.
Regulus Thereapeutics Inc., "RG-101 Human Proof-of-Concept," Presentation, Oct. 22, 2014, 23 pages.
Regulus Thereapeutics Inc., "A Single Subcutaneous Dose of 2mg/kg of RG-101, Regulus' Wholly-Owned, GalNac-Conjugated anti-miR Targeting microRNA-122, Demonstrates 4.1 log10 Mean Viral Load Reduction as Monotherapy at Day 29 in Patients with Varied HCV Genotypes and Treatment History, " Press Release, Oct. 22, 2014, 3 pages.
Sliedregt et al., "Design and Synthesis of Novel Amphiphilic Dendritic Galactosides for Selective Targeting of Liposomes to the Hepatic Asialoglycoprotein Receptor," 1999, 42: 609-618.
Spinelli et al., "Glycoclusters on oligonucleotide and PNA scaffolds: synthesis and applications," Chem Soc Rev., 2013, 42:4557-4573.
Tyagi et al., "Molecular beacons: probes that fluoresce upon hybridization," Nat Biotechnol., 1996, 14:303-308.
Tripathi et al., "The Nuclear-Retained Noncoding RNA MALAT1 Regulates Alternative Splicing by Modulating SR Splicing Factor Phosphorylation," Molecular Cell, 2010, 39:925-938.
Van Rooij et al., "Developing MicroRNA Therapeutics," Circ Res., 2012, 110:496-507.
Zatsepin et al., "Synthesis and Applications of Oligonucleotide—Carbohydrate Conjugate," Chemistry & Biodiversity, Helvetica Chimica Acta, 2004, 1(10):1413-1415.
Zheng et al., "Distribution and anti-HBV effects of antisense oligodeoxynucleotides conjugated to galactosylated poly-L-lysine," World J Gastroenterol., 2003, 9:1251-1255.
Zhu et al., "Site-specific delivery of oligonucleotides to hepatocytes after systemic administration," Bioconjug Chem, 2008, 19:290-298.
Zhu et al., "Targeted Delivery of siRNA to Hepatocytes and Hepatic Stellate Cells by Bioconjugation," Bioconjug Chem., 2010, 21:2119-2127.
International Search Report and Written Opinion for PCT/US2014/036136, mailed Oct. 13, 2014, 12 pages.
International Search Report and Written Opinion for PCT/US2014/036137, mailed Dec. 15, 2014, 20 pages.

(I)

(II)

(III)

SEQUENCE LISTING

```
<160> NUMBER OF SEQ ID NOS: 10

<210> SEQ ID NO 1
<211> LENGTH: 22
<212> TYPE: RNA
<213> ORGANISM: Homo sapiens

<400> SEQUENCE: 1

uggaguguga caaugguguu ug                                           22


<210> SEQ ID NO 2
<211> LENGTH: 85
<212> TYPE: RNA
<213> ORGANISM: Homo sapiens

<400> SEQUENCE: 2

ccuuagcaga gcuguggagu gugacaaugg uguuuguguc uaaacuauca aacgccauua  60

ucacacuaaa uagcuacugc uaggc                                        85
```

<210> SEQ ID NO 3
<211> LENGTH: 16
<212> TYPE: DNA
<213> ORGANISM: Artificial sequence
<220> FEATURE:
<223> OTHER INFORMATION: Synthetic

<400> SEQUENCE: 3
ccattgtcac actcca 16

<210> SEQ ID NO 4
<211> LENGTH: 18
<212> TYPE: DNA
<213> ORGANISM: Artificial sequence
<220> FEATURE:
<223> OTHER INFORMATION: Synthetic

<400> SEQUENCE: 4
acaccattgt cacactcc 18

<210> SEQ ID NO 5
<211> LENGTH: 21
<212> TYPE: DNA
<213> ORGANISM: Artificial sequence
<220> FEATURE:
<223> OTHER INFORMATION: Synthetic

<400> SEQUENCE: 5
caaacaccat tgtcacactc c 21

<210> SEQ ID NO 6
<211> LENGTH: 22
<212> TYPE: DNA
<213> ORGANISM: Artificial sequence
<220> FEATURE:
<223> OTHER INFORMATION: Synthetic

<400> SEQUENCE: 6
caaacaccat tgtcacactc ct 22

<210> SEQ ID NO 7
<211> LENGTH: 15
<212> TYPE: DNA
<213> ORGANISM: Artificial sequence
<220> FEATURE:
<223> OTHER INFORMATION: Synthetic

<400> SEQUENCE: 7
ccattgtcac actcc 15

<210> SEQ ID NO 8
<211> LENGTH: 13
<212> TYPE: DNA
<213> ORGANISM: Artificial sequence
<220> FEATURE:
<223> OTHER INFORMATION: Synthetic

<400> SEQUENCE: 8
ttgtcacact cca 13

<210> SEQ ID NO 9
<211> LENGTH: 8
<212> TYPE: DNA
<213> ORGANISM: Artificial sequence
<220> FEATURE:

-continued

```
<223> OTHER INFORMATION: Synthetic

<400> SEQUENCE: 9

cacactcc                                                               8


<210> SEQ ID NO 10
<211> LENGTH: 16
<212> TYPE: DNA
<213> ORGANISM: Artificial sequence
<220> FEATURE:
<223> OTHER INFORMATION: Synthetic

<400> SEQUENCE: 10

ccattgtcac actcct                                                      16
```

MICRORNA COMPOUNDS AND METHODS FOR MODULATING MIR-122

This application is a continuation of U.S. patent application Ser. No. 14/266,136, filed Apr. 30, 2014, which claims the benefit of U.S. Provisional Application Nos. 61/818,432, filed May 1, 2013; 61/822,112, filed May 10, 2013; 61/839,550, filed Jun. 26, 2013; 61/895,784, filed Oct. 25, 2013; 61/898,704, filed Nov. 1, 2013; and 61/927,897, filed Jan. 15, 2014; each of which is incorporated by reference herein in its entirety for any purpose.

FIELD OF INVENTION

Provided herein are compounds and methods for use in modulating the activity of miR-122. Such methods comprise treatment of diseases related to miR-122 activity, such HCV infection.

DESCRIPTION OF RELATED ART

MicroRNAs (microRNAs), also known as "mature microRNA" are small (approximately 18-24 nucleotides in length), non-coding RNA molecules encoded in the genomes of plants and animals. In certain instances, highly conserved, endogenously expressed microRNAs regulate the expression of genes by binding to the 3'-untranslated regions (3'-UTR) of specific mRNAs. More than 1000 different microRNAs have been identified in plants and animals. Certain mature microRNAs appear to originate from long endogenous primary microRNA transcripts (also known as pri-microRNAs, pri-mirs, pri-miRs or pri-pre-microRNAs) that are often hundreds of nucleotides in length (Lee, et al., EMBO J., 2002, 21(17), 4663-4670).

miR-122, a microRNA abundantly and specifically expressed in the liver, is a critical host factor for hepatitis C virus accumulation (Jopling et al., Science. 2005, 309(5740), 1577-81). miR-122 interacts with HCV by binding to two closely spaced seed sequence sites in the 5' non-coding region of the HCV genome, resulting in stabilization of the HCV genome, supporting replication and translation (Jangra et al., J Virol., 2010, 84: 6615-6625; Machlin, et al., 2011). Importantly, the miR-122 binding sites are completely conserved in the HCV genome across all genotypes and subtypes (Wilson et al., J. Virol., 2011, 85: 2342-2350) Inhibition of miR-122 with anti-miR results in reduced total circulating cholesterol levels in mice and cynomolgus monkey, as well as changes in the expression of genes involved in cholesterol homeostasis, fatty acid, and lipid metabolism (Esau et al., 2006, Cell Metabolism, 3: 87-98). In chronically HCV-infected chimpanzees, weekly intravenous administration of anti-miR to long-lasting and reversible suppression of HCV RNA levels and reduced total serum cholesterol (Lanford et al., 2010, Science, 327:198-201). In chronic treatment naïve HCV infected patients, anti-miR-122 treatment led to a reduction in serum HCV RNA, thus demonstrating clinical proof-of-concept.

Hepatitis C (HCV) is a hepatotropic RNA virus in the Flaviviridae family and, addition to causing HCV infection, is a major cause of chronic liver disease and hepatocellular carcinoma. The current standard-of-care treatment, pegylated interferon in combination with ribavirin, is poorly tolerated by many patients and can have a response rate as low as 50% in some patients. Several direct acting anti-viral NS3 protease inhibitors are currently approved for use in HCV-infected patients, however the emergence of resistance mutations in HCV requires treatment with additional agents. Developing therapies include NS3/4A protease inhibitors, NS5A protein inhibitors, nucleoside/tide NS5B polymerase inhibitors and non-nucleoside NS5B inhibitors. However, there remains a need for additional therapies to treat infected individuals who do not respond to current treatments, who relapse following successful treatment, or who have a low tolerability for one or more currently used drugs. Resistance to antiviral therapy is a major problem associated with a high mutation rate of HCV and is seen even with combinations of drugs working through multiple mechanisms. Accordingly, therapeutics that target conserved, mutation-resistant viral host factors, such as miR-122, represent an opportunity to effect higher and more durable cure rates.

SUMMARY OF INVENTION

Provided herein are compounds comprising a modified oligonucleotide consisting of 16 to 22 linked nucleosides, wherein the nucleobase sequence of the modified oligonucleotide is complementary to miR-122 (SEQ ID NO: 1) and wherein the modified oligonucleotide comprises at least 16 contiguous nucleosides of the following nucleoside pattern I in the 5' to 3' orientation:

$$(R)_X—N^Q—N^Q—N^B—N^B—N^Q—N^B—N^Q—N^B—N^Q—N^B—N^B—(N^Z)_Y$$

wherein each R is, independently, a non-bicyclic nucleoside or a bicyclic nucleoside;

X is from 4 to 10;

each $N^B$ is, independently, a bicyclic nucleoside;

each $N^Q$ is, independently, a non-bicyclic nucleoside;

Y is 0 or 1; and $N^Z$ is a modified nucleoside or an unmodified nucleoside.

In certain embodiments, a compound provided herein comprises a modified oligonucleotide comprising at least 16, at least 17, at least 18, at least 19, at least 20, at least 21, or 22 contiguous nucleosides of nucleoside pattern I.

In certain embodiments, each bicyclic nucleoside is independently selected from an LNA nucleoside, a cEt nucleoside, and an ENA nucleoside. In certain embodiments, at least two bicyclic nucleosides are different from one another. In certain embodiments, all bicyclic nucleosides have the same sugar moiety as one another. In certain embodiments, each bicyclic nucleoside is a cEt nucleoside. In certain embodiments, a cEt nucleoside is an S-cEt nucleoside. In certain embodiments, a cEt nucleoside is an R-cEt nucleoside. In certain embodiments, each bicyclic nucleoside is an LNA nucleoside.

In certain embodiments, at least two non-bicyclic nucleosides comprise sugar moieties that are different from one another. In certain embodiments, each non-bicyclic nucleoside has the same type of sugar moiety. In certain embodiments, each non-bicyclic nucleoside is independently selected from a β-D-deoxyribonucleoside, a β-D-ribonucleoside, 2'-O-methyl nucleoside, a 2'-O-methoxyethyl nucleoside, and a 2'-fluoronucleoside. In certain embodiments, each non-bicyclic nucleoside is independently selected from a β-D-deoxyribonucleoside, and a 2'-O-methoxyethyl nucleoside. In certain embodiments, each non-bicyclic nucleoside is a β-D-deoxyribonucleoside. In certain embodiments, each non-bicyclic nucleoside is a 2'-MOE nucleoside. In certain embodiments, no more than two non-bicyclic nucleosides are 2'-MOE nucleosides, wherein each other non-bicyclic nucleoside is a β-D-deoxyribonucleoside. In certain embodiments, the 5'-most and the 3'-most non-bicyclic nucleosides are 2'-MOE nucleosides and each other non-bicyclic nucleoside is a β-D-deoxyribonucleoside. In certain embodiments, two non-bicyclic nucleosides are 2'-MOE nucleosides and each other non-bicyclic nucleoside is a β-D-deoxyribonucleoside.

In certain embodiments, each R is a 2'-MOE nucleoside. In certain embodiments, X is 4, 5, 6, 7, 8, 9, or 10. In certain embodiments, Y is 0. In certain embodiments, Y is 1.

In certain embodiments, X is 7, each R is a 2'-O-methoxyethyl nucleoside, each $N^B$ is an S-cEt nucleoside, each $N^Q$ is a β-D-deoxyribonucleoside, and Y is 0.

In certain embodiments, X is 4; $(R)_X$ is $N^{R1}$—$N^{R2}$—$N^{R3}$—$N^{R4}$, wherein each of $N^{R1}$ and $N^{R3}$ is a S-cEt nucleoside and each of $N^{R2}$ and $N^{R4}$ is a β-D-deoxyribonucleoside; each $N^B$ is an S-cEt nucleoside; each $N^Q$ is a β-D-deoxyribonucleoside; Y is 1; and $N^Z$ is a β-D-deoxyribonucleoside.

In certain embodiments, X is 4; $(R)_X$ is $N^{R1}$—$N^{R2}$—$N^{R3}$—$N^{R4}$, wherein each of $N^{R1}$ and $N^{R4}$ is a S-cEt nucleoside and each of $N^{R2}$ and $N^{R3}$ is a β-D-deoxyribonucleoside; each $N^B$ is an S-cEt nucleoside; each $N^Q$ is a β-D-deoxyribonucleoside; Y is 1; and $N^Z$ is a 2'-O-methoxyethyl nucleoside.

In certain embodiments, X is 7; $(R)_X$ is $N^{R1}$—$N^{R2}$—$N^{R3}$—$N^{R4}$—$N^{R5}$—$N^{R6}$—$N^{R7}$, wherein each of $N^{R1}$, $N^{R2}$, $N^{R3}$, and $N^{R4}$ and is a 2'-O-methoxyethyl nucleoside, each of $N^{R5}$ and $N^{R7}$ is a β-D-deoxyribonucleoside, and $N^{R6}$ is S-cEt nucleoside; each $N^B$ is an S-cEt nucleoside; each $N^Q$ is a β-D-deoxyribonucleoside; and Y is 0.

In certain embodiments, X is 7; $(R)_X$ is $N^{R1}$—$N^{R2}$—$N^{R3}$—$N^{R4}$—$N^{R5}$—$N^{R6}$—$N^{R7}$, wherein each of $N^{R1}$, $N^{R2}$, $N^{R3}$, $N^{R4}$, and $N^{R5}$ is a 2'-O-methoxyethyl nucleoside, $N^{R6}$ is S-cEt nucleoside, and $N^{R7}$ is a β-D-deoxyribonucleoside; each $N^B$ is an S-cEt nucleoside; each $N^Q$ is a β-D-deoxyribonucleoside; and Y is 0.

In certain embodiments, X is 7; $(R)_X$ is $N^{R1}$—$N^{R2}$—$N^{R3}$—$N^{R4}$—$N^{R5}$—$N^{R6}$—$N^{R7}$, wherein each of $N^{R1}$, $N^{R2}$, $N^{R3}$, $N^{R4}$, $N^{R5}$, and $N^{R6}$ is 2'-O-methoxyethyl nucleoside, and $N^{R7}$ is a β-D-deoxyribonucleoside; each $N^B$ is an S-cEt nucleoside; each $N^Q$ is a β-D-deoxyribonucleoside; and Y is 0.

In certain embodiments, X is 10; $(R)_X$ is $N^{R1}$—$N^{R2}$—$N^{R3}$—$N^{R4}$—$N^{R5}$—$N^{R6}$—$N^{R7}$—$N^{R8}$—$N^{R9}$—$N^{R10}$, wherein each of $N^{R1}$, $N^{R2}$, $N^{R3}$, $N^{R4}$, $N^{R5}$, and $N^{R6}$ is 2'-O-methoxyethyl nucleoside, each of $N^{R7}$ and $N^{R9}$ is a an S-cEt nucleoside; each of $N^{R8}$ and $N^{R10}$ is a β-D-deoxyribonucleoside; each $N^B$ is an S-cEt nucleoside; each $N^Q$ is a β-D-deoxyribonucleoside; and Y is 0.

In certain embodiments, X is 10; $(R)_X$ is $N^{R1}$—$N^{R2}$—$N^{R3}$—$N^{R4}$—$N^{R5}$—$N^{R6}$—$N^{R7}$—$N^{R8}$—$N^{R9}$—$N^{R10}$, wherein each of $N^{R1}$, $N^{R2}$, $N^{R3}$, $N^{R4}$, $N^{R5}$, and $N^{R6}$ is 2'-O-methoxyethyl nucleoside, each of $N^{R7}$ and $N^{R9}$ is a an S-cEt nucleoside; and each of $N^{R8}$ and $N^{R10}$ is a β-D-deoxyribonucleoside; each $N^B$ is an S-cEt nucleoside; each $N^Q$ is a β-D-deoxyribonucleoside; Y is 1 and $N_Z$ is a 2'-O-methoxyethyl nucleoside.

In certain embodiments, X is 4; $(R)_X$ is $N^{R1}$—$N^{R2}$—$N^{R3}$—$N^{R4}$ wherein each of $N^{R1}$ and $N^{R4}$ is an S-cEt nucleoside, and each of $N^{R1}$ and $N^{R3}$ is a β-D-deoxyribonucleoside; each $N^B$ is an S-cEt nucleoside; each $N^Q$ is a β-D-deoxyribonucleoside; Y is 1 and $N^Z$ is a β-D-deoxyribonucleoside.

In certain embodiments, X is 4; $(R)_X$ is $N^{R1}$—$N^{R2}$—$N^{R3}$—$N^{R4}$ wherein $N^{R1}$ is a 2'-O-methoxyethyl nucleoside, each of $N^{R2}$ and $N^{R4}$ is an S-cEt nucleoside, and $N^{R3}$ is a β-D-deoxyribonucleoside; each $N^B$ is an S-cEt nucleoside; each $N^Q$ is a β-D-deoxyribonucleoside; Y is 1 and $N^Z$ is a 2'-O-methoxyethyl nucleoside.

In certain embodiments, the nucleobase sequence of the modified oligonucleotide is at least 90%, at least 92%, at least 93%, at least 94%, at least 95%, at least 96%, at least 97%, at least 98%, at least 99%, or 100% complementary to the nucleobase sequence of miR-122 (SEQ ID NO: 1).

In certain embodiments, wherein at least one internucleoside linkage is a modified internucleoside linkage, or wherein each internucleoside linkage is a modified internucleoside linkage, and, optionally, wherein the modified internucleoside linkage is a phosphorothioate internucleoside linkage.

In certain embodiments, the nucleobase sequence of the modified oligonucleotide is selected from SEQ ID NOs: 3 to 6, wherein each T is independently selected from T and U.

In certain embodiments, the modified oligonucleotide has 0, 1, 2, or 3 mismatches with respect to the nucleobase sequence of miR-122.

In certain embodiments a compound has the structure:

(SEQ ID NO: 4)
$A_E{}^{Me}C_EA_E{}^{Me}C_E{}^{Me}C_EA_ET_ETGU_SC_SAC_SAC_STC_SC_S$;

(SEQ ID NO: 3)
$C_SCA_STTGU_SC_SAC_SAC_STC_SC_SA$;

(SEQ ID NO: 3)
${}^{Me}C_SCAT_STGT_S{}^{Me}C_SA{}^{Me}C_SA{}^{Me}C_ST{}^{Me}C_S{}^{Me}C_SA_E$;

(SEQ ID NO: 4)
$A_E{}^{Me}C_EA_E{}^{Me}C_ECA_STTGU_SC_SAC_SAC_STC_SC_S$;

(SEQ ID NO: 4)
$A_E{}^{Me}C_EA_E{}^{Me}C_E{}^{Me}C_EA_STTGU_SC_SAC_SAC_STC_SC_S$;

(SEQ ID NO: 4)
$A_E{}^{Me}C_EA_E{}^{Me}C_E{}^{Me}C_EA_ETTGU_SC_SAC_SAC_STC_SC_S$;

(SEQ ID NO: 5)
${}^{Me}C_EA_EA_EA_E{}^{Me}C_EA_EC_SCA_STTGU_SC_SAC_SAC_STC_SC_S$;

(SEQ ID NO: 6)
${}^{Me}C_EA_EA_EA_E{}^{Me}C_EA_EC_SCA_STTGU_SC_SAC_SAC_STC_SC_ST_E$;

(SEQ ID NO: 3)
$C_SCAU_STGU_SC_SAC_SAC_STC_SC_SA$;
or (SEQ ID NO: 3)
${}^{Me}C_EC_SAU_STGU_SC_SAC_SAC_STC_SC_SA_E$;

wherein the superscript "Me" indicates 5-methylcytosine; nucleosides not followed by a subscript are β-D-deoxyribonucleosides; nucleosides followed by a subscript "E" are 2'-MOE nucleosides; nucleosides followed by a subscript "S" are S-cEt nucleosides; and each internucleoside linkage is a phosphorothioate internucleoside linkage.

In some embodiments, a compound has the structure:

$U_STGU_SC_SAC_SAC_STC_SC_SA_S$;
or $C_SA_SC_SA_SC_SU_SC_SC_S$ wherein nucleosides not followed by a subscript are β-D-deoxyribonucleosides; nucleosides followed by a subscript "S" are S-cEt nucleosides; and each internucleoside linkage is a phosphorothioate internucleoside linkage. In some such embodiments, the compound is compound 38591, 38633, 38998, or 38634.

Any of the compounds provided herein may comprise a conjugate moiety linked to the 5' terminus or the 3' terminus of the modified oligonucleotide. In certain embodiments, the compound comprises a conjugate moiety linked to the 3' terminus of the modified oligonucleotide. In certain embodiments, the compound comprises a conjugate moiety linked to the 5' terminus of the modified oligonucleotide. In certain embodiments, the compound comprises a first conjugate moiety linked to the 3' terminus of the modified oligonucleotide and a second conjugate moiety linked to the 5' terminus of the modified oligonucleotide. In certain embodiments, the conjugate moiety comprises at least one ligand selected from a carbohydrate, cholesterol, a lipid, a phospholipid, an antibody, a lipoprotein, a hormone, a peptide, a vitamin, a steroid, and a cationic lipid.

In certain embodiments, a compound has the structure $L_n$-linker-MO, wherein each L is, independently, a ligand and n is from 1 to 10; and MO is a modified oligonucleotide.

In certain embodiments, a compound has the structure $L_n$-linker-X-MO, wherein each L is, independently, a ligand and n is from 1 to 10; X is a phosphodiester linkage or a phosphorothioate linkage; and MO is a modified oligonucleotide.

In certain embodiments, a compound has the structure $L_n$-linker-$X_1$—$N_m$—$X_2$—MO, wherein each L is, independently, a ligand and n is from 1 to 10; each N is, independently, a modified or unmodified nucleoside and m is from 1 to 5; $X_1$ and $X_2$ are each, independently, a phosphodiester linkage or a phosphorothioate linkage; and MO is a modified oligonucleotide.

In certain embodiments, a compound has the structure $L_n$-linker-X—$N_m$—Y-MO, wherein each L is, independently, a ligand and n is from 1 to 10; each N is, independently, a modified or unmodified nucleoside and m is from 1 to 5; X is a phosphodiester linkage or a phosphorothioate linkage; Y is a phosphodiester linkage; and MO is a modified oligonucleotide.

In certain embodiments, a compound has the structure $L_n$-linker-Y—$N_m$—Y-MO, wherein each L is, independently, a ligand and n is from 1 to 10; each N is, independently, a modified or unmodified nucleoside and m is from 1 to 5; each Y is a phosphodiester linkage; and MO is a modified oligonucleotide.

In certain embodiments, if n is greater than 1, $L_n$-linker has the structure:

$$[L—Q']_n—S—Q''—$$

wherein each L is, independently, a ligand; n is from 1 to 10; S is a scaffold; and Q' and Q" are, independently, linking groups.

In certain embodiments, Q' and Q" are each independently selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl)cyclohexane-1-carboxylate, and 6-aminohexanoic acid.

In certain embodiments, a scaffold links 2, 3, 4, or 5 ligands to a modified oligonucleotide. In certain embodiments, a scaffold links 3 ligands to a modified oligonucleotide.

A nonlimiting exemplary Structure E is Structure E(i):

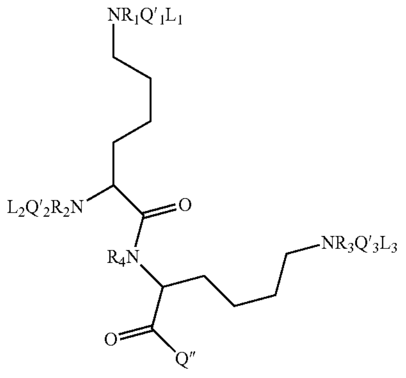

wherein $L_1$, $L_2$, and $L_3$ are each, independently, a ligand; $Q'_1$, $Q'_2$, $Q'_3$, and Q" are each, independently, a linking group; and $R_1$, $R_2$, $R_3$, and $R_4$ are each, independently, selected from H, $C_1$-$C_6$ alkyl, and substituted $C_1$-$C_6$ alkyl.

In some embodiments, $Q'_1$, $Q'_2$, $Q'_3$, and Q" are each, independently, selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl)cyclohexane-1-carboxylate, and 6-aminohexanoic acid. In some embodiments, $R_1$, $R_2$, $R_3$, and $R_4$ are each, independently, selected from H, methyl, ethyl, propyl, isopropyl, and butyl. In some embodiments, $R_1$, $R_2$, $R_3$, and $R_4$ are each selected from H and methyl.

A further nonlimiting exemplary Structure E is Structure E(ii):

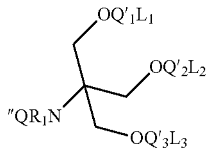

wherein $L_1$, $L_2$, and $L_3$ are each, independently, a ligand; $Q'_1$, $Q'_2$, $Q'_3$, and Q" are each, independently, a linking group; and $R_1$ is selected from H, $C_1$-$C_6$ alkyl, and substituted $C_1$-$C_6$ alkyl.

In some embodiments, $Q'_1$, $Q'_2$, $Q'_3$, and Q" are each, independently, selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl)cyclohexane-1-carboxylate, and 6-aminohexanoic acid. In some embodiments, $R_1$ is selected from H, methyl, ethyl, propyl, isopropyl, and butyl. In some embodiments, $R_1$ is H or methyl.

A further nonlimiting exemplary Structure E is Structure E(iii):

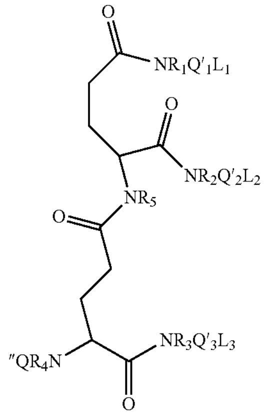

wherein $L_1$, $L_2$, and $L_3$ are each, independently, a ligand; $Q'_1$, $Q'_2$, $Q'_3$, and Q" are each, independently, a linking group; and $R_1$, $R_2$, $R_3$, $R_4$, and $R_5$ are each, independently, selected from H, $C_1$-$C_6$ alkyl, and substituted $C_1$-$C_6$ alkyl.

In some embodiments, $Q'_1$, $Q'_2$, $Q'_3$, and Q" are each, independently, selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl)cyclohexane-1-carboxylate, and 6-aminohexanoic acid. In some embodiments, $R_1$, $R_2$, $R_3$, $R_4$, and $R_5$ are each, independently, selected from H, methyl, ethyl, propyl, isopropyl, and butyl. In some embodiments $R_1$, $R_2$, $R_3$, $R_4$, and $R_5$ are each selected from H and methyl.

A further nonlimiting exemplary Structure E is Structure E(iv):

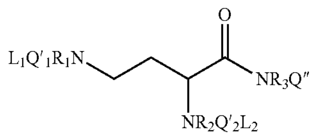

wherein $L_1$ and $L_2$ are each, independently, a ligand; $Q'_1$, $Q'_2$, and Q" are each, independently, a linking group; and $R_1$, $R_2$, and $R_3$ are each, independently, selected from H, $C_1$-$C_6$ alkyl, and substituted $C_1$-$C_6$ alkyl.

In some embodiments, $Q'_1$, $Q'_2$, and Q" are each, independently, selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl) cyclohexane-1-carboxylate, and 6-aminohexanoic acid. In some embodiments, $R_1$, $R_2$, and $R_3$ are each, independently, selected from H, methyl, ethyl, propyl, isopropyl, and butyl. In some embodiments $R_1$, $R_2$, and $R_3$ are each selected from H and methyl.

A further nonlimiting exemplary Structure E is Structure E(v):

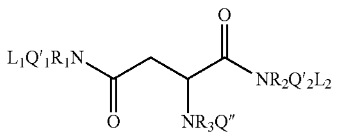

wherein $L_1$ and $L_2$ are each, independently, a ligand; $Q'_1$, $Q'_2$, and Q" are each, independently, a linking group; and $R_1$, $R_2$, and $R_3$ are each, independently, selected from H, $C_1$-$C_6$ alkyl, and substituted $C_1$-$C_6$ alkyl.

In some embodiments, $Q'_1$, $Q'_2$, and Q" are each, independently, selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl)cyclohexane-1-carboxylate, and 6-aminohexanoic acid. In some embodiments, $R_1$, $R_2$, and $R_3$ are each, independently, selected from H, methyl, ethyl, propyl, isopropyl, and butyl. In some embodiments $R_1$, $R_2$, and $R_3$ are each selected from H and methyl.

A further nonlimiting exemplary Structure E is Structure E(vi):

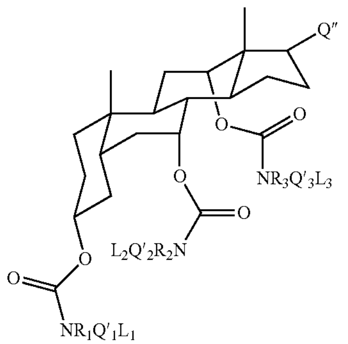

wherein $L_1$, $L_2$, and $L_3$ are each, independently, a ligand; $Q'_1$, $Q'_2$, $Q'_3$, and Q" are each, independently, a linking group; and $R_1$, $R_2$, and $R_3$ are each, independently, selected from H, $C_1$-$C_6$ alkyl, and substituted $C_1$-$C_6$ alkyl.

In some embodiments, $Q'_1$, $Q'_2$, $Q'_3$, and Q" are each, independently, selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl)cyclohexane-1-carboxylate, and 6-aminohexanoic acid. In some embodiments, $R_1$, $R_2$, and $R_3$ are each, independently, selected from H, methyl, ethyl, propyl, isopropyl, and butyl. In some embodiments $R_1$, $R_2$, and $R_3$ are each selected from H and methyl.

A further nonlimiting exemplary Structure E is Structure E(vii):

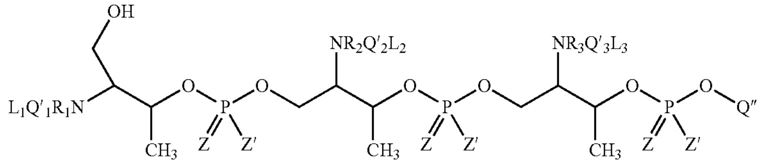

wherein $L_1$, $L_2$, and $L_3$ are each, independently, a ligand; $Q'_1$, $Q'_2$, $Q'_3$, and Q" are each, independently, a linking group; $R_1$, $R_2$, and $R_3$ are each, independently, selected from H, $C_1$-$C_6$ alkyl, and substituted $C_1$-$C_6$ alkyl; and Z and Z' are each independently selected from O and S.

In some embodiments, $Q'_1$, $Q'_2$, $Q'_3$, and Q" are each, independently, selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl)cyclohexane-1-carboxylate, and 6-aminohexanoic acid. In some embodiments, $R_1$, $R_2$, and $R_3$ are each, independently, selected from H, methyl, ethyl, propyl, isopropyl, and butyl. In some embodiments $R_1$, $R_2$, and $R_3$ are each selected from H and methyl. In some embodiments, Z or Z' on at least one P atom is S, and the other Z or Z' is O (i.e., a phosphorothioate linkage). In some embodiments, each —OP(Z)(Z')O— is a phosphorothioate linkage. In some embodiments, Z and Z' are both O on at least one P atom (i.e., a phosphodiester linkage). In some embodiments, each —OP(Z)(Z')O— is a phosphodiester linkage.

A further nonlimiting exemplary Structure E is Structure E(viii):

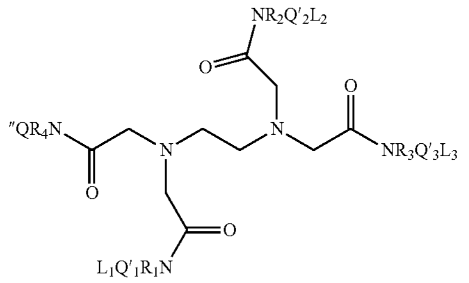

wherein $L_1$, $L_2$, and $L_3$ are each, independently, a ligand; $Q'_1$, $Q'_2$, $Q'_3$, and Q" are each, independently, a linking group; and $R_1$, $R_2$, $R_3$, and $R_4$ are each, independently, selected from H, $C_1$-$C_6$ alkyl, and substituted $C_1$-$C_6$ alkyl.

In some embodiments, $Q'_1$, $Q'_2$, $Q'_3$, and Q" are each, independently, selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl)cyclohexane-1-carboxylate, and 6-aminohexanoic acid. In some embodiments, $R_1$, $R_2$, $R_3$, and $R_4$ are each, independently, selected from H, methyl, ethyl, propyl, isopropyl, and butyl. In some embodiments $R_1$, $R_2$, $R_3$, and $R_4$ are each selected from H and methyl.

Nonlimiting exemplary scaffolds and/or linkers comprising scaffolds, and synthesis thereof, are described, e.g., PCT Publication No. WO 2013/033230, U.S. Pat. No. 8,106,022 B2, U.S. Publication No. 2012/0157509 A1; U.S. Pat. No. 5,994,517; U.S. Pat. No. 7,491,805 B2; U.S. Pat. No. 8,313,772 B2; Manoharan, M., Chapter 16, Antisense Drug Technology, Crooke, S. T., Marcel Dekker, Inc., 2001, 391-469.

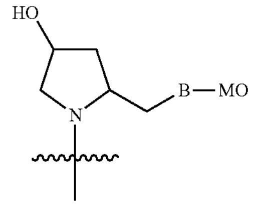

In certain embodiments, a compound has the structure:
wherein:

- B is selected from —O—, —S—, —N($R^N$)—, —Z—P(Z')(Z")O—, —Z—P(Z')(Z")O—$N_m$—X—, and —Z—P(Z')(Z")O—$N_m$—Y—;
- MO is a modified oligonucleotide;
- $R^N$ is selected from H, methyl, ethyl, propyl, isopropyl, butyl, and benzyl;
- Z, Z', and Z" are each independently selected from O and S;
- each N is, independently, a modified or unmodified nucleoside;
- m is from 1 to 5;
- X is selected from a phosphodiester linkage and a phosphorothioate linkage;
- Y is a phosphodiester linkage; and
- the wavy line indicates the connection to the rest of the linker and ligand(s).

In certain embodiments, X is a phosphodiester linkage.

In certain embodiments, n is from 1 to 5, 1 to 4, 1 to 3, or 1 to 2. In certain embodiments, n is 3.

In certain embodiments, at least one ligand is a carbohydrate.

In certain embodiments, at least one ligand is selected from mannose, glucose, galactose, ribose, arabinose, fructose, fucose, xylose, D-mannose, L-mannose, D-galactose, L-galactose, D-glucose, L-glucose, D-ribose, L-ribose, D-arabinose, L-arabinose, D-fructose, L-fructose, D-fucose, L-fucose, D-xylose, L-xylose, alpha-D-mannofuranose, beta-D-mannofuranose, alpha-D-mannopyranose, beta-D-mannopyranose, alpha-D-glucofuranose, Beta-D-glucofuranose, alpha-D-glucopyranose, beta-D-glucopyranose, alpha-D-galactofuranose, beta-D-galactofuranose, alpha-D-galactopyranose, beta-D-galactopyranose, alpha-D-ribofuranose, beta-D-ribofuranose, alpha-D-ribopyranose, beta-D-ribopyranose, alpha-D-fructofuranose, alpha-D-fructopyranose, glucosamine, galactosamine, sialic acid, N-acetylgalactosamine.

In certain embodiments, at least one ligand is selected from N-acetylgalactosamine, galactose, galactosamine, N-formylgalactosamine, N-propionyl-galactosamine, N-n-butanoylgalactosamine, and N-iso-butanoyl-galactosamine.

In certain embodiments, each ligand is N-acetylgalactosamine.

In certain embodiments, a compound has the structure:

(I)

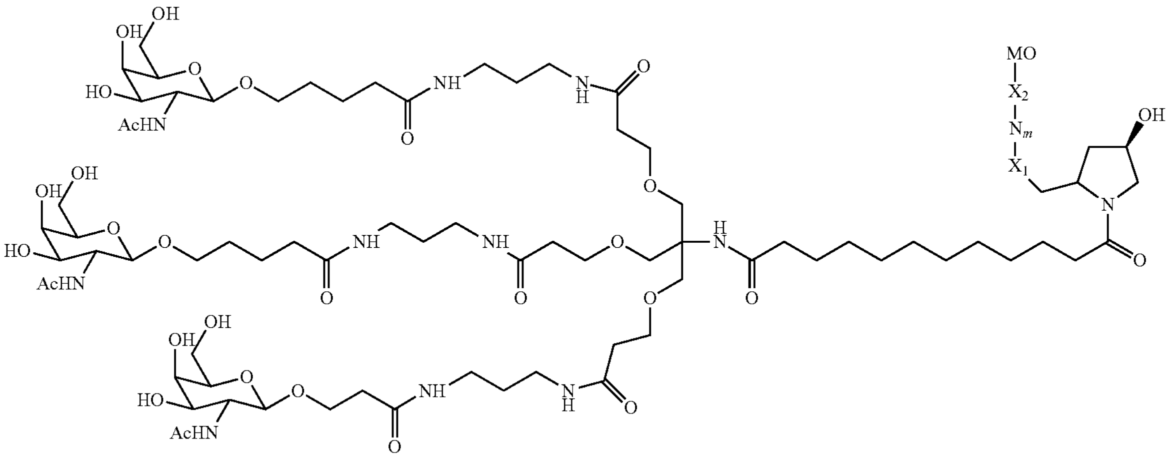

wherein each N is, independently, a modified or unmodified nucleoside and m is from 1 to 5; $X_1$ and $X_2$ are each, independently, a phosphodiester linkage or a phosphorothioate linkage; and MO is a modified oligonucleotide.

In certain embodiments, a compound provided herein comprises a modified nucleotide and a conjugate moiety, wherein the modified oligonucleotide has the structure $C_LCA_LTTG_LT_LCAC_LAC_LTC_LC_L$ (SEQ ID NO: 7), wherein the subscript "L" indicates an LNA and nucleosides not followed by a subscript are β-D-deoxyribonucleosides, and each internucleoside linkage is a phosphorothioate internucleoside linkage, and wherein the conjugate moiety is linked to the 3' terminus of the modified oligonucleotide and has the structure:

(I)

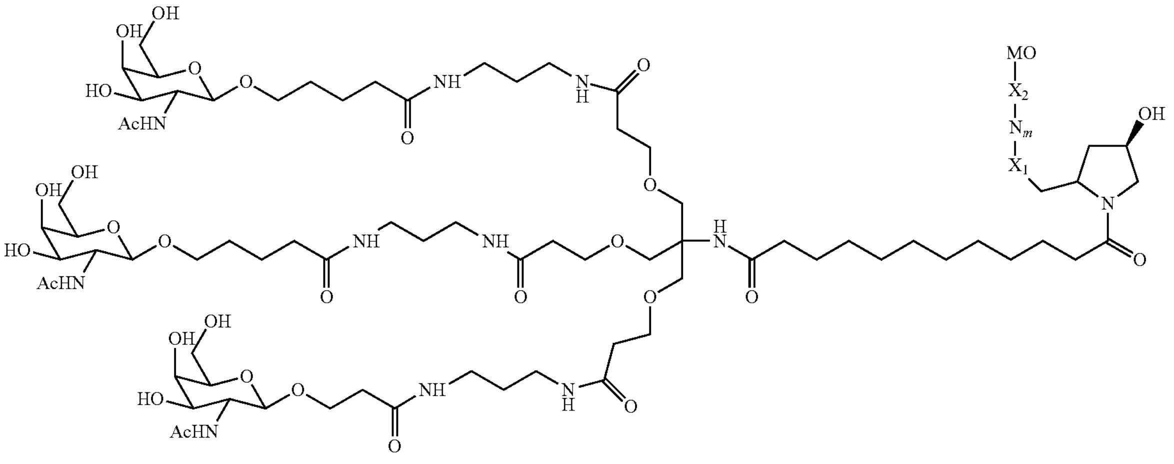

wherein each N is, independently, a modified or unmodified nucleoside and m is from 1 to 5; $X_1$ and $X_2$ are each, independently, a phosphodiester linkage or a phosphorothioate linkage; and MO is a modified oligonucleotide.

In certain embodiments, at least one of $X_1$ and $X_2$ is a phosphodiester linkage. In certain embodiments, each of $X_1$ and $X_2$ is a phosphodiester linkage. In certain embodiments, m is 1. In certain embodiments, m is 2, 3, 4, or 5.

In certain embodiments, $N_m$ is $N'_pN''$, wherein each N' is, independently, a modified or unmodified nucleoside and p is from 0 to 4; and N'' is a nucleoside comprising an unmodified sugar moiety. In certain embodiments, p is 0. In certain embodiments, p is 1, 2, 3, or 4.

In certain embodiments, each N' comprises an unmodified sugar moiety. In certain embodiments, each unmodified sugar moiety is, independently, a β-D-ribose or a β-D-deoxyribose. In certain embodiments, N'' comprises a purine nucleobase. In certain embodiments, N'' comprises a pyrimidine nucleobase. In certain embodiments, at least one N' comprises a purine nucleobase. In certain embodiments, each purine nucleobase is independently selected from adenine, guanine, hypoxanthine, xanthine, and 7-methylguanine. In certain embodiments, N'' is a β-D-deoxyriboadenosine or a β-D-deoxyriboguanosine. In certain embodiments, at least one N' comprises a pyrimidine nucleobase. In certain embodiments, each pyrimidine nucleobase is independently selected from cytosine, 5-methylcytosine, thymine, uracil, and 5,6-dihydrouracil.

In any of the embodiments described herein, the sugar moiety of each N is independently selected from a β-D-ribose, a β-D-deoxyribose, a 2'-O-methoxy sugar, a 2'-O-methyl sugar, a 2'-fluoro sugar, and a bicyclic sugar moiety. In certain embodiments, each bicyclic sugar moiety is independently selected from a cEt sugar moiety, an LNA sugar moiety, and an ENA sugar moiety. In certain embodiments, a cEt sugar moiety is an S-cEt sugar moiety. In certain embodiments, a cEt sugar moiety is an R-cEt sugar moiety. In any embodiments described herein, the sugar moiety of each N may be independently selected from β-D-ribose, a β-D-deoxyribose, and a 2'-fluoro sugar.

Provided herein are compounds comprising a modified nucleotide and a conjugate moiety, wherein the modified oligonucleotide has the structure $A_E{}^{Me}C_EA_E{}^{Me}C_E{}^{Me}C_EA_ET_ETGU_SC_SAC_SAC_STC_SC_S$ (SEQ ID NO: 4), wherein nucleosides not followed by a subscript are β-D-deoxyribonucleosides, nucleosides followed by a subscript "E" are 2'-MOE nucleosides, nucleosides followed by a subscript "S" are S-cEt nucleosides, and each internucleoside linkage is a phosphorothioate internucleoside linkage; and wherein the conjugate moiety is linked to the 3' terminus of the modified oligonucleotide and has the structure:

(II)

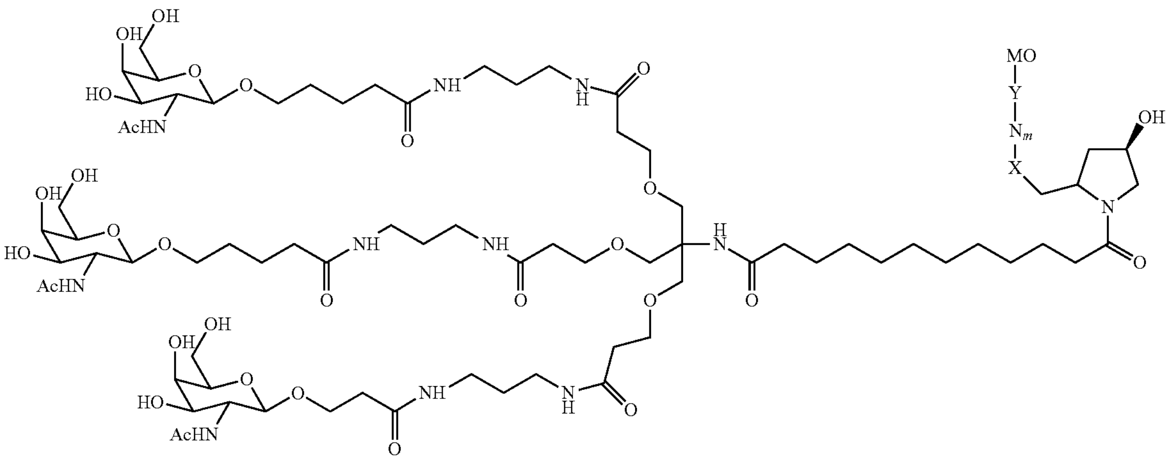

wherein X is a phosphodiester linkage; m is 1; N is a β-D-deoxyriboadenosine; Y is a phosphodiester linkage; and MO is the modified oligonucleotide.

Provided herein are compounds comprising a modified nucleotide and a conjugate moiety, wherein the modified oligonucleotide has the structure $C_LCA_LTTG_LT_LCAC_LA$-$C_LTC_LC_L$ (SEQ ID NO: 7), wherein the subscript "L" indicates an LNA and nucleosides not followed by a subscript are β-D-deoxyribonucleosides, and each internucleoside linkage is a phosphorothioate internucleoside linkage, and wherein the conjugate moiety is linked to the 3' terminus of the modified oligonucleotide and has the structure:

(II)

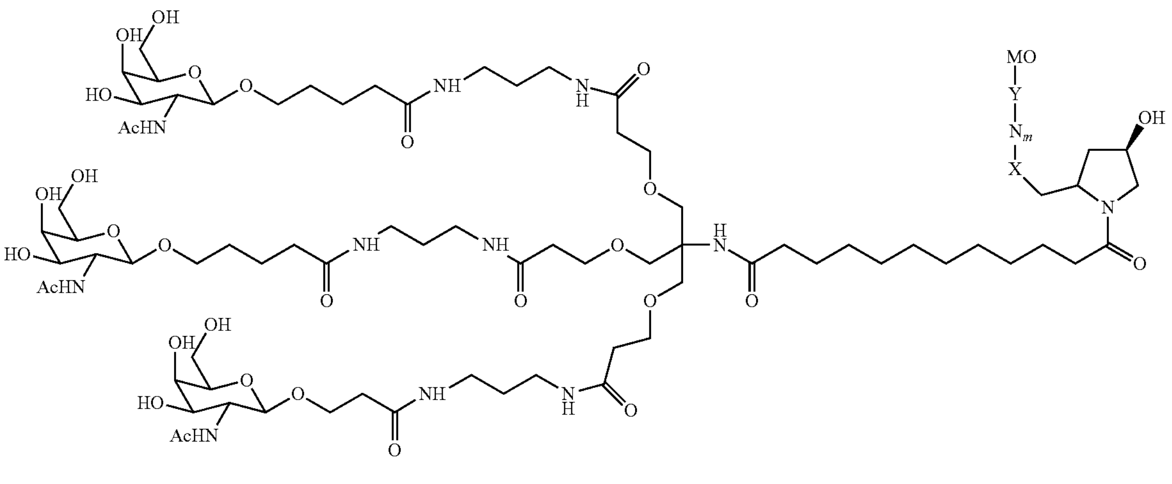

wherein X is a phosphodiester linkage; m is 1; N is a β-D-deoxyriboadenosine; Y is a phosphodiester linkage; and MO is the modified oligonucleotide. In some embodiments, all of the $C_L$ nucleosides are $^{Me}C_L$ nucleosides, wherein the superscript “Me” indicates 5-methylcytosine.

Provided herein are methods of inhibiting the activity of miR-122 in a cell comprising contacting a cell with any compound provided herein. In certain embodiments, the cell is cell is in vivo. In certain embodiments, cell is in vitro.

Provided herein are methods of administering to an HCV-infected subject any of the compounds provided herein. In certain embodiments, the administering reduces the symptoms of HCV infection. In certain embodiments, the administering prevents a rebound in serum HCV RNA. In certain embodiments, the administering delays a rebound in serum HCV RNA. In certain embodiments, a subject having HCV infection is selected for treatment with a compound provided herein. In certain embodiments, an HCV-infected subject is infected with one or more HCV genotypes selected from genotype 1, genotype 2, genotype 3, genotype 4, genotype 5, and genotype 6. In certain embodiments, prior to administration of a compound provided herein, the subject was determined to be infected with one or more HCV genotypes selected from genotype 1, genotype 2, genotype 3, genotype 4, genotype 5, and genotype 6. In certain embodiments, the HCV genotype is selected from genotype 1a, genotype 1b, genotype 2a, genotype 2b, genotype 2c, genotype 2d, genotype 3a, genotype 3b, genotype 3c, genotype 3d, genotype 3e, genotype 3f, genotype 4a, genotype 4b, genotype 4c, genotype 4d, genotype 4e, genotype 4f, genotype 4g, genotype 4h, genotype 4i, genotype 4j, genotype 5a, and genotype 6a. In certain embodiments, the HCV genotype is selected from genotype 1a, 1b, and 2.

Any of the methods provided here may comprise administering at least one additional therapeutic agent. In certain embodiments, the at least one therapeutic agent is selected from a protease inhibitor, a polymerase inhibitor, a cofactor inhibitor, an RNA polymerase inhibitor, a structural protein inhibitor, a non-structural protein inhibitor, a cyclophilin inhibitor, an entry inhibitor, a TLR7 agonist, and an interferon. In certain embodiments, the at least one therapeutic agent is selected from a protease inhibitor, an NS5A inhibitor, an NS3/4A inhibitor, a nucleoside NS5B inhibitor, a nucleotide NS5B inhibitor, a non-nucleoside NS5B inhibitor, a cyclophilin inhibitor and an interferon. In certain embodiments, the at least one therapeutic agent is selected from interferon alfa-2a, interferon alpha-2b, interferon alfacon-1, peginterferon alpha-2b, peginterferon alpha-2a, interferon-alpha-2b extended release, interferon lambda, sofosbuvir, ribavirin, telapravir, boceprevir, vaniprevir, asunaprevir, ritonavir, setrobuvir, daclastavir, simeprevir, alisporivir, mericitabine, tegobuvir, danoprevir, sovaprevir, and neceprevir. In certain embodiments, the at least one therapeutic agent is selected from an interferon, ribavirin, and telapravir.

In certain embodiments, a subject is infected with an HCV variant that is resistant to at least one therapeutic agent. In certain embodiments, a subject is infected with an HCV variant that is resistant to a direct-acting anti-viral agent. In certain embodiments, a subject is infected with an HCV variant that is resistant to at least one therapeutic agent selected from a protease inhibitor, a polymerase inhibitor, a cofactor inhibitor, an RNA polymerase inhibitor, a structural protein inhibitor, a non-structural protein inhibitor, and a cyclophilin inhibitor. In certain embodiments, a subject is infected with an HCV variant that is resistant to at least one therapeutic agent selected from a protease inhibitor, an NS5A inhibitor, an NS3/4A inhibitor, a nucleoside NS5B inhibitor, a nucleotide NS5B inhibitor, a non-nucleoside NS5B inhibitor, and a cyclophilin inhibitor. In certain embodiments, a subject is infected with an HCV variant that is resistant to at least one therapeutic agent selected from sofosbuvir, ribavirin, telapravir, boceprevir, vaniprevir, asunaprevir, ritonavir, setrobuvir, daclastavir, simeprevir, alisporivir, mericitabine, tegobuvir, danoprevir, sovaprevir, and neceprevir.

In certain embodiments, an HCV-infected subject is a non-responder to at least one therapeutic agent. In certain embodiments, an HCV-infected subject is an interferon non-responder. In certain embodiments, an HCV-infected subject is a direct-acting anti-viral non-responder.

Any of the methods provided herein may comprise selecting a subject having a HCV RNA level greater than 350,000 copies per milliliter of serum. In certain embodiments, a subject has an HCV RNA level between 350,000 and 3,500,000 copies per milliliter of serum. In certain embodiments, a subject has an HCV RNA level greater than 3,500,000 copies per milliliter of serum.

In certain embodiments, an HCV-infected subject has an HCV-associated disease. In certain embodiments, an HCV-associated disease is cirrhosis, liver fibrosis, steatohepatitis, steatosis, or hepatocellular carcinoma.

In certain embodiments, an HCV-infected subject has one or more diseases that are not HCV-associated diseases. In certain embodiments, an HCV-infected subject is infected with one or more viruses other than HCV. In certain embodiments, an HCV-infected subject is infected with human immunodeficiency virus (HIV). In certain embodiments, the methods provided herein comprise administering an additional therapeutic agent is an anti-viral agent used in the treatment of HIV infection. In certain embodiments, an additional therapeutic agent is a non-nucleoside reverse transcriptase inhibitors (NNRTIs). In certain embodiments, an additional therapeutic agent is a nucleoside reverse transcriptase inhibitors (NRTIs). In certain embodiments, an additional therapeutic agent is a protease inhibitor. In certain embodiments, an additional therapeutic agent is an entry inhibitor or fusion inhibitor. In certain embodiments, an additional therapeutic agent is an integrase inhibitor. In certain embodiments, an additional therapeutic agent is selected from efavirenz, etravirine, nevirapine, abacavir, emtricitabine, tenofovir, lamivudine, zidovudine, atazanavir, darunavir, fosamprenavir, ritonavir, enfuvirtide, maraviroc, and raltegravir.

Any of the methods provided herein may comprise administering a dose of the compound sufficient to reduce HCV RNA level. In certain embodiments, the administered dose of the compound reduces HCV RNA level below 40 copies per ml of serum. In certain embodiments, the administered dose of the compound achieves at least a 2-log reduction in HCV RNA level. In certain embodiments, administering a compound provided herein achieves a sustained virological response. In certain embodiments, the administered dose of the compound is sufficient to achieve an HCV RNA level reduction of at least 0.5 fold, at least 1.0 fold, at least 1.5 fold, at least 2.0 fold, or at least 2.5 fold. In certain embodiments, the HCV RNA level reduction is achieved after two weeks, three weeks, four weeks, five weeks, or six weeks of a first administration of the compound. In certain embodiments, a compound provided herein is administered once per week, once per two weeks, once per three weeks, once per four weeks, or once per month. In certain embodiments, a compound provided herein is administered once per two months or once per three months. In some embodiments, a compound provided herein is administered once per four weeks.

In certain embodiments, the dose of the compound administered is less than or equal to 5 mg/kg per week, less than or equal to 5 mg/kg, less than or equal to 4.5 mg/kg, less than or equal to 4.0 mg/kg, less than or equal to 3.5 mg/kg, less than or equal to 3.0 mg/kg, less than or equal to 2.5 mg/kg, less than or equal to 2.0 mg/kg, less than or equal to 1.5 mg/kg, or less than or equal to 1.0 mg/kg. In certain embodiments, the compound is administered at a dose within a range of 1 to 5 mg/kg, or 1 to 4 mg/kg, or 2 to 5 mg/kg, or 2 to 4 mg/kg. In certain embodiments, the dose of the compound administered is less than or equal to 10 mg/kg, less than or equal to 7.5 mg/kg, less than or equal to 10 mg/kg per week, or less than or equal to 7.5 mg/kg per week.

In certain embodiments, administration of a compound provided herein normalizes liver enzyme levels, wherein the liver enzyme is optionally alanine aminotransferase.

In any of the embodiments provided herein, the compound is present in a pharmaceutical composition.

Provided herein are compounds for use in treating an HCV-infected subject.

In certain embodiments, a subject is a human.

DETAILED DESCRIPTION

Figure 1A:
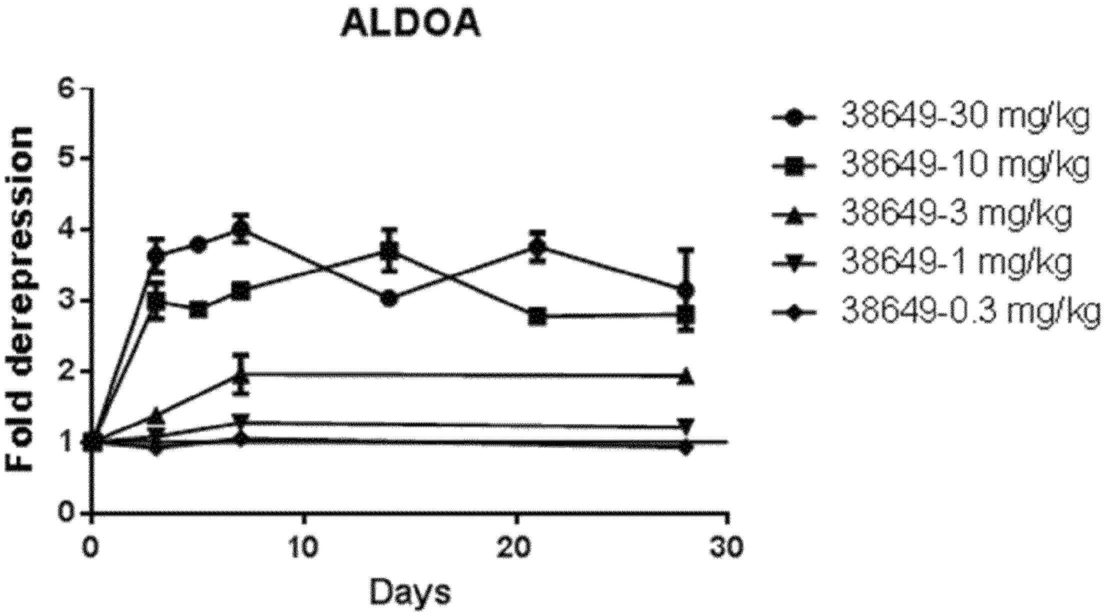
FIGS. 1A and 1B. In vivo potency of anti-miR-122 modified oligonucleotides. (A) Onset and duration of action of anti-miR-122, following a single administration of compound at the indicated doses. (B) De-repression of ALDOA seven days after a single dose of anti-miR-122 compound at the indicated doses.

Unless defined otherwise, all technical and scientific terms used herein have the same meaning as is commonly understood by one of skill in the arts to which the invention belongs. Unless specific definitions are provided, the nomenclature utilized in connection with, and the procedures and techniques of, analytical chemistry, synthetic organic chemistry, and medicinal and pharmaceutical chemistry described herein are those well known and commonly used in the art. In the event that there is a plurality of definitions for terms herein, those in this section prevail. Standard techniques may be used for chemical synthesis, chemical analysis, pharmaceutical preparation, formulation and delivery, and treatment of subjects. Certain such techniques and procedures may be found for example in “Carbohydrate Modifications in Antisense Research” Edited by Sangvi and Cook, American Chemical Society, Washington D.C., 1994; and “Remington’s Pharmaceutical Sciences,” Mack Publishing Co., Easton, Pa., 18th edition, 1990; and which is hereby incorporated by reference for any purpose. Where permitted, all patents, patent applications, published applications and publications, GENBANK sequences, websites and other published materials referred to throughout the entire disclosure herein, unless noted otherwise, are incorporated by reference in their entirety. Where reference is made to a URL or other such identifier or address, it is understood that such identifiers can change and particular information on the internet can change, but equivalent information can be found by searching the internet. Reference thereto evidences the availability and public dissemination of such information.

Before the present compositions and methods are disclosed and described, it is to be understood that the terminology used herein is for the purpose of describing particular embodiments only and is not intended to be limiting. It must be noted that, as used in the specification and the appended claims, the singular forms “a,” “an” and “the” include plural referents unless the context clearly dictates otherwise.

DEFINITIONS

“HCV infection” means infection with one or more genotypes of the Hepatitis C Virus.

“HCV-infected subject” means a subject who has been infected with one or more genotypes of the hepatitis C virus. An HCV-infected subject may or may not exhibit symptoms of HCV infection. HCV-infected subjects include subjects who have been infected with one or more genotypes of HCV, but HCV RNA in the blood of the subject is below detectable levels.

“HCV-associated disease” means a pathological process that is mediated by HCV infection. HCV-associated diseases include, but are not limited to, cirrhosis, liver fibrosis, steatoheptatitis, and hepatocellular carcinoma.

“Blood HCV RNA” means hepatitis C virus RNA present in the blood of an HCV-infected subject. Blood includes whole blood and serum.

“Rebound in serum HCV RNA” means an increase in HCV RNA level following a previous decrease in HCV RNA level.

“HCV RNA level” means the amount of HCV RNA in a given volume of the blood of a subject. HCV RNA level may be expressed as copies of RNA per milliliter. “HCV RNA level” may also be called “HCV viral load” or “HCV RNA titer.”

“Sustained virological response” means undetectable hepatitis C virus RNA in the blood of the subject at the end of an entire course of treatment and after a further six months. In certain embodiments, HCV RNA is considered undetectable below 40 copies per milliliter of blood.

“Non-responder” means a subject who has received treatment but is not experiencing a clinically acceptable improvement in disease markers or symptoms.

“Interferon non-responder” means an HCV-infected subject who has received treatment with interferon, but is not experiencing a clinically acceptable reduction in HCV RNA level.

“Direct-acting anti-viral agent” means a pharmaceutical agent that inhibits the activity of an HCV enzyme.

“Direct-acting anti-viral non-responder” means an HCV-infected subject who has received treatment with a direct-acting anti-viral agent, but is not experiencing a clinically acceptable reduction in HCV RNA level. In certain embodiments, the virus has developed resistance to the direct-acting anti-viral agent.

“miR-122-associated condition” means any disease, disorder or condition that can be treated, prevented or ameliorated by modulating miR-122. A miR-122-associated disease need not be characterized by excess miR-122. miR-122-associated diseases included, without limitation, HCV infection, elevated cholesterol, and iron overload disorders.

"Iron overload disorder" means any disease, disorder or condition characterized by excess iron in the body. "Subject" means a human or non-human animal selected for treatment or therapy.

"Subject in need thereof" means a subject that is identified as in need of a therapy or treatment.

"Subject suspected of having" means a subject exhibiting one or more clinical indicators of a disease.

"Administering" means providing a pharmaceutical agent or composition to a subject, and includes, but is not limited to, administering by a medical professional and self-administering.

"Parenteral administration" means administration through injection or infusion. Parenteral administration includes, but is not limited to, subcutaneous administration, intravenous administration, and intramuscular administration.

"Subcutaneous administration" means administration just below the skin.

"Intravenous administration" means administration into a vein.

"Administered concomitantly" refers to the co-administration of two or more agents to a subject in any manner in which the pharmacological effects of each agent are present in a subject. Concomitant administration does not require that both agents be administered in a single pharmaceutical composition, in the same dosage form, or by the same route of administration. The effects of both agents need not be present at the same time. The effects need only be overlapping for a period of time and need not be coextensive.

"Duration" means the period of time during which an activity or event continues. In certain embodiments, the duration of treatment is the period of time during which doses of a pharmaceutical agent or pharmaceutical composition are administered.

"Therapy" means a disease treatment method. In certain embodiments, therapy includes, but is not limited to, chemotherapy, radiation therapy, or administration of a pharmaceutical agent.

"Treatment" means the application of one or more specific procedures used for the cure or amelioration of a disease. In certain embodiments, the specific procedure is the administration of one or more pharmaceutical agents.

"Amelioration" means a lessening of severity of at least one indicator of a condition or disease. In certain embodiments, amelioration includes a delay or slowing in the progression of one or more indicators of a condition or disease. The severity of indicators may be determined by subjective or objective measures which are known to those skilled in the art.

"At risk for developing" means the state in which a subject is predisposed to developing a condition or disease. In certain embodiments, a subject at risk for developing a condition or disease exhibits one or more symptoms of the condition or disease, but does not exhibit a sufficient number of symptoms to be diagnosed with the condition or disease. In certain embodiments, a subject at risk for developing a condition or disease exhibits one or more symptoms of the condition or disease, but to a lesser extent required to be diagnosed with the condition or disease.

"Prevent the onset of" means to prevent the development of a condition or disease in a subject who is at risk for developing the disease or condition. In certain embodiments, a subject at risk for developing the disease or condition receives treatment similar to the treatment received by a subject who already has the disease or condition.

"Delay the onset of" means to delay the development of a condition or disease in a subject who is at risk for developing the disease or condition. In certain embodiments, a subject at risk for developing the disease or condition receives treatment similar to the treatment received by a subject who already has the disease or condition.

"Therapeutic agent" means a pharmaceutical agent used for the cure, amelioration or prevention of a disease.

"Dose" means a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual. In certain embodiments, a dose is administered as a slow infusion.

"Dosage unit" means a form in which a pharmaceutical agent is provided. In certain embodiments, a dosage unit is a vial containing lyophilized oligonucleotide. In certain embodiments, a dosage unit is a vial containing reconstituted oligonucleotide.

"Therapeutically effective amount" refers to an amount of a pharmaceutical agent that provides a therapeutic benefit to an animal.

"Pharmaceutical composition" means a mixture of substances suitable for administering to an individual that includes a pharmaceutical agent. For example, a pharmaceutical composition may comprise a sterile aqueous solution.

"Pharmaceutical agent" means a substance that provides a therapeutic effect when administered to a subject.

"Active pharmaceutical ingredient" means the substance in a pharmaceutical composition that provides a desired effect.

"Improved organ function" means a change in organ function toward normal limits. In certain embodiments, organ function is assessed by measuring molecules found in a subject's blood or urine. For example, in certain embodiments, improved liver function is measured by a reduction in blood liver transaminase levels. In certain embodiments, improved kidney function is measured by a reduction in blood urea nitrogen, a reduction in proteinuria, a reduction in albuminuria, etc.

"Acceptable safety profile" means a pattern of side effects that is within clinically acceptable limits.

"Side effect" means a physiological response attributable to a treatment other than desired effects. In certain embodiments, side effects include, without limitation, injection site reactions, liver function test abnormalities, renal function abnormalities, liver toxicity, renal toxicity, central nervous system abnormalities, and myopathies. Such side effects may be detected directly or indirectly. For example, increased aminotransferase levels in serum may indicate liver toxicity or liver function abnormality. For example, increased bilirubin may indicate liver toxicity or liver function abnormality.

"Injection site reaction" means inflammation or abnormal redness of skin at a site of injection in an individual.

"Subject compliance" means adherence to a recommended or prescribed therapy by a subject.

"Comply" means the adherence with a recommended therapy by a subject.

"Recommended therapy" means a treatment recommended by a medical professional to treat, ameliorate, delay, or prevent a disease.

"miR-122" means a microRNA having the nucleobase sequence (SEQ ID NO: 1)
UGGAGUGUGACAAUGGUGUUUG.

"miR-122 stem-loop" means the microRNA precursor having the nucleobase sequence (SEQ ID NO: 2)
CCUUAGCAGAGCUGUGGAGUGUGACAAUGGUGUUUGUGUCUAAACUAUCA

AACGCCAUUAUCACACUAAAUAGCUACUGCUAGGC.

"Anti-miR" means an oligonucleotide having a nucleobase sequence complementary to a microRNA. In certain embodiments, an anti-miR is a modified oligonucleotide.

"Anti-miR-122" means an oligonucleotide having a nucleobase sequence complementary to miR-122. In certain embodiments, an anti-miR-122 is fully complementary to miR-122 (i.e., 100% complementary). In certain embodiments, an anti-miR-122 is at least 90%, at least 93%, at least 94%, at least 95%, or 100% complementary. In certain embodiments, an anti-miR-122 is a modified oligonucleotide.

"Target nucleic acid" means a nucleic acid to which an oligomeric compound is designed to hybridize.

"Targeting" means the process of design and selection of nucleobase sequence that will hybridize to a target nucleic acid.

"Targeted to" means having a nucleobase sequence that will allow hybridization to a target nucleic acid.

"Modulation" means a perturbation of function, amount, or activity. In certain embodiments, modulation means an increase in function, amount, or activity. In certain embodiments, modulation means a decrease in function, amount, or activity.

"Expression" means any functions and steps by which a gene's coded information is converted into structures present and operating in a cell.

"5' target site" means the nucleobase of a target nucleic acid which is complementary to the 3'-most nucleobase of a particular oligonucleotide.

"3' target site" means the nucleobase of a target nucleic acid which is complementary to the 5'-most nucleobase of a particular oligonucleotide.

"Region" means a portion of linked nucleosides within a nucleic acid. In certain embodiments, an oligonucleotide has a nucleobase sequence that is complementary to a region of a target nucleic acid. For example, in certain such embodiments an oligonucleotide is complementary to a region of a microRNA sequence. In certain such embodiments, an oligonucleotide is fully complementary to a region of a microRNA.

"Segment" means a smaller or sub-portion of a region.

"Nucleobase sequence" means the order of contiguous nucleobases in an oligomeric compound or nucleic acid, typically listed in a 5' to 3' orientation, independent of any sugar, linkage, and/or nucleobase modification.

"Contiguous nucleobases" means nucleobases immediately adjacent to each other in a nucleic acid.

"Nucleobase complementarity" means the ability of two nucleobases to pair non-covalently via hydrogen bonding.

"Complementary" means that one nucleic acid is capable of hybridizing to another nucleic acid or oligonucleotide. In certain embodiments, complementary refers to an oligonucleotide capable of hybridizing to a target nucleic acid.

"Fully complementary" means each nucleobase of an oligonucleotide is capable of pairing with a nucleobase at each corresponding position in a target nucleic acid. In certain embodiments, an oligonucleotide is fully complementary to a microRNA, i.e. each nucleobase of the oligonucleotide is complementary to a nucleobase at a corresponding position in the microRNA. In certain embodiments, an oligonucleotide wherein each nucleobase has complementarity to a nucleobase within a region of a microRNA sequence is fully complementary to the microRNA sequence.

"Percent complementarity" means the percentage of nucleobases of an oligonucleotide that are complementary to an equal-length portion of a target nucleic acid. Percent complementarity is calculated by dividing the number of nucleobases of the oligonucleotide that are complementary to nucleobases at corresponding positions in the target nucleic acid by the total number of nucleobases in the oligonucleotide.

"Percent identity" means the number of nucleobases in a first nucleic acid that are identical to nucleobases at corresponding positions in a second nucleic acid, divided by the total number of nucleobases in the first nucleic acid. In certain embodiments, the first nucleic acid is a microRNA and the second nucleic acid is a microRNA. In certain embodiments, the first nucleic acid is an oligonucleotide and the second nucleic acid is an oligonucleotide.

"Hybridize" means the annealing of complementary nucleic acids that occurs through nucleobase complementarity.

"Mismatch" means a nucleobase of a first nucleic acid that is not capable of Watson-Crick pairing with a nucleobase at a corresponding position of a second nucleic acid.

"Identical" in the context of nucleobase sequences, means having the same nucleobase sequence, independent of sugar, linkage, and/or nucleobase modifications and independent of the methyl state of any pyrimidines present.

"MicroRNA" means an endogenous non-coding RNA between 18 and 25 nucleobases in length, which is the product of cleavage of a pre-microRNA by the enzyme Dicer. Examples of mature microRNAs are found in the microRNA database known as miRBase (http://microrna.sanger.ac.uk/). In certain embodiments, microRNA is abbreviated as "microRNA" or "miR."

"Pre-microRNA" or "pre-miR" means a non-coding RNA having a hairpin structure, which is the product of cleavage of a pri-miR by the double-stranded RNA-specific ribonuclease known as Drosha.

"Stem-loop sequence" means an RNA having a hairpin structure and containing a mature microRNA sequence. Pre-microRNA sequences and stem-loop sequences may overlap. Examples of stem-loop sequences are found in the microRNA database known as miRBase (http://microrna.sanger.ac.uk/).

"Pri-microRNA" or "pri-miR" means a non-coding RNA having a hairpin structure that is a substrate for the double-stranded RNA-specific ribonuclease Drosha.

"microRNA precursor" means a transcript that originates from a genomic DNA and that comprises a non-coding, structured RNA comprising one or more microRNA sequences. For example, in certain embodiments a microRNA precursor is a pre-microRNA. In certain embodiments, a microRNA precursor is a pri-microRNA.

"microRNA-regulated transcript" means a transcript that is regulated by a microRNA.

"Monocistronic transcript" means a microRNA precursor containing a single microRNA sequence.

"Polycistronic transcript" means a microRNA precursor containing two or more microRNA sequences.

"Seed sequence" means a nucleobase sequence comprising from 6 to 8 contiguous nucleobases of nucleobases 1 to 9 of the 5'-end of a mature microRNA sequence.

"Seed match sequence" means a nucleobase sequence that is complementary to a seed sequence, and is the same length as the seed sequence.

"Oligomeric compound" means a compound that comprises a plurality of linked monomeric subunits. Oligomeric compounds included oligonucleotides.

"Oligonucleotide" means a compound comprising a plurality of linked nucleosides, each of which can be modified or unmodified, independent from one another.

"Naturally occurring internucleoside linkage" means a 3' to 5' phosphodiester linkage between nucleosides.

"Natural sugar" means a sugar found in DNA (2'-H) or RNA (2'-OH).

"Internucleoside linkage" means a covalent linkage between adjacent nucleosides.

"Linked nucleosides" means nucleosides joined by a covalent linkage.

"Nucleobase" means a heterocyclic moiety capable of non-covalently pairing with another nucleobase.

"Nucleoside" means a nucleobase linked to a sugar moiety.

"Nucleotide" means a nucleoside having a phosphate group covalently linked to the sugar portion of a nucleoside.

"Compound comprising a modified oligonucleotide consisting of" a number of linked nucleosides means a compound that includes a modified oligonucleotide having the specified number of linked nucleosides. Thus, the compound may include additional substituents or conjugates. Unless otherwise indicated, the compound does not include any additional nucleosides beyond those of the modified oligonucleotide.

"Modified oligonucleotide" means an oligonucleotide having one or more modifications relative to a naturally occurring terminus, sugar, nucleobase, and/or internucleoside linkage. A modified oligonucleotide may comprise unmodified nucleosides.

"Single-stranded modified oligonucleotide" means a modified oligonucleotide which is not hybridized to a complementary strand.

"Modified nucleoside" means a nucleoside having any change from a naturally occurring nucleoside. A modified nucleoside may have a modified sugar, and an unmodified nucleobase. A modified nucleoside may have a modified sugar and a modified nucleobase. A modified nucleoside may have a natural sugar and a modified nucleobase. In certain embodiments, a modified nucleoside is a bicyclic nucleoside. In certain embodiments, a modified nucleoside is a non-bicyclic nucleoside.

"2'-modified nucleoside" means a nucleoside comprising a sugar with any modification at the position equivalent to the 2' position of the furanosyl ring as the positions are numbered in 2-deoxyribose or ribose. It is to be understood that 2'-modified nucleosides include, without limitation, nucleosides comprising bicyclic sugar moieties.

"Modified internucleoside linkage" means any change from a naturally occurring internucleoside linkage.

"Phosphorothioate internucleoside linkage" means a linkage between nucleosides where one of the non-bridging atoms is a sulfur atom. A "phosphorothioate linkage" means a linkage between two chemical moieties having the same structure as a phosphorothioate internucleoside linkage, e.g., —OP(O)(S)O—.

A "phosphodiester linkage" means a linkage between two chemical moieties having the same structure as a phosphodiester internucleoside linkage, e.g., $—OP(O)_2O—$.

"Unmodified nucleobase" means the naturally occurring heterocyclic bases of RNA or DNA: the purine bases adenine (A) and guanine (G), and the pyrimidine bases thymine (T), cytosine (C) (including 5-methylcytosine), and uracil (U).

"5-methylcytosine" means a cytosine comprising a methyl group attached to the 5 position.

"Non-methylated cytosine" means a cytosine that does not have a methyl group attached to the 5 position.

"Modified nucleobase" means any nucleobase that is not an unmodified nucleobase.

"Furanosyl" means a structure comprising a 5-membered ring consisting of four carbon atoms and one oxygen atom.

"Naturally occurring furanosyl" means a ribofuranosyl as found in naturally occurring RNA or a deoxyribofuranosyl as found in naturally occurring DNA.

"Sugar moiety" means a naturally occurring furanosyl or a modified sugar moiety.

"Modified sugar moiety" means a substituted sugar moiety or a sugar surrogate.

"Substituted sugar moiety" means a furanosyl that is not a naturally occurring furanosyl. Substituted sugar moieties include, but are not limited to sugar moieties comprising modifications at the 2'-position, the 5'-position and/or the 4'-position of a naturally occurring furanosyl. Certain substituted sugar moieties are bicyclic sugar moieties.

"Sugar surrogate" means a structure that does not comprise a furanosyl and that is capable of replacing the naturally occurring furanosyl of a nucleoside, such that the resulting nucleoside is capable of (1) incorporation into an oligonucleotide and (2) hybridization to a complementary nucleoside. Such structures include relatively simple changes to the furanosyl, such as rings comprising a different number of atoms (e.g., 4, 6, or 7-membered rings); replacement of the oxygen of the furanosyl with a non-oxygen atom (e.g., carbon, sulfur, or nitrogen); or both a change in the number of atoms and a replacement of the oxygen. Such structures may also comprise substitutions corresponding with those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholinos, cyclohexenyls and cyclohexitols.

"β-D-deoxyribose" means a naturally occurring DNA sugar moiety.

"β-D-ribose" means a naturally occurring RNA sugar moiety.

"2'-O-methyl sugar" or "2'-OMe sugar" means a sugar having a O-methyl modification at the 2' position.

"2'-O-methoxyethyl sugar" or "2'-MOE sugar" means a sugar having a O-methoxyethyl modification at the 2' position.

"2'-O-fluoro" or "2'-F" means a sugar having a fluoro modification of the 2' position.

"Bicyclic sugar moiety" means a modified sugar moiety comprising a 4 to 7 membered ring (including by not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl. Nonlimiting exemplary bicyclic sugar moieties include LNA, ENA, cEt, S-cEt, and R-cEt.

"Locked nucleic acid (LNA) sugar moiety" means a substituted sugar moiety comprising a $(CH_2)$—O bridge between the 4' and 2' furanose ring atoms.

"ENA sugar moiety" means a substituted sugar moiety comprising a $(CH_2)_2$—O bridge between the 4' and 2' furanose ring atoms.

"Constrained ethyl (cEt) sugar moiety" means a substituted sugar moiety comprising a $CH(CH_3)$—O bridge between the 4' and the 2' furanose ring atoms. In certain embodiments, the $CH(CH_3)$—O bridge is constrained in the S orientation. In certain embodiments, the $CH(CH_3)$—O bridge is constrained in the R orientation.

"S-cEt sugar moiety" means a substituted sugar moiety comprising an S-constrained $CH(CH_3)$—O bridge between the 4' and the 2' furanose ring atoms.

"R-cEt sugar moiety" means a substituted sugar moiety comprising an R-constrained $CH(CH_3)$—O bridge between the 4' and the 2' furanose ring atoms.

"2'-O-methyl nucleoside" means a modified nucleoside having a 2'-O-methyl sugar modification.

"2'-O-methoxyethyl nucleoside" means a modified nucleoside having a 2'-O-methoxyethyl sugar modification. A 2'-O-methoxyethyl nucleoside may comprise a modified or unmodified nucleobase.

"2'-fluoro nucleoside" means a modified nucleoside having a 2'-fluoro sugar modification. A 2'-fluoro nucleoside may comprise a modified or unmodified nucleobase.

"Bicyclic nucleoside" means a modified nucleoside having a bicyclic sugar moiety. A bicyclic nucleoside may have a modified or unmodified nucleobase.

"cEt nucleoside" means a nucleoside comprising a cEt sugar moiety. A cEt nucleoside may comprise a modified or unmodified nucleobase.

"S-cEt nucleoside" means a nucleoside comprising an S-cEt sugar moiety.

"R-cEt nucleoside" means a nucleoside comprising an R-cEt sugar moiety.

"Non-bicyclic nucleoside" means a nucleoside that has a sugar other than a bicyclic sugar. In certain embodiments, a non-bicyclic nucleoside comprises a naturally occurring sugar. In certain embodiments, a non-bicyclic nucleoside comprises a modified sugar. In certain embodiments, a non-bicyclic nucleoside is a β-D-deoxyribonucleoside. In certain embodiments, a non-bicyclic nucleoside is a 2'-O-methoxyethyl nucleoside.

"β-D-deoxyribonucleoside" means a naturally occurring DNA nucleoside.

"β-D-ribonucleoside" means a naturally occurring RNA nucleoside.

"LNA nucleoside" means a nucleoside comprising a LNA sugar moiety.

"ENA nucleoside" means a nucleoside comprising an ENA sugar moiety.

"Motif" means a pattern of modified and/or unmodified nucleobases, sugars, and/or internucleoside linkages in an oligonucleotide. In certain embodiments, a motif is a nucleoside pattern.

"Nucleoside pattern" means a pattern of nucleoside modifications in a modified oligonucleotide or a region thereof. A nucleoside pattern is a motif that describes the arrangement of nucleoside modifications in an oligonucleotide.

"Fully modified oligonucleotide" means each nucleobase, each sugar, and/or each internucleoside linkage is modified.

"Uniformly modified oligonucleotide" means each nucleobase, each sugar, and/or each internucleoside linkage has the same modification throughout the modified oligonucleotide.

"Stabilizing modification" means a modification to a nucleoside that provides enhanced stability to a modified oligonucleotide, in the presence of nucleases, relative to that provided by 2'-deoxynucleosides linked by phosphodiester internucleoside linkages. For example, in certain embodiments, a stabilizing modification is a stabilizing nucleoside modification. In certain embodiments, a stabilizing modification is an internucleoside linkage modification.

"Stabilizing nucleoside" means a nucleoside modified to provide enhanced nuclease stability to an oligonucleotide, relative to that provided by a 2'-deoxynucleoside. In one embodiment, a stabilizing nucleoside is a 2'-modified nucleoside.

"Stabilizing internucleoside linkage" means an internucleoside linkage that provides improved nuclease stability to an oligonucleotide relative to that provided by a phosphodiester internucleoside linkage. In one embodiment, a stabilizing internucleoside linkage is a phosphorothioate internucleoside linkage.

A "linking group" as used herein refers to an atom or group of atoms that attach a first chemical entity to a second chemical entity via one or more covalent bonds.

A "linker" as used herein, refers to an atom or group of atoms that attach one or more ligands to a modified or unmodified nucleoside via one or more covalent bonds. The modified or unmodified nucleoside may be part of a modified oligonucleotide as described herein, or may be attached to a modified oligonucleotide through a phosphodiester or phosphorothioate bond. In some embodiments, the linker attaches one or more ligands to the 3' end of a modified oligonucleotide. In some embodiments, the linker attaches one or more ligands to the 5' end of a modified oligonucleotide. In some embodiments, the linker attaches one or more ligands to a modified or unmodified nucleoside that is attached to the 3' end of a modified oligonucleotide. In some embodiments, the linker attaches one or more ligands to a modified or unmodified nucleoside that is attached to the 5' end of a modified oligonucleotide. When the linker attaches one or more ligands to the 3' end of a modified oligonucleotide or to a modified or unmodified nucleoside attached to the 3' end of a modified oligonucleotide, in some embodiments, the attachment point for the linker may be the 3' carbon of a modified or unmodified sugar moiety. When the linker attaches one or more ligands to the 5' end of a modified oligonucleotide or to a modified or unmodified nucleoside attached to the 5' end of a modified oligonucleotide, in some embodiments, the attachment point for the linker may be the 5' carbon of a modified or unmodified sugar moiety.

Overview

To identify potent inhibitors of miR-122, numerous anti-miR-122 compounds were designed and synthesized. The compounds comprised modified oligonucleotides that varied in length, and in the number, placement, and identity of bicyclic nucleosides and non-bicyclic nucleosides. An initial series of compounds was tested in an in vitro luciferase assay, which identified a subset of compounds as in vitro active compounds. These in vitro active compounds were then tested in in vivo assays to identify those compounds that are potent inhibitors of miR-122 in vivo. From the initial in vitro and in vivo screens, certain compounds were selected as the basis for the design of additional compounds. The experimentally observed correlations between structure and activity (both in vitro and in vivo) were used to inform the design of these additional compounds, with further variations in length and selection and arrangement of bicyclic and non-bicyclic nucleosides. The in vitro and in vivo screening assays were repeated for these additional compounds. Certain compounds were also tested for other properties, for example, susceptibility to exonuclease activity, tissue accumulation, and tissue half-life.

Of over 400 compounds screened in vitro during this process, approximately 150 were identified as active in an in vitro luciferase assay. Approximately 70 of these compounds were further evaluated for in vivo potency and safety. Through this iterative process of designing and screening compounds, it was observed that certain compounds, both unconjugated anti-miR-122 modified oligonucleotides and conjugated anti-miR-122 modified oligonucleotides, were potent inhibitors of miR-122 in vivo. As such, these compounds are useful for the modulation of cellular processes that are promoted by the activity of miR-122. Further, such compounds are useful for treating, preventing, and/or delaying the onset of diseases associated with miR-122. Such diseases include, but are not limited to, HCV infection and HCV-related complications, such as cirrhosis, liver fibrosis, steatohepatitis, steatosis, and hepatocellular carcinoma.

Certain Anti-miR-122 Compounds

Provided herein are modified oligonucleotides having certain patterns of bicyclic and non-bicyclic nucleosides. Modified oligonucleotides having the patterns identified herein are effective inhibitors of miR-122 activity.

Each of the nucleoside patterns illustrated herein is shown in the 5' to 3' orientation.

In certain embodiments, provided herein are compounds comprising a modified oligonucleotide consisting of from 16 to 22 linked nucleosides, wherein the nucleobase sequence of the modified oligonucleotide is complementary to miR-122 (SEQ ID NO: 1) and wherein the modified oligonucleotide comprises at least 16 contiguous nucleosides of the following nucleoside pattern I in the 5' to 3' orientation:

$$(R)_X—N^Q—N^Q—N^B—N^B—N^Q—N^B—N^Q—N^B—N^Q—N^B—N^B—(N^Z)_Y$$

wherein each R is, independently, a non-bicyclic nucleoside or a bicyclic nucleoside;

X is from 4 to 10;

each $N^B$ is, independently, a bicyclic nucleoside;

each $N^Q$ is, independently, a non-bicyclic nucleoside;

Y is 0 or 1; and $N^Z$ is a modified nucleoside or an unmodified nucleoside non-bicyclic nucleoside or a bicyclic nucleoside.

In certain embodiments, the modified oligonucleotide comprises at least 16, at least 17, at least 18, at least 19, at least 20, at least 21, or 22 contiguous nucleosides of nucleoside pattern I.

In certain embodiments, each bicyclic nucleoside is independently selected from an LNA nucleoside, a cEt nucleoside, and an ENA nucleoside.

In certain embodiments, at least two bicyclic nucleosides are different from one another.

In certain embodiments, all bicyclic nucleosides have the same type of sugar moiety.

In certain embodiments, each bicyclic nucleoside is a cEt nucleoside. In certain embodiments, the cEt nucleoside is an S-cEt nucleoside. In certain embodiments, the cEt nucleoside is an R-cEt nucleoside.

In certain embodiments, each bicyclic nucleoside is an LNA nucleoside.

In certain embodiments, at least two non-bicyclic nucleosides comprise sugar moieties that are different from one another. In certain embodiments, each non-bicyclic nucleoside has the same type of sugar moiety.

In certain embodiments, each non-bicyclic nucleoside is independently selected from a β-D-deoxyribonucleoside, a β-D-ribonucleoside, 2'-O-methyl nucleoside, a 2'-O-methoxyethyl nucleoside, and a 2'-fluoronucleoside. In certain embodiments, each non-bicyclic nucleoside is independently selected from a β-D-deoxyribonucleoside, and a 2'-O-methoxyethyl nucleoside. In certain embodiments, each non-bicyclic nucleoside is a β-D-deoxyribonucleoside. In certain embodiments, each non-bicyclic nucleoside is a 2'-MOE nucleoside.

In certain embodiments, no more than two non-bicyclic nucleosides are 2'-MOE nucleosides. In certain embodiments, no more than two non-bicyclic nucleosides are 2'-MOE nucleosides, and each other non-bicyclic nucleoside is a β-D-deoxyribonucleoside.

In certain embodiments, the 5'-terminal and the 3'-terminal non-bicyclic nucleosides are 2'-MOE nucleosides and each other non-bicyclic nucleoside is a β-D-deoxyribonucleoside.

In certain embodiments, two non-bicyclic nucleosides are 2'-MOE nucleosides and each other non-bicyclic nucleoside is a β-D-deoxyribonucleoside.

In certain embodiments, each nucleoside of R is a 2'-MOE nucleoside.

In certain embodiments, X is 4, 5, 6, 7, 8, 9, or 10.

In certain embodiments, Y is 0. In certain embodiments, Y is 1.

In certain embodiments, R consist of seven linked nucleosides, wherein each nucleoside is a 2'-O-methoxyethyl nucleoside; each $N^B$ is an S-cEt nucleoside; each $N^Q$ is a β-D-deoxyribonucleoside; and Y is O.

In certain embodiments, R consists of four linked nucleosides $N^{R1}—N^{R2}—N^{R3}—N^{R4}$ wherein each of $N^{R1}$ and $N^{R3}$ is a S-cEt nucleoside and each of $N^{R2}$ and $N^{R4}$ is a β-D-deoxyribonucleoside; each $N^B$ is an S-cEt nucleoside; each $N^Q$ is a β-D-deoxyribonucleoside; Y is 1; and $N^Z$ is a β-D-deoxyribonucleoside.

In certain embodiments, R consists of four linked nucleosides $N^{R1}—N^{R2}—N^{R3}—N^{R4}$ wherein each of $N^{R1}$ and $N^{R4}$ is a S-cEt nucleoside and each of $N^{R2}$ and $N^{R3}$ is a β-D-deoxyribonucleoside; each $N^B$ is an S-cEt nucleoside; each $N^Q$ is a β-D-deoxyribonucleoside; Y is 1; and $N^Z$ is a 2'-O-methoxyethyl nucleoside.

In certain embodiments, R consists of seven linked nucleosides $N^{R1}—N^{R2}—N^{R3}—N^{R4}—N^{R5}—N^{R6}—N^{R7}$, wherein each of $N^{R1}$, $N^{R2}$, $N^{R3}$, and $N^{R4}$ is a 2'-O-methoxyethyl nucleoside, each of $N^{R5}$ and $N^{R7}$ is a β-D-deoxyribonucleoside, and $N^{R6}$ is S-cEt nucleoside; each $N^B$ is an S-cEt nucleoside; each $N^Q$ is a β-D-deoxyribonucleoside; and Y is 0.

In certain embodiments, R consists of seven linked nucleosides $N^{R1}—N^{R2}—N^{R3}—N^{R4}—N^{R5}—N^{R6}—N^{R7}$, wherein each of $N^{R1}$, $N^{R2}$, $N^{R3}$, $N^{R4}$, and $N^{R5}$ is a 2'-O-methoxyethyl nucleoside, $N^{R6}$ is S-cEt nucleoside, and $N^{R7}$ is a β-D-deoxyribonucleoside; each $N^B$ is an S-cEt nucleoside; each $N^Q$ is a β-D-deoxyribonucleoside; and Y is 0.

In certain embodiments, R consists of seven linked nucleosides $N^{R1}—N^{R2}—N^{R3}—N^{R4}—N^{R5}—N^{R6}—N^{R7}$, wherein each of $N^{R1}$, $N^{R2}$, $N^{R3}$, $N^{R4}$, $N^{R5}$, and $N^{R6}$ is 2'-O-methoxyethyl nucleoside, and $N^{R7}$ is a β-D-deoxyribonucleoside; each $N^B$ is an S-cEt nucleoside; each $N^Q$ is a β-D-deoxyribonucleoside; and Y is 0.

In certain embodiments, R consists of ten linked nucleosides $N^{R1}—N^{R2}—N^{R3}—N^{R4}—N^{R5}—N^{R6}—N^{R7}—N^{R8}—N^{R9}—N^{R10}$, wherein each of $N^{R1}$, $N^{R2}$, $N^{R3}$, $N^{R4}$, $N^{R5}$, and $N^{R6}$ is 2'-O-methoxyethyl nucleoside, each of $N^{R7}$ and $N^{R9}$ is a an S-cEt nucleoside; each of $N^{R8}$ and $N^{R10}$ is a β-D-deoxyribonucleoside; each $N^B$ is an S-cEt nucleoside; each $N^Q$ is a β-D-deoxyribonucleoside; and Y is 0.

In certain embodiments, R consists of ten linked nucleosides $N^{R1}—N^{R2}—N^{R3}—N^{R4}—N^{R5}—N^{R6}—N^{R7}—N^{R8}—N^{R9}—N^{R10}$, wherein each of $N^{R1}$, $N^{R2}$, $N^{R3}$, $N^{R4}$, $N^{R5}$, and $N^{R6}$ is 2'-O-methoxyethyl nucleoside, each of $N^{R7}$ and $N^{R9}$ is a an S-cEt nucleoside; and each of $N^{R8}$ and $N^{R10}$ is a β-D- deoxyribonucleoside; each $N^B$ is an S-cEt nucleoside; each $N^Q$ is a β-D-deoxyribonucleoside; Y is 1 and $N_Z$ is a 2'-O-methoxyethyl nucleoside.

In certain embodiments, R consists of four linked nucleosides $N^{R1}$—$N^{R2}$—$N^{R3}$—$N^{R4}$ wherein each of $N^{R1}$ and $N^{R4}$ is an S-cEt nucleoside, and each of $N^{R1}$ and $N^{R3}$ is a β-D-deoxyribonucleoside; each $N^B$ is an S-cEt nucleoside; each $N^Q$ is a β-D-deoxyribonucleoside; Y is 1 and $N^Z$ is a β-D-deoxyribonucleoside.

In certain embodiments, R consists of four linked nucleosides $N^{R1}$—$N^{R2}$—$N^{R3}$—$N^{R4}$ wherein $N^{R1}$ is a 2'-O-methoxyethyl nucleoside, each of $N^{R2}$ and $N^{R4}$ is an S-cEt nucleoside, and $N^{R3}$ is a β-D-deoxyribonucleoside; each $N^B$ is an S-cEt nucleoside; each $N^Q$ is a β-D-deoxyribonucleoside; Y is 1 and $N^Z$ is a 2'-O-methoxyethyl nucleoside.

In certain embodiments, the nucleobase sequence of the modified oligonucleotide is at least 90%, at least 93%, at least 94%, at least 95%, or 100% complementary to the nucleobase sequence of miR-122 (SEQ ID NO: 1).

In certain embodiments, the nucleobase sequence of the modified oligonucleotide is complementary to miR-122 such that position 2 of SEQ ID NO: 1 is paired with the 3'-terminal nucleobase of the oligonucleotide. For example:

```
5'-UGGAGUGUGACAAUGGUGUUUG-3'         (miR-122; SEQ ID NO: 1)
    |||||||||||||||||
3'- CCTCACACTGTTACCACA-5'     (an anti-miR-122; SEQ ID NO: 4)
```

In certain embodiments, the nucleobase sequence of the modified oligonucleotide is complementary to miR-122 such that position 1 of SEQ ID NO: 1 is paired with the 3'-terminal nucleobase of the oligonucleotide. For example:

```
5'-UGGAGUGUGACAAUGGUGUUUG-3' (miR-122; SEQ ID NO: 1)
   ||||||||||||||||
3'-ACCTCACACTGTTACC-5'       (an anti-miR-122; SEQ ID NO: 3); and
5'-UGGAGUGUGACAAUGGUGUUUG-3' (miR-122; SEQ ID NO: 1)
   |||||||||||||||||||||
3'-TCCTCACACTGTTACCACAAAC-5' (an anti-miR-122; SEQ ID NO: 6)
```

In certain embodiments, at least one internucleoside linkage is a modified internucleoside linkage. In certain embodiments, each internucleoside linkage is a modified internucleoside linkage. In certain embodiments, a modified internucleoside linkage is a phosphorothioate internucleoside linkage.

In certain embodiments, at least one pyrimidine of the modified oligonucleotide comprises a 5-methyl group. In certain embodiments, at least one cytosine of the modified oligonucleotide is a 5-methylcytosine. In certain embodiments, each cytosine of the modified oligonucleotide is a 5-methylcytosine. In certain embodiments, each modified nucleotide that comprises a cytosine comprises a 5-methylcytosine. In certain embodiments, each 2'-O-methoxyethylnucleoside that comprises a cytosine comprises a 5-methylcytosine.

In certain embodiments, the nucleobase sequence of the modified oligonucleotide is selected from SEQ ID NOs: 3 to 6, wherein each T is independently selected from T and U.

In certain embodiments, the modified oligonucleotide has 0, 1, 2, or 3 mismatches with respect to the nucleobase sequence of miR-122. In certain embodiments, the modified oligonucleotide has 0 mismatches with respect to the nucleobase sequence of miR-122. In certain embodiments, the modified oligonucleotide has 1 mismatch with respect to the nucleobase sequence of miR-122. In certain embodiments, the modified oligonucleotide has 2 mismatches with respect to the nucleobase sequence of miR-122.

In certain embodiments, a modified oligonucleotide consists of greater than 22 linked nucleosides, and comprises at least 8 linked nucleosides of nucleoside pattern I. The nucleosides that are present in addition to the nucleosides described by nucleoside pattern I are either modified or unmodified.

In certain embodiments, a modified oligonucleotide consists of less than 16 linked nucleosides, and comprises at least 8 linked nucleosides of nucleoside pattern I.

In certain embodiments, a modified oligonucleotide has a nucleobase sequence and modifications as shown in Table 1. Nucleosides and nucleobases are indicated as follows: the superscript "Me" indicates 5-methylcytosine; nucleosides not followed by a subscript are β-D-deoxyribonucleosides; nucleosides followed by a subscript "E" are 2'-MOE nucleosides; nucleosides followed by a subscript "S" are S-cEt nucleosides; and each internucleoside linkage is a phosphorothioate internucleoside linkage.

TABLE 1

Anti-miR-122 Compounds

| Compound # | Sequence and Modifications | SEQ ID NO |
|---|---|---|
| 38649 | $A_E{}^{Me}C_EA_E{}^{Me}C_E{}^{Me}C_EA_ET_ETGU_SC_SAC_SAC_STC_SC_S$ | 4 |
| 38012 | $C_SCA_STTGU_SC_SAC_SAC_STC_SC_SA$ | 3 |
| 38016 | ${}^{Me}C_SCAT_STGT_S{}^{Me}C_SA{}^{Me}C_SA{}^{Me}C_ST{}^{Me}C_S{}^{Me}C_SA_E$ | 3 |
| 38646 | $A_E{}^{Me}C_EA_E{}^{Me}C_ECA_STTGU_SC_SAC_SAC_STC_SC_S$ | 4 |
| 38647 | $A_E{}^{Me}C_EA_E{}^{Me}C_E{}^{Me}C_EA_STTGU_SC_SAC_SAC_STC_SC_S$ | 4 |
| 38648 | $A_E{}^{Me}C_EA_E{}^{Me}C_E{}^{Me}C_EA_ETTGU_SC_SAC_SAC_STC_SC_S$ | 4 |
| 38652 | ${}^{Me}C_EA_EA_EA_E{}^{Me}C_EA_EC_SCA_STTGU_SC_SAC_SAC_STC_SC_S$ | 5 |
| 38659 | $C_SCA_STTGU_SC_SAC_SAC_STC_SC_ST_E$ | 10 |

TABLE 1-continued

| Anti-miR-122 Compounds | | |
|---|---|---|
| Compound # | Sequence and Modifications | SEQ ID NO |
| 38660 | $^{Me}C_EA_EA_EA_E{}^{Me}C_EA_EC_SCA_STTGU_SC_S$ $AC_SAC_STC_SC_ST_E$ | 6 |
| 38872 | $C_SCAU_STGU_SC_SAC_SAC_STC_SC_SA$ | 3 |
| 38910 | $^{Me}C_EC_SAU_STGU_SC_SAC_SAC_STC_SC_SA_E$ | 3 |

In some embodiments, a modified oligonucleotide has a nucleobase sequence and modifications as shown below:

(SEQ ID NO: 8)
$U_STGU_SC_SAC_SAC_STC_SC_SA_S$;

or (SEQ ID NO: 9)
$C_SA_SC_SA_SC_SU_SC_SC_S$;

wherein nucleosides not followed by a subscript are β-D-deoxyribonucleosides; nucleosides followed by a subscript "S" are S-cEt nucleosides; and each internucleoside linkage is a phosphorothioate internucleoside linkage. In some such embodiments, a compound is 38591, 38633, 38998, or 38634.

Anti-miR-122 Compounds Comprising Conjugates

In certain embodiments, a compound provided herein comprises a modified oligonucleotide conjugated to one or more moieties which enhance the activity, cellular distribution and/or cellular uptake of the oligonucleotide. For example, increased cellular uptake of compounds may be achieved by utilizing conjugates that are ligands for cell-surface receptors. The binding of a ligand conjugated to an exogenous molecule (e.g., a drug) to its cell surface receptor leads to the internalization of the conjugated molecule, thereby enhancing transmembrane transport of the exogenous molecule. Any of the anti-miR-122 modified oligonucleotides provided herein may be linked to one or more moieties to form a compound comprising a conjugated anti-miR-122 modified oligonucleotide.

In certain embodiments, a compound provided herein comprises a conjugate moiety linked to the 5' terminus or the 3' terminus of the modified oligonucleotide. In certain embodiments, the compound comprises a conjugate moiety linked to the 3' terminus of the modified oligonucleotide. In certain embodiments, the compound comprises a conjugate moiety linked to the 5' terminus of the modified oligonucleotide. In certain embodiments, the compound comprises a first conjugate moiety linked to the 3' terminus of the modified oligonucleotide and a second conjugate moiety linked to the 5' terminus of the modified oligonucleotide.

In certain embodiments, a conjugate moiety comprises at least one ligand selected from a carbohydrate, cholesterol, a lipid, a phospholipid, an antibody, a lipoprotein, a hormone, a peptide, a vitamin, a steroid, or a cationic lipid.

Ligands may be covalently attached to a modified oligonucleotide by any suitable linker. Various linkers are known in the art, and certain nonlimiting exemplary linkers are described, e.g., in PCT Publication No. WO 2013/033230 and U.S. Pat. No. 8,106,022 B2. In some embodiments, a linker may be selected that is resistant to enzymatic cleavage in vivo. In some embodiments, a linker may be selected that is resistant to hydrolytic cleavage in vivo. In some embodiments, a linker may be selected that will undergo enzymatic cleavage in vivo. In some embodiments, a linker may be selected that will undergo hydrolytic cleavage in vivo.

In certain embodiments, a compound comprising a conjugated modified oligonucleotide described herein has the structure:

$$L\text{-}X_1—N_m—X_2\text{-}MO;$$

wherein each L is a ligand; each N is, independently, a modified or unmodified nucleoside and m is from 1 to 5; $X_1$ and $X_2$ are each, independently, a phosphodiester linkage or a phosphorothioate linkage; and MO is a modified oligonucleotide. In certain embodiments, m is 1. In certain embodiments, m is 2. In certain embodiments, m is 2, 3, 4, or 5. In certain embodiments, m is 3, 4, or 5. In certain embodiments, when m is greater than 1, each modified or unmodified nucleoside of $N_m$ may be connected to adjacent modified or unmodified nucleosides of $N_m$ by a phosphodiester internucleoside linkage or a phosphorothioate internucleoside linkage. In certain embodiments, m is 1 and $X_1$ and $X_2$ are each phosphodiester.

In certain embodiments, a compound comprising a conjugated modified oligonucleotide described herein has Structure A:

$$L_n\text{-linker-}MO;$$

wherein each L is, independently, a ligand and n is from 1 to 10; and MO is a modified oligonucleotide.

In certain embodiments, a compound comprising a conjugated modified oligonucleotide described herein has Structure B:

$$L_n\text{-linker-}X_1—N_m—X_2\text{-}MO;$$

wherein each L is, independently, a ligand and n is from 1 to 10; each N is, independently, a modified or unmodified nucleoside and m is from 1 to 5; $X_1$ and $X_2$ are each, independently, a phosphodiester linkage or a phosphorothioate linkage; and MO is a modified oligonucleotide. In certain embodiments, m is 1. In certain embodiments, m is 2. In certain embodiments, m is 2, 3, 4, or 5. In certain embodiments, m is 3, 4, or 5. In certain embodiments, when m is greater than 1, each modified or unmodified nucleoside of $N_m$ may be connected to adjacent modified or unmodified nucleosides of $N_m$ by a phosphodiester internucleoside linkage or a phosphorothioate internucleoside linkage.

In certain embodiments, a compound comprising a conjugated modified oligonucleotide described herein has Structure C:

$$L_n\text{-linker-}X—N_m—Y\text{-}MO;$$

wherein each L is, independently, a ligand and n is from 1 to 10; each N is, independently, a modified or unmodified nucleoside and m is from 1 to 5; X is a phosphodiester linkage or a phosphorothioate linkage; Y is a phosphodiester linkage; and MO is a modified oligonucleotide. In certain embodiments, m is 1. In certain embodiments, m is 2. In certain embodiments, m is 2, 3, 4, or 5. In certain embodiments, m is 3, 4, or 5. In certain embodiments, when m is greater than 1, each modified or unmodified nucleoside of $N_m$ may be connected to adjacent modified or unmodified nucleosides of $N_m$ by a phosphodiester internucleoside linkage or phosphorothioate internucleoside linkage.

In certain embodiments, a compound comprising a conjugated modified oligonucleotide described herein has Structure D:

$$L_n\text{-linker-}Y—N_m—Y\text{-}MO;$$

wherein each L is, independently, a ligand and n is from 1 to 10; each N is, independently, a modified or unmodified nucleoside and m is from 1 to 5; each Y is a phosphodiester linkage; and MO is a modified oligonucleotide. In certain embodiments, m is 1. In some embodiments, m is 2. In certain embodiments, m is 3, 4, or 5. In certain embodiments, m is 2, 3, 4, or 5. In certain embodiments, when m is greater than 1, each modified or unmodified nucleoside of $N_m$ may be connected to adjacent modified or unmodified nucleosides of $N_m$ by a phosphodiester internucleoside linkage or phosphorothioate internucleoside linkage.

In certain embodiments, when n is greater than 1, the linker comprises a scaffold capable of linking more than one L to the remainder of the compound (i.e., to the modified oligonucleotide (MO), to $X_1$—$N_m$—$X_2$-MO, to X—$N_m$—Y-MO, etc.). In some such embodiments, the $L_n$-linker portion of the compound (such as a compound of Structure A, B, C, or D) comprises Structure E:

$$[L—Q']_n—S—Q''—$$

wherein each L is, independently, a ligand; n is from 1 to 10; S is a scaffold; and Q' and Q" are, independently, linking groups.

In certain embodiments, each Q' and Q" is independently selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl)cyclohexane-1-carboxylate, and 6-aminohexanoic acid.

In certain embodiments, a scaffold links 2, 3, 4, or 5 ligands to a modified oligonucleotide. In certain embodiments, a scaffold links 3 ligands to a modified oligonucleotide.

A nonlimiting exemplary Structure E is Structure E(i):

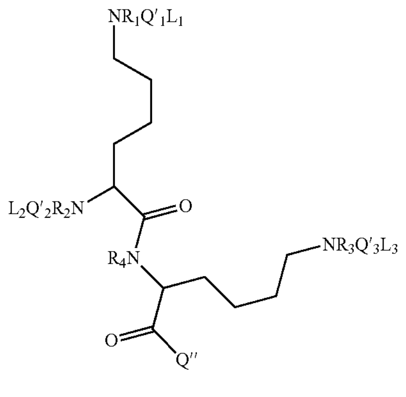

wherein $L_1$, $L_2$, and $L_3$ are each, independently, a ligand; $Q'_1$, $Q'_2$, $Q'_3$, and Q" are each, independently, a linking group; and $R_1$, $R_2$, $R_3$, and $R_4$ are each, independently, selected from H, $C_1$-$C_6$ alkyl, and substituted $C_1$-$C_6$ alkyl.

In some embodiments, $Q'_1$, $Q'_2$, $Q'_3$, and Q" are each, independently, selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl)cyclohexane-1-carboxylate, and 6-aminohexanoic acid. In some embodiments, $R_1$, $R_2$, $R_3$, and $R_4$ are each, independently, selected from H, methyl, ethyl, propyl, isopropyl, and butyl. In some embodiments, $R_1$, $R_2$, $R_3$, and $R_4$ are each selected from H and methyl.

A further nonlimiting exemplary Structure E is Structure E(ii):

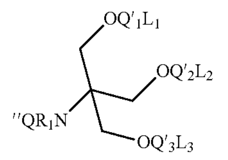

wherein $L_1$, $L_2$, and $L_3$ are each, independently, a ligand; $Q'_1$, $Q'_2$, $Q'_3$, and Q" are each, independently, a linking group; and $R_1$ is selected from H, $C_1$-$C_6$ alkyl, and substituted $C_1$-$C_6$ alkyl.

In some embodiments, $Q'_1$, $Q'_2$, $Q'_3$, and Q" are each, independently, selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl)cyclohexane-1-carboxylate, and 6-aminohexanoic acid. In some embodiments, $R_1$ is selected from H, methyl, ethyl, propyl, isopropyl, and butyl. In some embodiments, $R_1$ is H or methyl.

A further nonlimiting exemplary Structure E is Structure E(iii):

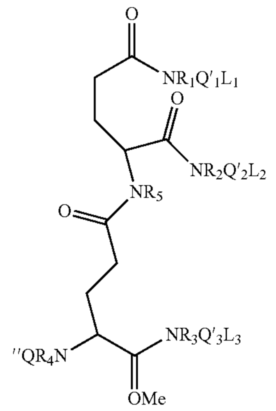

wherein $L_1$, $L_2$, and $L_3$ are each, independently, a ligand; $Q'_1$, $Q'_2$, $Q'_3$, and Q" are each, independently, a linking group; and $R_1$, $R_2$, $R_3$, $R_4$, and $R_5$ are each, independently, selected from H, $C_1$-$C_6$ alkyl, and substituted $C_1$-$C_6$ alkyl.

In some embodiments, $Q'_1$, $Q'_2$, $Q'_3$, and Q" are each, independently, selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl) cyclohexane-1-carboxylate, and 6-aminohexanoic acid. In some embodiments, $R_1$, $R_2$, $R_3$, $R_4$, and $R_5$ are each, independently, selected from H, methyl, ethyl, propyl, isopropyl, and butyl. In some embodiments $R_1$, $R_2$, $R_3$, $R_4$, and $R_5$ are each selected from H and methyl.

A further nonlimiting exemplary Structure E is Structure E(iv):

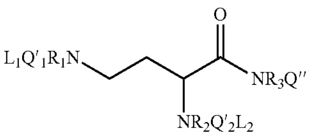

wherein $L_1$ and $L_2$ are each, independently, a ligand; $Q'_1$, $Q'_2$, and Q" are each, independently, a linking group; and $R_1$, $R_2$, and $R_3$ are each, independently, selected from H, $C_1$-$C_6$ alkyl, and substituted $C_1$-$C_6$ alkyl.

In some embodiments, $Q'_1$, $Q'_2$, and Q" are each, independently, selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl)cyclohexane-1-carboxylate, and 6-aminohexanoic acid. In some embodiments, $R_1$, $R_2$, and $R_3$ are each, independently, selected from H, methyl, ethyl, propyl, isopropyl, and butyl. In some embodiments $R_1$, $R_2$, and $R_3$ are each selected from H and methyl.

A further nonlimiting exemplary Structure E is Structure E(v):

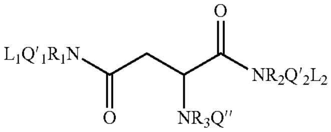

wherein $L_1$ and $L_2$ are each, independently, a ligand; $Q'_1$, $Q'_2$, and Q" are each, independently, a linking group; and $R_1$, $R_2$, and $R_3$ are each, independently, selected from H, $C_1$-$C_6$ alkyl, and substituted $C_1$-$C_6$ alkyl.

A further nonlimiting exemplary Structure E is Structure E(vi):

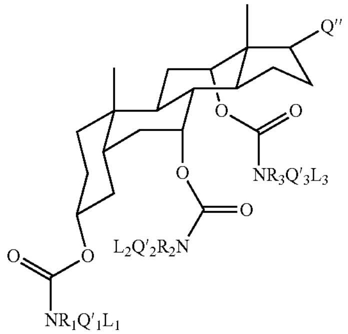

wherein $L_1$, $L_2$, and $L_3$ are each, independently, a ligand; $Q'_1$, $Q'_2$, $Q'_3$, and Q" are each, independently, a linking group; and $R_1$, $R_2$, and $R_3$ are each, independently, selected from H, $C_1$-$C_6$ alkyl, and substituted $C_1$-$C_6$ alkyl.

In some embodiments, $Q'_1$, $Q'_2$, $Q'_3$, and Q" are each, independently, selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl)cyclohexane-1-carboxylate, and 6-aminohexanoic acid. In some embodiments, $R_1$, $R_2$, and $R_3$ are each, independently, selected from H, methyl, ethyl, propyl, isopropyl, and butyl. In some embodiments $R_1$, $R_2$, and $R_3$ are each selected from H and methyl.

A further nonlimiting exemplary Structure E is Structure E(vii):

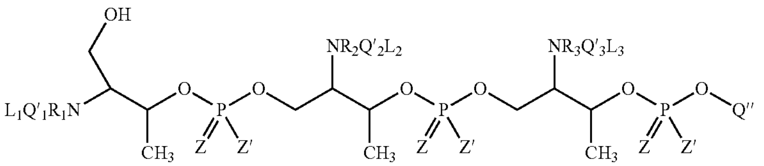

In some embodiments, $Q'_1$, $Q'_2$, and Q" are each, independently, selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl)cyclohexane-1-carboxylate, and 6-aminohexanoic acid. In some embodiments, $R_1$, $R_2$, and $R_3$ are each, independently, selected from H, methyl, ethyl, propyl, isopropyl, and butyl. In some embodiments $R_1$, $R_2$, and $R_3$ are each selected from H and methyl.

wherein $L_1$, $L_2$, and $L_3$ are each, independently, a ligand; $Q'_1$, $Q'_2$, $Q'_3$, and Q" are each, independently, a linking group; $R_1$, $R_2$, and $R_3$ are each, independently, selected from H, $C_1$-$C_6$ alkyl, and substituted $C_1$-$C_6$ alkyl; and Z and Z' are each independently selected from O and S.

In some embodiments, $Q'_1$, $Q'_2$, $Q'_3$, and Q" are each, independently, selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl)cyclohexane-1-carboxylate, and 6-aminohexanoic acid. In some embodiments, $R_1$, $R_2$, and $R_3$ are each, independently, selected from H, methyl, ethyl, propyl, isopropyl, and butyl. In some embodiments $R_1$, $R_2$, and $R_3$ are each selected from H and methyl. In some embodiments, Z or Z' on at least one P atom is S, and the other Z or Z' is O (i.e., a phosphorothioate linkage). In some embodiments, each —OP(Z)(Z')O— is a phosphorothioate linkage. In some embodiments, Z and Z' are both O on at least one P atom (i.e., a phosphodiester linkage). In some embodiments, each —OP(Z)(Z')O— is a phosphodiester linkage.

A further nonlimiting exemplary Structure E is Structure E(viii):

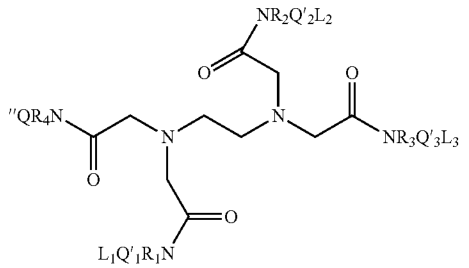

wherein $L_1$, $L_2$, and $L_3$ are each, independently, a ligand; $Q'_1$, $Q'_2$, $Q'_3$, and Q" are each, independently, a linking group; and $R_1$, $R_2$, $R_3$, and $R_4$ are each, independently, selected from H, $C_1$-$C_6$ alkyl, and substituted $C_1$-$C_6$ alkyl.

In some embodiments, $Q'_1$, $Q'_2$, $Q'_3$, and Q" are each, independently, selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl)cyclohexane-1-carboxylate, and 6-aminohexanoic acid. In some embodiments, $R_1$, $R_2$, $R_3$, and $R_4$ are each, independently, selected from H, methyl, ethyl, propyl, isopropyl, and butyl. In some embodiments $R_1$, $R_2$, $R_3$, and $R_4$ are each selected from H and methyl.

Nonlimiting exemplary scaffolds and/or linkers comprising scaffolds, and synthesis thereof, are described, e.g., PCT Publication No. WO 2013/033230, U.S. Pat. No. 8,106,022 B2, U.S. Publication No. 2012/0157509 A1; U.S. Pat. No. 5,994,517; U.S. Pat. No. 7,491,805 B2; U.S. Pat. No. 8,313,772 B2; Manoharan, M., Chapter 16, Antisense Drug Technology, Crooke, S. T., Marcel Dekker, Inc., 2001, 391-469.

In certain embodiments, the $L_n$-linker portion of the compound comprises Structure F:

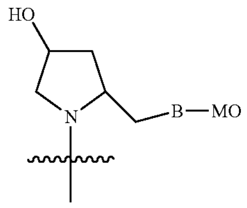

wherein:

B is selected from —O—, —S—, —N($R^N$)—, —Z—P(Z')(Z")O—, —Z—P(Z')(Z")O—$N_m$—X—, and —Z—P(Z')(Z")O—$N_m$—Y—;

MO is a modified oligonucleotide;

$R^N$ is selected from H, methyl, ethyl, propyl, isopropyl, butyl, and benzyl;

Z, Z', and Z" are each independently selected from O and S;

each N is, independently, a modified or unmodified nucleoside;

m is from 1 to 5;

X is selected from a phosphodiester linkage and a phosphorothioate linkage;

Y is a phosphodiester linkage; and the wavy line indicates the connection to the rest of the linker and ligand(s).

In certain embodiments, the wavy line indicates a connection to Structure E, above.

In certain embodiments, n is from 1 to 5, 1 to 4, 1 to 3, or 1 to 2. In certain embodiments, n is 1. In certain embodiments, n is 2. In certain embodiments, n is 3. In certain embodiments, n is 4. In certain embodiments, n is 5.

In certain embodiments, the $L_n$-linker portion of the compound comprises Structure G:

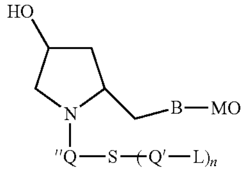

wherein:

B is selected from —O—, —S—, —N($R^N$)—, —Z—P(Z')(Z")O—, —Z—P(Z')(Z")O—$N_m$—X—, and —Z—P(Z')(Z")O—$N_m$—Y—;

MO is a modified oligonucleotide;

$R^N$ is selected from H, methyl, ethyl, propyl, isopropyl, butyl, and benzyl;

Z, Z', and Z" are each independently selected from O and S;

each N is, independently, a modified or unmodified nucleoside;

m is from 1 to 5;

X is selected from a phosphodiester linkage and a phosphorothioate linkage;

Y is a phosphodiester linkage;

each L is, independently, a ligand; n is from 1 to 10; S is a scaffold; and Q' and Q" are, independently, linking groups.

In certain embodiments, each Q' and Q" are independently selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl)cyclohexane-1-carboxylate, and 6-aminohexanoic acid.

A nonlimiting exemplary $L_n$-linker portion (e.g., of Structure F or G) of a compound is shown in Structure H below:

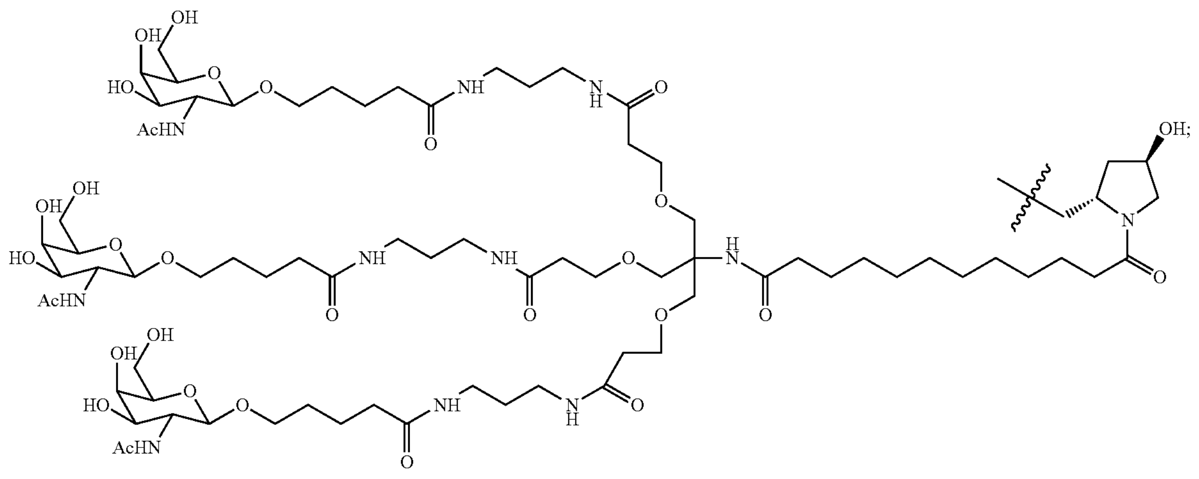 [SMILES: *C[C@@H]1C[C@@H](O)CN1C(=O)CCCCCCCCCCC(=O)NC(COCCC(=O)NCCCNC(=O)CCCCOC1OC(CO)C(O)C(O)C1NC(C)=O)(COCCC(=O)NCCCNC(=O)CCCCOC1OC(CO)C(O)C(O)C1NC(C)=O)COCCC(=O)NCCCNC(=O)CCCCOC1OC(CO)C(O)C(O)C1NC(C)=O]

wherein the wavy line indicates attachment to the modified oligonucleotide (MO), to $X_1$, e.g. in Structure B, or to X or Y, e.g., in Structure C, or D.

In certain embodiments, each ligand is a carbohydrate. A compound comprising a carbohydrate-conjugated modified oligonucleotide, when recognized by a cell surface lectin, is transported across the cell membrane into the cell. In certain embodiments, a cell surface lectin is a C-type lectin. In certain embodiments, the C-type lectin is present on a Kuppfer cell. In certain embodiments, a C-type lectin is present on a macrophage. In certain embodiments, a C-type lectin is present on an endothelial cell. In certain embodiments, a C-type lectin is present on a monocyte. In certain embodiments, a C-type lectin is present on a leukocyte. In certain embodiments, a C-type lectin is present on a dendritic cell. In certain embodiments, a C-type lectin is present on a B cell. A conjugate may facilitate uptake of an anti-miR-122 compound into any cell type that expresses a C-type lectin.

In certain embodiments, a C-type lectin is the asialoglycoprotein receptor (ASGPR). In certain embodiments, a conjugate comprises one or more ligands having affinity for the ASGPR, including but not limited to galactose or a galactose derivative. In certain embodiments, a ligand having affinity for the ASGPR is N-acetylgalactosamine, galactose, galactosamine, N-formylgalactosamine, N-propionyl-galactosamine, N-n-butanoylgalactosamine, or N-iso-butanoyl-galactosamine. Such conjugates facilitate the uptake of compounds into cells that express the ASGPR, for example, hepatocytes and dendritic cells.

In certain embodiments, a ligand is a carbohydrate selected from mannose, glucose, galactose, ribose, arabinose, fructose, fucose, xylose, D-mannose, L-mannose, D-galactose, L-galactose, D-glucose, L-glucose, D-ribose, L-ribose, D-arabinose, L-arabinose, D-fructose, L-fructose, D-fucose, L-fucose, D-xylose, L-xylose, alpha-D-mannofuranose, beta-D-mannofuranose, alpha-D-mannopyranose, beta-D-mannopyranose, alpha-D-glucofuranose, Beta-D-glucofuranose, alpha-D-glucopyranose, beta-D-glucopyranose, alpha-D-galactofuranose, beta-D-galactofuranose, alpha-D-galactopyranose, beta-D-galactopyranose, alpha-D-ribofuranose, beta-D-ribofuranose, alpha-D-ribopyranose, beta-D-ribopyranose, alpha-D-fructofuranose, alpha-D-fructopyranose, glucosamine, galactosamine, sialic acid, and N-acetylgalactosamine.

In certain embodiments, a ligand is selected from N-acetyl-galactosamine, galactose, galactosamine, N-formylgalactosamine, N-propionyl-galactosamine, N-n-butanoylgalactosamine, and N-iso-butanoyl-galactosamine In certain embodiments, a ligand is N-acetylgalactosamine.

In certain embodiments, a compound comprises the structure:

(I)

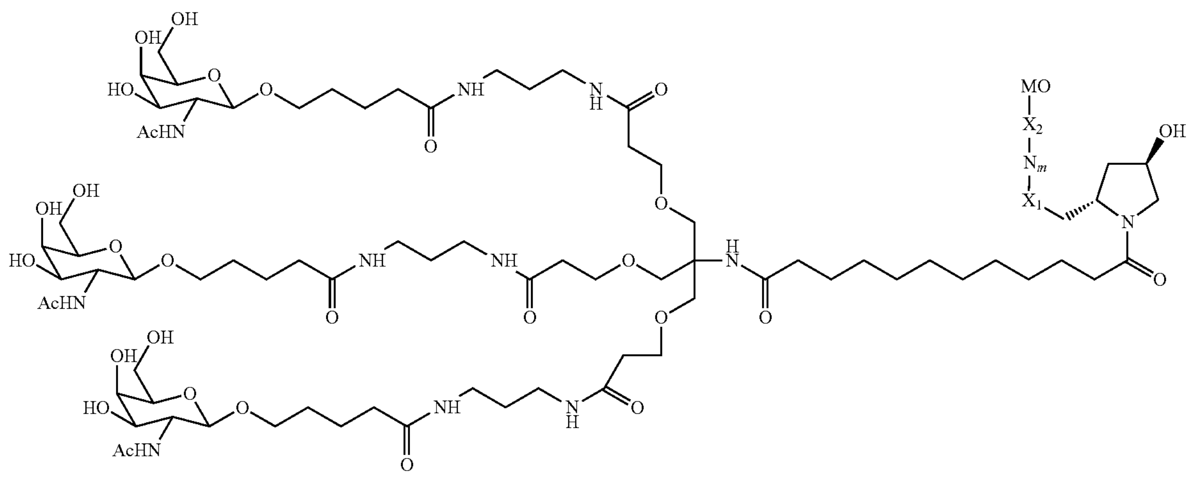

wherein each N is, independently, a modified or unmodified nucleoside and m is from 1 to 5; $X_1$ and $X_2$ are each, independently, a phosphodiester linkage or a phosphorothioate linkage; and MO is a modified oligonucleotide. In certain embodiments, m is 1. In certain embodiments, m is 2. In certain embodiments, m is 3, 4, or 5. In certain embodiments, m is 2, 3, 4, or 5. In certain embodiments, when m is greater than 1, each modified or unmodified nucleoside of $N_m$ may be connected to adjacent modified or unmodified nucleosides of $N_m$ by a phosphodiester internucleoside linkage or phosphorothioate internucleoside linkage.

In certain embodiments, a compound comprises the structure:

(II)

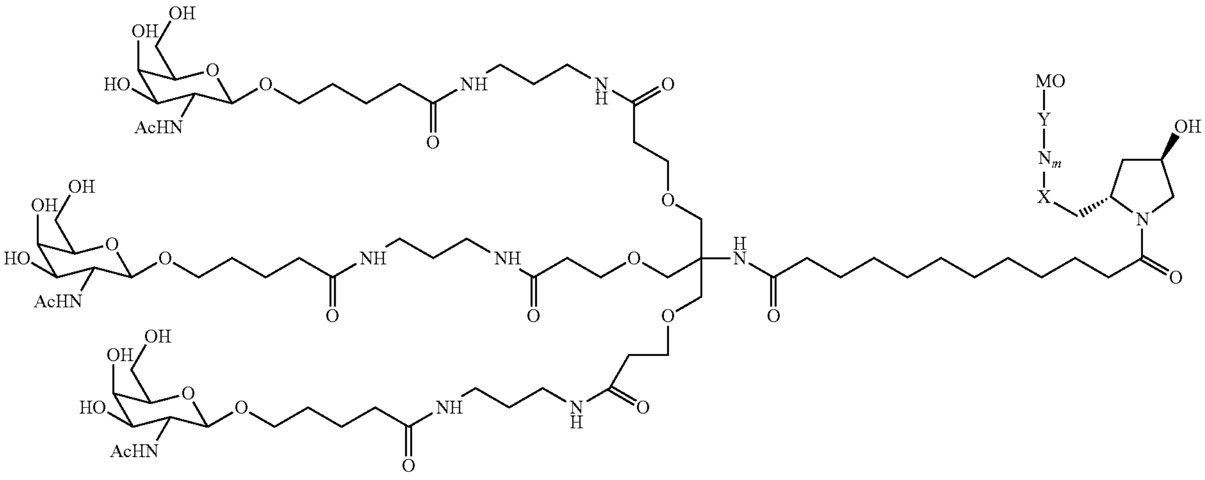

wherein X is a phosphodiester linkage or a phosphorothioate linkage; each N is, independently, a modified or unmodified nucleoside and m is from 1 to 5; Y is a phosphodiester linkage; and MO is a modified oligonucleotide. In certain embodiments, m is 1. In certain embodiments, m is 2. In certain embodiments, m is 2, 3, 4, or 5. In certain embodiments, m is 3, 4, or 5. In certain embodiments, when m is greater than 1, each modified or unmodified nucleoside of $N_m$ may be connected to adjacent modified or unmodified nucleosides of $N_m$ by a phosphodiester internucleoside linkage or phosphorothioate internucleoside linkage.

In certain embodiments, a compound comprises a modified nucleotide and a conjugate moiety, wherein the modified oligonucleotide has the structure $C_LCA_LTTG_LT_LCAC_LA$-$C_LTC_LC_L$ (SEQ ID NO: 7), wherein the subscript "L" indicates an LNA and nucleosides not followed by a subscript are β-D-deoxyribonucleosides, and each internucleoside linkage is a phosphorothioate internucleoside linkage, and wherein the conjugate moiety is linked to the 3' terminus of the modified oligonucleotide and has the structure:

(I)

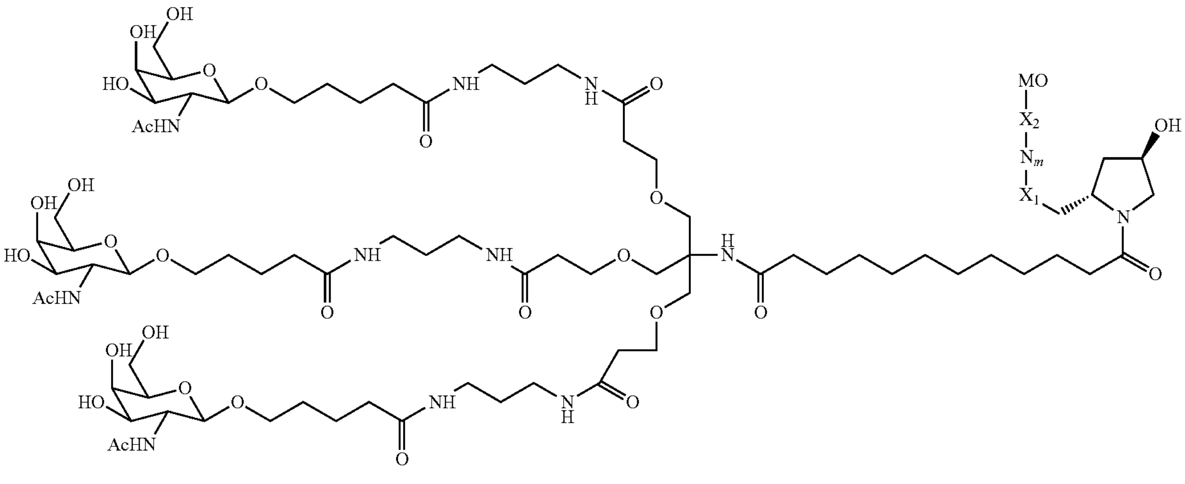

wherein each N is, independently, a modified or unmodified nucleoside and m is from 1 to 5; $X_1$ and $X_2$ are each, independently, a phosphodiester linkage or a phosphorothioate linkage; and MO is a modified oligonucleotide. In some embodiments, all of the $C_L$ nucleosides are $^{Me}C_L$ nucleosides, wherein the superscript "Me" indicates 5-methylcytosine.

In some embodiments, a compound has the structure:

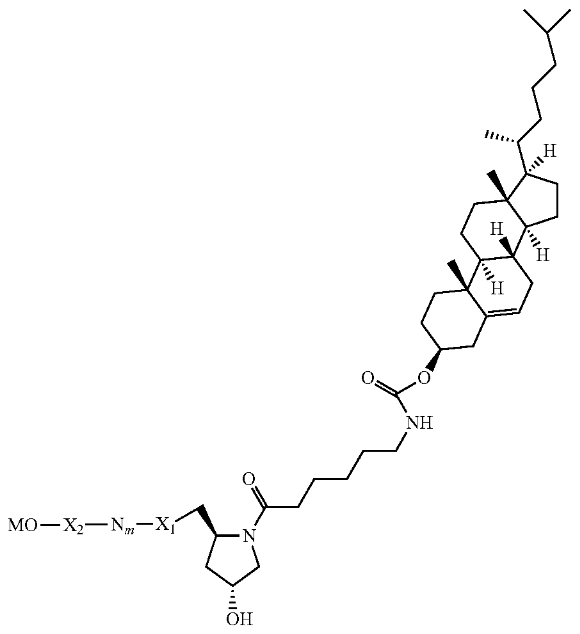

wherein each N is, independently, a modified or unmodified nucleoside and m is from 1 to 5; $X_1$ and $X_2$ are each, independently, a phosphodiester linkage or a phosphorothioate linkage; and MO is a modified oligonucleotide.

In certain embodiments, at least one of $X_1$ and $X_2$ is a phosphodiester linkage. In certain embodiments, each of $X_1$ and $X_2$ is a phosphodiester linkage.

In certain embodiments, m is 1. In certain embodiments, m is 2. In certain embodiments, m is 3, 4, or 5. In certain embodiments, m is 2, 3, 4, or 5. In certain embodiments, when m is greater than 1, each modified or unmodified nucleoside of $N_m$ may be connected to adjacent modified or unmodified nucleosides of $N_m$ by a phosphodiester internucleoside linkage or a phosphorothioate internucleoside linkage.

In any of the embodiments described herein, $N_m$ may be $N'_pN''$, where each N' is, independently, a modified or unmodified nucleoside and p is from 0 to 4; and N" is a nucleoside comprising an unmodified sugar moiety.

In certain embodiments, p is 0. In certain embodiments, p is 1, 2, 3, or 4. In certain embodiments, when p is 1, 2, 3, or 4, each N' comprises an unmodified sugar moiety.

In certain embodiments, an unmodified sugar moiety is a β-D-ribose or a β-D-deoxyribose.

In certain embodiments, where p is 1, 2, 3, or 4, N' comprises a purine nucleobase. In certain embodiments, N" comprises a purine nucleobase. In certain embodiments, a purine nucleobase is selected from adenine, guanine, hypoxanthine, xanthine, and 7-methylguanine. In certain embodiments, N' is a β-D-deoxyriboadenosine or a β-D-deoxyriboguanosine. In certain embodiments, N" is a β-D-deoxyriboadenosine or a β-D-deoxyriboguanosine.

In certain embodiments, p is 1, N' and N" are each a β-D-deoxyriboadenosine, and N' and N" are linked by a phosphodiester internucleoside linkage. In certain embodiments, p is 1, N' and N" are each a β-D-deoxyriboadenosine, and N' and N" are linked by a phosphodiester internucleoside linkage. In certain embodiments, p is 1, N' and N" are each a β-D-deoxyriboadenosine, and N' and N" are linked by a phosphorothioate internucleoside linkage.

In certain embodiments, where p is 1, 2, 3, or 4, N' comprises a pyrimidine nucleobase. In certain embodiments, N" comprises a pyrimidine nucleobase. In certain embodiments, a pyrimidine nucleobase is selected from cytosine, 5-methylcytosine, thymine, uracil, and 5,6-dihydrouracil.

In certain embodiments, the sugar moiety of each N is independently selected from a β-D-ribose, a β-D-deoxyribose, a 2'-O-methoxy sugar, a 2'-O-methyl sugar, a 2'-fluoro sugar, and a bicyclic sugar moiety. In certain embodiments, each bicyclic sugar moiety is independently selected from a cEt sugar moiety, an LNA sugar moiety, and an ENA sugar moiety. In certain embodiments, the cEt sugar moiety is an S-cEt sugar moiety. In certain embodiments, the cEt sugar moiety is an R-cEt sugar moiety.

In certain embodiments, a compound comprises the structure:

(II)

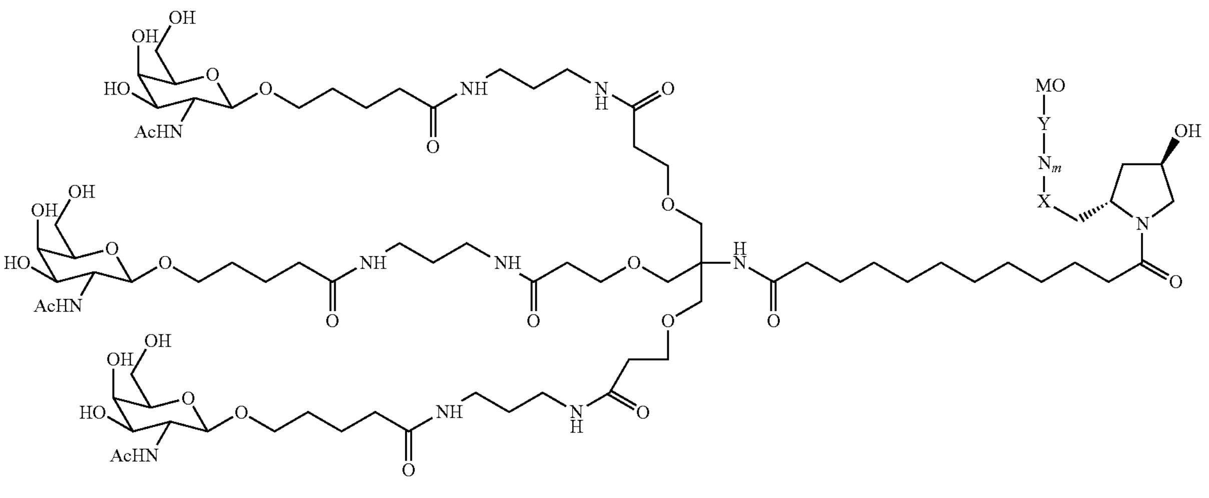

wherein X is a phosphodiester linkage; m is 1; N is a β-D-deoxyriboadenosine; Y is a phosphodiester linkage; and MO is a modified oligonucleotide.

In certain embodiments, a compound comprises the structure:

(II)

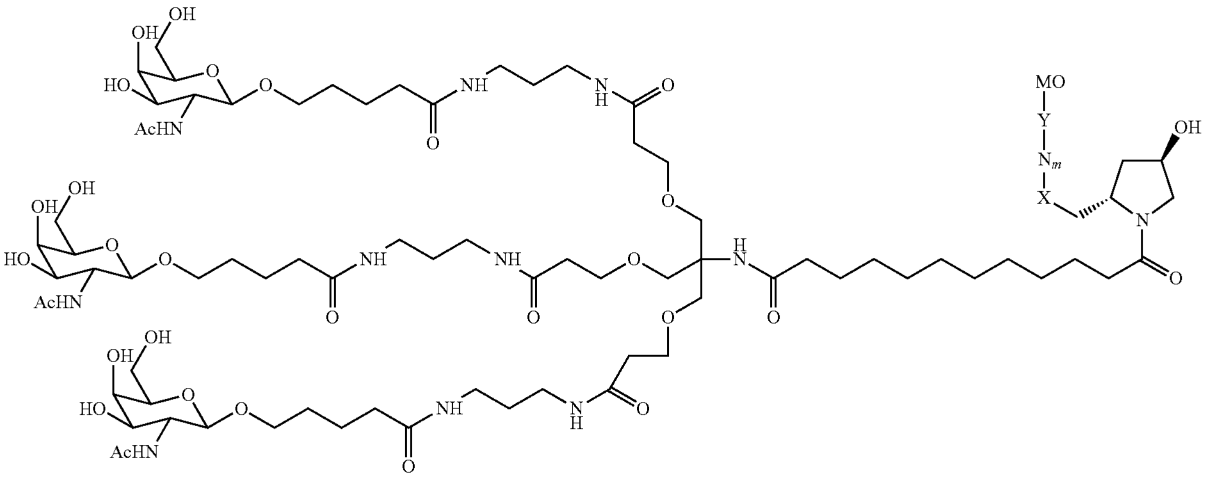

wherein X is a phosphodiester linkage; m is 2; each N is a β-D-deoxyriboadenosine; the nucleosides of N are linked by a phosphodiester internucleoside linkage; Y is a phosphodiester linkage; and MO is a modified oligonucleotide.

In certain embodiments, a compound comprises a modified nucleotide and a conjugate moiety, wherein the modified oligonucleotide has the structure $A_E{}^{Me}C_EA_E{}^{Me}C_E{}^{Me}C_EA_ET_ETGU_SC_SAC_SAC_STC_SC_S$ (SEQ ID NO: 4), where nucleosides not followed by a subscript are β-D-deoxyribonucleosides; nucleosides followed by a subscript "E" are 2'-MOE nucleosides; nucleosides followed by a subscript "S" are S-cEt nucleosides; and each internucleoside linkage is a phosphorothioate internucleoside linkage; and wherein the conjugate moiety is linked to the 3' terminus of the modified oligonucleotide and has the structure:

wherein X is a phosphodiester linkage; m is 1; N is a β-D-deoxyriboadenosine; Y is a phosphodiester linkage; and MO is the modified oligonucleotide.

In certain embodiments, a compound comprises a modified nucleotide and a conjugate moiety, wherein the modified oligonucleotide has the structure $C_LCA_LTTG_LT_LCAC_LA$-$C_LTC_LC_L$ (SEQ ID NO: 7), wherein the subscript "L" indicates an LNA and nucleosides not followed by a subscript are β-D-deoxyribonucleosides, and each internucleoside linkage is a phosphorothioate internucleoside linkage, and wherein the conjugate moiety is linked to the 3' terminus of the modified oligonucleotide and has the structure:

(II)

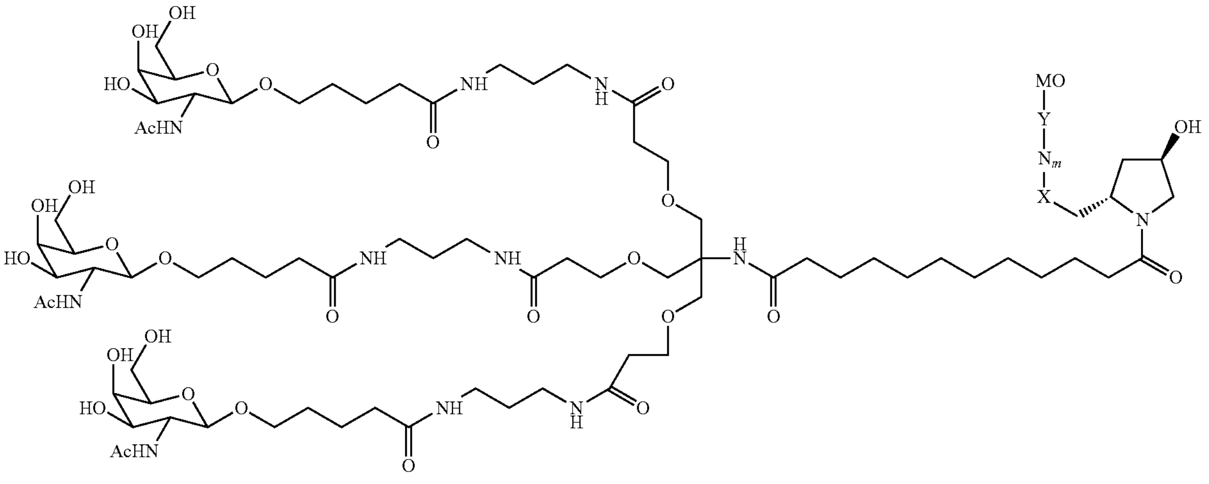

(II)

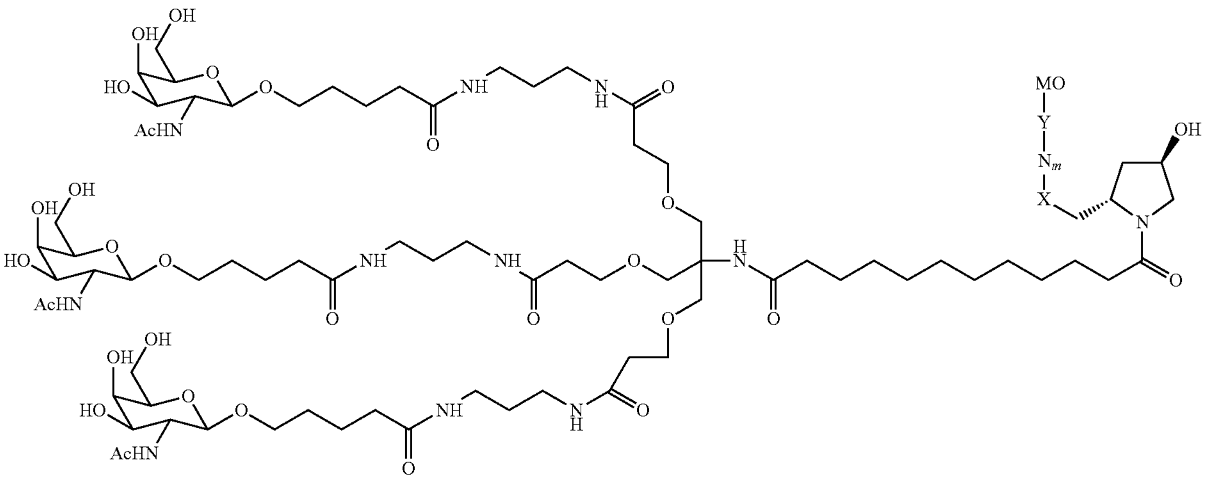

wherein X is a phosphodiester linkage; m is 1; N is a β-D-deoxyriboadenosine; Y is a phosphodiester linkage; and MO is the modified oligonucleotide. In some embodiments, all of the $C_L$ nucleosides are $^{Me}C_L$ nucleosides, wherein the superscript "Me" indicates 5-methylcytosine.

In certain embodiments, a modified oligonucleotide has a nucleobase sequence and modifications as shown in Table 2. Nucleosides and nucleobases are indicated as follows: the superscript "Me" indicates 5-methylcytosine; nucleosides not followed by a subscript are β-D-deoxyribonucleosides; nucleosides followed by a subscript "E" are 2'-MOE nucleosides; nucleosides followed by a subscript "S" are S-cEt nucleosides; and each internucleoside linkage is a phosphorothioate internucleoside linkage.

TABLE 2

Conjugated modified oligonucleotides

Figure 3A:
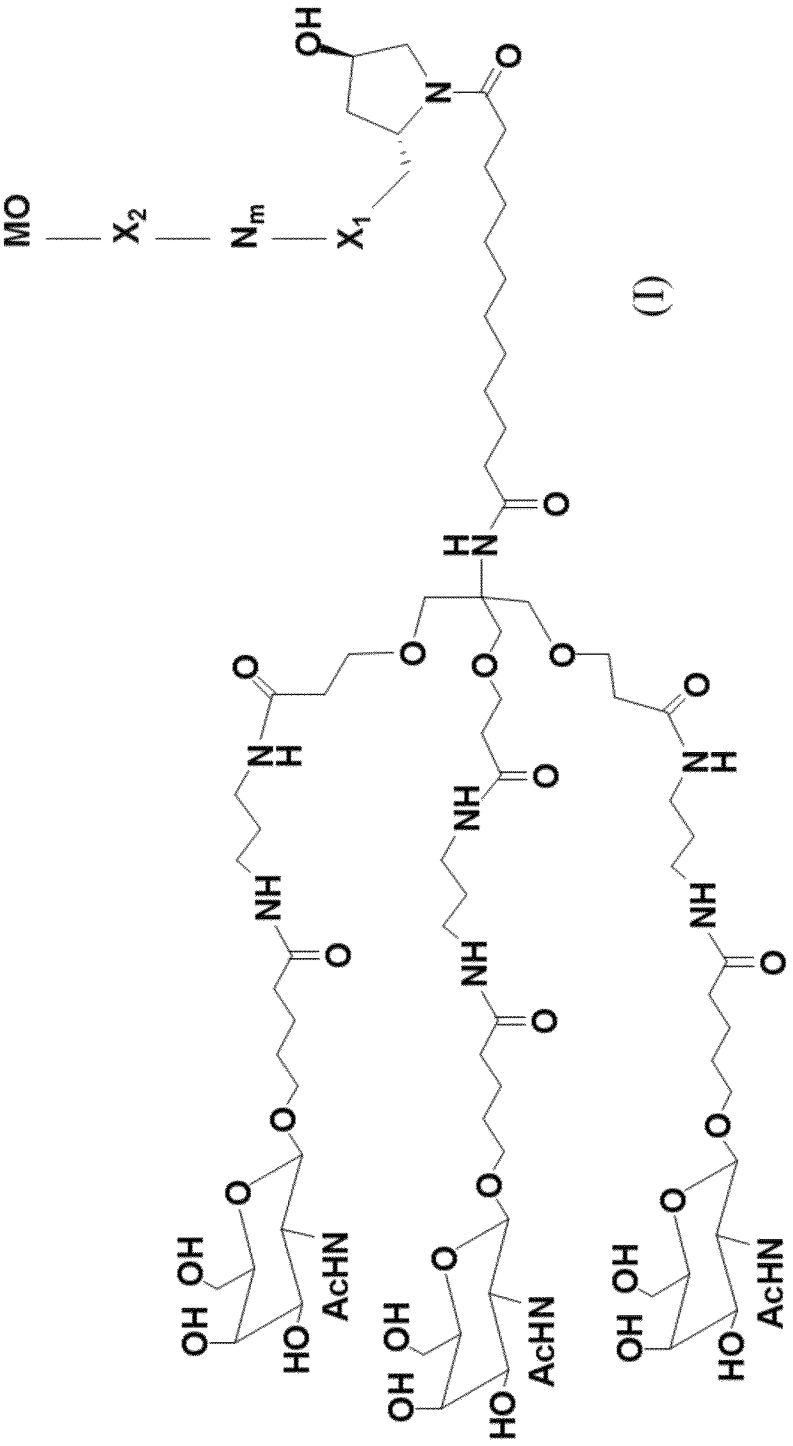
FIGS. 3A, 3B, and 3C. Conjugated modified oligonucleotide structures.
Figure 3B:
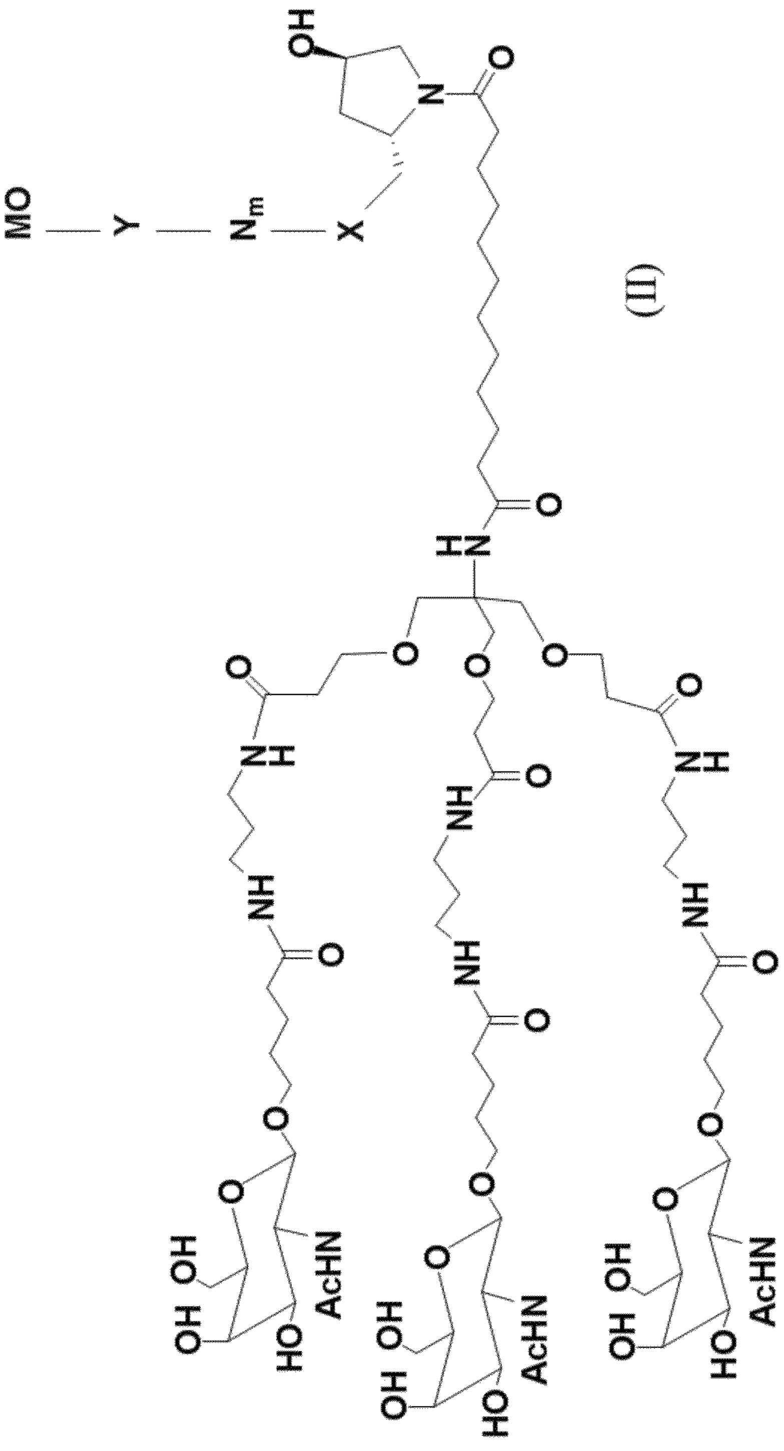
Figure 3C:
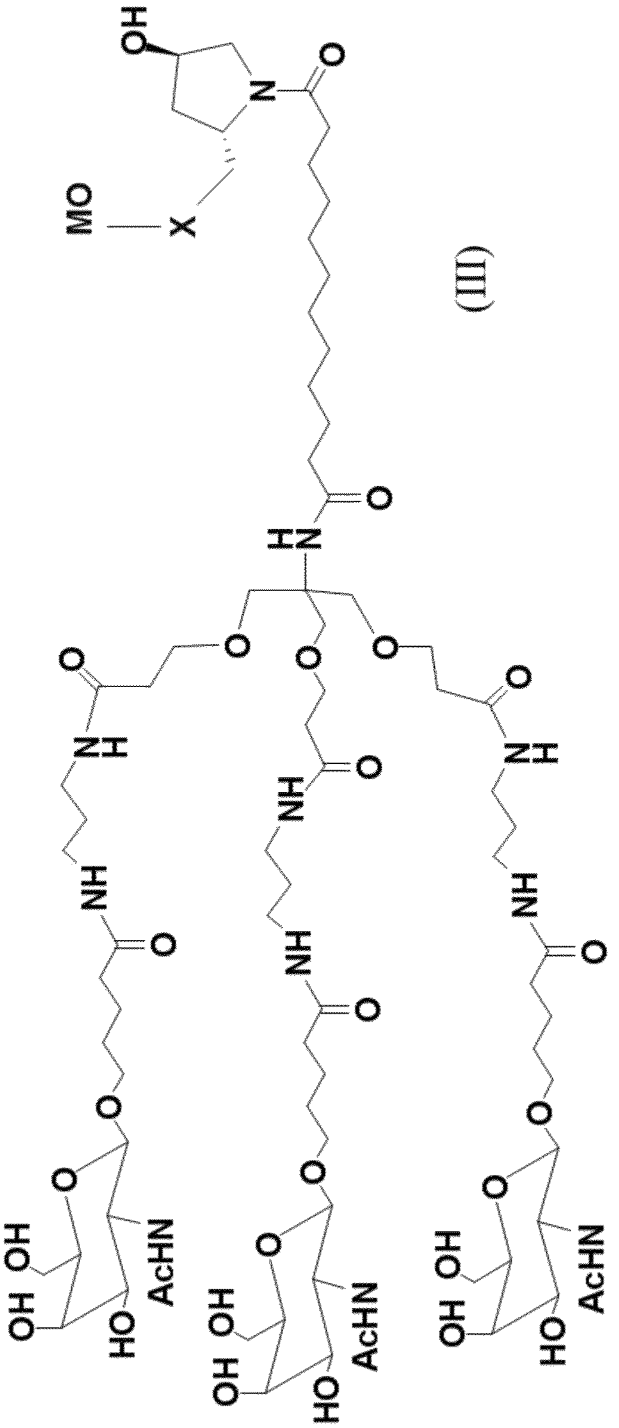

| Cmpd # | Sequence (5' to 3') and Modifications | Linkage to GalNAc structure | SEQ ID NO |
|---|---|---|---|
| 38368 | $A_E$ $^{Me}C_E$ $A_E$ $^{Me}C_E$ $^{Me}C_E$ $A_E$ $T_E$ T G $U_S$ $C_S$ A $C_S$ A $C_S$ T $C_S$ $C_S$ | Structure III of Figure 3C, where X is a phosphodiester linkage and MO is compound 38649 | 4 |
| 38371 | $A_E$ $^{Me}C_E$ $A_E$ $^{Me}C_E$ $^{Me}C_E$ $A_E$ $T_E$ T G $U_S$ $C_S$ A $C_S$ A $C_S$ T $C_S$ $C_S$ | Structure III of Figure 3C, where X is a phosphorothioate linkage and MO is compound 38649 | 4 |
| 38458 | $A_E$ $^{Me}C_E$ $A_E$ $^{Me}C_E$ $^{Me}C_E$ $A_E$ $T_E$ T G $U_S$ $C_S$ A $C_S$ A $C_S$ T $C_S$ $C_S$ | Structure I of Figure 3C, where $X_2$ is a phophorothioate linkage, m is 1, $N_m$ is a β-D-deoxynucleoside (dA), $X_1$ is a phosphorothioate linkage, and MO is compound 38649 | 4 |
| 38459 | $A_E$ $^{Me}C_E$ $A_E$ $^{Me}C_E$ $^{Me}C_E$ $A_E$ $T_E$ T G $U_S$ $C_S$ A $C_S$ A $C_S$ T $C_S$ $C_S$ | Structure I of Figure 3C, where $X_2$ is a phophodiester linkage, m is 1, $N_m$ is a β-D-deoxynucleoside (dA), $X_1$ is a phosphorothioate linkage, and MO is compound 38649 | 4 |
| 38597 | $A_E$ $^{Me}C_E$ $A_E$ $^{Me}C_E$ $^{Me}C_E$ $A_E$ $T_E$ T G $U_S$ $C_S$ A $C_S$ A $C_S$ T $C_S$ $C_S$ | Structure I of Figure 3C, where $X_2$ is a phophorothioate linkage, m is 1, $N_m$ is a 2'-O-methoxyethyl nucleoside, $X_1$ is a phosphorothioate linkage, and MO is compound 38649 | 4 |
| 38598 | $A_E$ $^{Me}C_E$ $A_E$ $^{Me}C_E$ $^{Me}C_E$ $A_E$ $T_E$ T G $U_S$ $C_S$ A $C_S$ A $C_S$ T $C_S$ $C_S$ | Structure I of Figure 3C, where $X_2$ is a phophorothioate linkage, m is 1, $N_m$ is a $X_1$ is a phosphorothioate linkage, and MO is compound 38649 | 4 |

In certain embodiments, a compound provided herein comprises a modified nucleotide and a conjugate moiety, wherein the modified oligonucleotide has the structure $C_SA_SC_SA_S C_SU_SC_SC_S$ (SEQ ID NO: 9), wherein the subscript "S" indicates an S-cEt and nucleosides not followed by a subscript are β-D-deoxyribonucleosides, and each internucleoside linkage is a phosphorothioate internucleoside linkage, and wherein the conjugate moiety is linked to the 3' terminus of the modified oligonucleotide and has the structure:

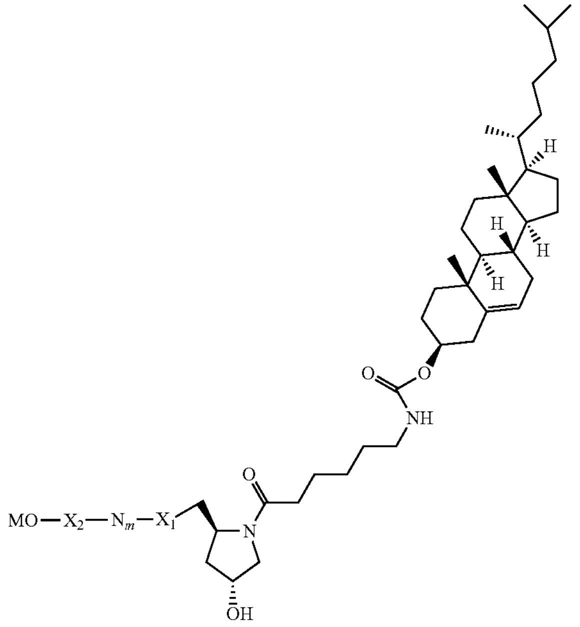

wherein $X_1$ and $X_2$ are phosphodiester linkages; m is 1; N is a β-D-deoxyriboadenosine; and MO is the modified oligonucleotide.

Additional moieties for conjugation to a modified oligonucleotide include phenazine, phenanthridine, anthraquinone, acridine, fluoresceins, rhodamines, coumarins, and dyes. In certain embodiments, a conjugate group is attached directly to a modified oligonucleotide.

Certain Metabolic Products

Upon exposure to exonucleases and/or endonucleases in vitro or in vivo, compounds may undergo cleavage at various positions throughout the compound. The products of such cleavage may retain some degree of the activity of the parent compound, and as such are considered active metabolites. As such, a metabolic product of a compound may be used in the methods described herein. In certain embodiments, a modified oligonucleotide (unconjugated or conjugated) undergoes cleavage at the 5' end and/or the 3' end, resulting in a metabolic product that has 1, 2, or 3 fewer nucleotides at the 5' end and/or the 3' end, relative to the parent modified oligonucleotide. In certain embodiments, a modified oligonucleotide undergoes cleavage at the 5' end, releasing the 5'-terminal nucleotide and resulting in a metabolic product that has 1 less nucleotide at the 5' end, relative to the parent modified oligonucleotide. In certain embodiments, a modified oligonucleotide undergoes cleavage at the 5' end, releasing two 5'-terminal nucleosides and resulting in a metabolic product that has two fewer nucleotides at the 5' end, relative to the parent modified oligonucleotide. In certain embodiments, a modified oligonucleotide undergoes cleavage at the 3' end, releasing the 3'-terminal nucleotide and resulting in a metabolic product that has one less nucleotide at the 3' end, relative to the parent modified oligonucleotide. In certain embodiments, a modified oligonucleotide undergoes cleavage at the 3' end, releasing two 3'-terminal nucleosides and resulting in a metabolic product that has two fewer nucleotides at the 3' end, relative to the parent modified oligonucleotide.

Compounds comprising modified oligonucleotide linked to a conjugate moiety may also undergo cleavage at a site within the linker between the modified oligonucleotide and the ligand. In certain embodiments, cleavage yields the parent modified oligonucleotide comprising a portion of the conjugate moiety. In certain embodiments, cleavage yields the parent modified oligonucleotide comprising one or more subunits of the linker between the modified oligonucleotide and the ligand. For example, where a compound has the structure $L_n$-linker-$N_m$—P-MO, in some embodiments, cleavage yields the parent modified oligonucleotide comprising one or more nucleotides of $N_m$. In some embodiments, cleavage of a conjugated modified oligonucleotide yields the parent modified oligonucleotide. In some such embodiments, for example, where a compound has the structure $L_n$-linker-$N_m$—P-MO, in some embodiments, cleavage yields the parent modified oligonucleotide without any of the nucleotides of $N_m$.

Certain Nucleobase Sequences

Nucleobase sequences of mature miR-122 and its corresponding stem-loop sequence are found in miRBase, an online searchable database of microRNA sequences and annotation, found at microrna.sanger.ac.uk. Entries in the miRBase Sequence database represent a predicted hairpin portion of a microRNA transcript (the stem-loop), with information on the location and sequence of the mature microRNA sequence. The microRNA stem-loop sequences in the database are not strictly precursor microRNAs (pre-microRNAs), and may in some instances include the pre-microRNA and some flanking sequence from the presumed primary transcript. The microRNA nucleobase sequences described herein encompass any version of the microRNA, including the sequences described in Release 15.0 of the miRBase sequence database and sequences described in any earlier Release of the miRBase sequence database. A sequence database release may result in the re-naming of certain microRNAs. The present invention encompasses modified oligonucleotides that are complementary to any nucleobase sequence version of the microRNAs described herein.

In certain embodiments, each nucleobase of a modified oligonucleotide targeted to miR-122 is capable of undergoing base-pairing with a nucleobase at a corresponding position in the nucleobase sequence of miR-122, or a precursor thereof. In certain embodiments the nucleobase sequence of a modified oligonucleotide may have one or more mismatched basepairs with respect to its target microRNA or precursor sequence, and remains capable of hybridizing to its target sequence.

In certain embodiments, a modified oligonucleotide has a nucleobase sequence that is complementary to the nucleobase sequence of miR-122 precursor, such as miR-122 stem-loop sequence. As miR-122 is contained within a miR-122 precursor sequence, a modified oligonucleotide having a nucleobase sequence complementary to miR-122 is also complementary to a region of a miR-122 precursor.

In certain embodiments, a modified oligonucleotide has a nucleobase sequence that is complementary to nucleobases 1 to 16, 1 to 17, 1 to 18, 1 to 19, 1 to 20, 1 to 21, or 1 to 22 of SEQ ID NO: 1.

In certain embodiments, a modified oligonucleotide has a nucleobase sequence that is complementary to nucleobases 2 to 16, 2 to 17, 2 to 18, 2 to 19, 2 to 20, 2 to 21, or 2 to 22 of SEQ ID NO: 1.

In certain embodiments, a modified oligonucleotide has a nucleobase sequence that is complementary to nucleobases 3 to 17, 3 to 18, 3 to 19, 3 to 20, 3 to 21, or 3 to 22 of SEQ ID NO: 1.

In certain embodiments, the number of linked nucleosides of a modified oligonucleotide is less than the length of the miR-122, or a precursor thereof. In certain such embodiments, the oligonucleotide has a nucleobase sequence that is complementary to a region of miR-122, or a precursor thereof. A modified oligonucleotide having a number of linked nucleosides that is less than the length of miR-122, wherein each nucleobase of a modified oligonucleotide is complementary to each nucleobase at a corresponding position in a miR-122 nucleobase sequence, is considered to be a modified oligonucleotide having a nucleobase sequence that is fully complementary to miR-122. For example, a modified oligonucleotide consisting of 19 linked nucleosides, where the nucleobases of nucleosides 1 through 19 are each complementary to a corresponding position of miR-122, where the miR-122 is 22 nucleobases in length, is fully complementary to 19 contiguous nucleobases of miR-122. Such a modified oligonucleotide has a nucleobase sequence that is 100% complementary to the nucleobase sequence of miR-122.

In certain embodiments, the number of linked nucleosides of a modified oligonucleotide is one less than the length of the miR-122. In certain embodiments, a modified oligonucleotide has one less nucleoside at the 5' terminus. In certain embodiments, a modified oligonucleotide has one less nucleoside at the 3' terminus. In certain embodiments, a modified oligonucleotide has two fewer nucleosides at the 5' terminus. In certain embodiments, a modified oligonucleotide has two fewer nucleosides at the 3' terminus In certain embodiments, 15 contiguous nucleobases of a modified oligonucleotide are each complementary to 15 contiguous nucleobases of miR-122. In certain embodiments, 16 contiguous nucleobases of a modified oligonucleotide are each complementary to 16 contiguous nucleobases of miR-122. In certain embodiments, 17 contiguous nucleobases of a modified oligonucleotide are each complementary to 17 contiguous nucleobases of miR-122. In certain embodiments, 18 contiguous nucleobases of a modified oligonucleotide are each complementary to 18 contiguous nucleobases of miR-122. In certain embodiments, 19 contiguous nucleobases of a modified oligonucleotide are each complementary to 19 contiguous nucleobases of miR-122. In certain embodiments, 20 contiguous nucleobases of a modified oligonucleotide are each complementary to 20 contiguous nucleobases of miR-122. In certain embodiments, 21 contiguous nucleobases of a modified oligonucleotide are each complementary to 21 contiguous nucleobases of miR-122. In certain embodiments, 22 contiguous nucleobases of a modified oligonucleotide are each complementary to 22 contiguous nucleobases of miR-122.

In certain embodiments, a modified oligonucleotide comprises a nucleobase sequence that is complementary to a seed sequence, i.e. a modified oligonucleotide comprises a seed-match sequence. In certain embodiments, a seed sequence is a hexamer seed sequence. In certain such embodiments, a seed sequence is nucleobases 1-6 of miR-122. In certain such embodiments, a seed sequence is nucleobases 2-7 of miR-122. In certain such embodiments, a seed sequence is nucleobases 3-8 of miR-122. In certain embodiments, a seed sequence is a heptamer seed sequence. In certain such embodiments, a heptamer seed sequence is nucleobases 1-7 of miR-122. In certain such embodiments, a heptamer seed sequence is nucleobases 2-8 of miR-122. In certain embodiments, the seed sequence is an octamer seed sequence. In certain such embodiments, an octamer seed sequence is nucleobases 1-8 of miR-122. In certain embodiments, an octamer seed sequence is nucleobases 2-9 of miR-122.

In certain embodiments, the number of linked nucleosides of a modified oligonucleotide is greater than the length the miR-122 sequence. In certain such embodiments, the nucleobase of an additional nucleoside is complementary to a nucleobase of miR-122 stem-loop sequence. In certain embodiments, the number of linked nucleosides of a modified oligonucleotide is one greater than the length of miR-122. In certain such embodiments, the additional nucleoside is at the 5' terminus of a modified oligonucleotide. In certain such embodiments, the additional nucleoside is at the 3' terminus of a modified oligonucleotide. In certain embodiments, the number of linked nucleosides of a modified oligonucleotide is two greater than the length of miR-122. In certain such embodiments, the two additional nucleosides are at the 5' terminus of a modified oligonucleotide. In certain such embodiments, the two additional nucleosides are at the 3' terminus of a modified oligonucleotide. In certain such embodiments, one additional nucleoside is located at the 5' terminus and one additional nucleoside is located at the 3' terminus of a modified oligonucleotide. In certain embodiments, a region of the oligonucleotide may be fully complementary to the nucleobase sequence of miR-122, but the entire modified oligonucleotide is not fully complementary to miR-122. For example, a modified oligonucleotide consisting of 23 linked nucleosides, where the nucleobases of nucleosides 1 through 22 are each complementary to a corresponding position of miR-122 that is 22 nucleobases in length, has a 22 nucleoside portion that is fully complementary to the nucleobase sequence of miR-122.

In certain embodiments, a compound comprises a modified oligonucleotide attached to a ligand through a linker comprising one or more nucleosides. For the purposes of calculating percentage complementarity, any additional nucleosides of the linker are considered to be part of the linker and not part of the modified oligonucleotide. Accordingly, the nucleobase sequence of the modified oligonucleotide of a conjugated compound may still be 100% complementary to miR-122, even where the linker comprises one or more nucleosides that are not complementary to miR-122.

The miR-122 nucleobase sequences set forth herein, including but not limited to those found in the examples and in the sequence listing, are independent of any modification to the nucleic acid. As such, nucleic acids defined by a SEQ ID NO may comprise, independently, one or more modifications to one or more sugar moieties, to one or more internucleoside linkages, and/or to one or more nucleobases.

Although the sequence listing accompanying this filing identifies each nucleobase sequence as either "RNA" or "DNA" as required, in practice, those sequences may be modified with any combination of chemical modifications. One of skill in the art will readily appreciate that such designation as "RNA" or "DNA" to describe modified oligonucleotides is somewhat arbitrary. For example, a modified oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to, those in the sequence listing, are intended to encompass nucleic acids containing any combination of natural or modified RNA and/or DNA, including, but not limited to such nucleic acids having modified nucleobases. By way of further example and without limitation, a modified oligonucleotide having the nucleobase sequence "ATCGATCG" encompasses any oligonucleotide having such nucleobase sequence, whether modified or unmodified, including, but not limited to, such compounds comprising RNA bases, such as those having sequence "AUCGAUCG" and those having some DNA bases and some RNA bases such as "AUCGATCG" and oligonucleotides having other modified bases, such as "AT$^{me}$CGAUCG," wherein $^{me}$C indicates a 5-methylcytosine. Similarly, a modified oligonucleotide having the nucleobase sequence "AUCGAUCG" encompasses any oligonucleotide having such nucleobase sequence, whether modified or unmodified, including, but not limited to, such compounds comprising DNA bases, such as those having sequence "ATCGATCG" and those having some DNA bases and some RNA bases such as "AUCGATCG" and oligonucleotides having other modified bases, such as "AT$^{me}$C-GAUCG," wherein $^{me}$C indicates a 5-methylcytosine.

Certain Uses of miR-122 Compositions

The microRNA miR-122 is a liver-expressed microRNA that is a critical endogenous "host factor" for the replication of HCV, and oligonucleotides targeting miR-122 block HCV replication (Jopling et al. (2005) *Science* 309, 1577-81) Inhibition of miR-122 in chimpanzees chronically infected with the Hepatitis C virus reduced HCV RNA level. In HCV-infected patients, inhibition of miR-122 resulted in a mean 2 log reduction in HCV RNA level after 5 weekly doses of anti-miR-122 compound. The compounds described herein are potent inhibitors of miR-122 activity. Accordingly, provided here are methods for the treatment of HCV infection, comprising a compound provided herein to an HCV-infected subject.

Provided herein are methods for treating an HCV-infected subject comprising administering to the subject a compound provided herein. In certain embodiments, the methods provided herein comprise selecting an HCV-infected subject. In certain embodiments, the subject is a human.

In certain embodiments, the administering reduces the symptoms of HCV infection. Symptoms of HCV infection include, without limitation, pain over the liver, jaundice, nausea, loss of appetite, and fatigue.

Following an HCV treatment regimen, an HCV-infected subject may experience a decrease in HCV RNA level, followed by an increase in HCV RNA level, which subsequent increase is known as a rebound in HCV RNA level. In certain embodiments, the compounds and methods provided herein prevent a rebound in HCV RNA level. In certain embodiments, the compounds and methods provided herein delay a rebound in HCV RNA level.

HCV RNA level may be used to diagnose HCV infection, monitor disease activity and monitor a subject's response to treatment. In certain embodiments, administering a compound provided herein reduces HCV RNA level. In certain embodiments, a compound herein is administered at a dose that is sufficient to reduce HCV RNA level. In certain embodiments, the methods provided herein comprise selecting a subject having an HCV RNA level greater than 350,000 copies per milliliter of serum, between 350,000 and 3,500,000 copies per milliliter of serum, or greater than 3,500,000 copies per milliliter of serum. In certain embodiments, the methods provided herein comprise reducing HCV RNA level. In certain embodiments, the methods provided herein comprise reducing HCV RNA level to below 200 copies per milliliter of serum, to below 100 copies per milliliter of serum, or to below 40 copies per milliliter of serum. HCV RNA level may be referred to as "viral load" or "HCV RNA titer."

Changes to HCV RNA level may be described as log changes. For example, a drop from 60,000 to 600 would be a 2-log drop in HCV RNA level. In certain embodiments, the methods provided herein achieve a HCV RNA level decrease greater than or equal to 2 logs. In certain embodiments, the methods provided herein achieve an HCV RNA level decrease of at least 0.5 fold, at least 1.0 fold, at least 1.5 fold, at least 2.0 fold, or at least 2.5 fold.

In certain embodiments, the methods provided herein comprise achieving a sustained virological response.

HCV-infected subjects may develop HCV-associated diseases. The major hepatological consequence of HCV infection is cirrhosis and complications thereof including hemorrhage, hepatic insufficiency, and hepatocellular carcinoma. An additional complication is fibrosis, which is the result of chronic inflammation causing the deposition of extracellular matrix component, which leads to distortion of the hepatic architecture and blockage of the microcirculation and liver function. As cirrhosis progresses and the fibrotic tissue builds up, severe necroinflammatory activity ensues and steatosis begins. Steatosis leads to extrahepatic pathologies including diabetes, protein malnutrition, hypertension, cell toxins, obesity, and anoxia. As fibrosis and steatosis becomes severe the liver will eventually fail and require liver transplantation. HCV-infected subjects may also develop hepatocellular carcinoma. In certain embodiments, an HCV-infected subject has an HCV-associated disease. In certain embodiments, the HCV-associated disease is cirrhosis, fibrosis, steatohepatitis, steatosis, and/or hepatocellular carcinoma.

In certain embodiments, an HCV-infected subject has one or more diseases. In certain embodiments, an HCV-infected subject is infected with one or more viruses other than HCV. In certain embodiments, an HCV-infected subject is infected with human immunodeficiency virus (HIV). The compounds provided herein may be concomitantly administered with one or more additional therapeutic agents. In certain embodiments, the one or more additional therapeutic agents comprises an immune therapy, an immunomodulator, therapeutic vaccine, antifibrotic agent, anti-inflammatory agent, bronchodilator, mucolytic agent, anti-muscarinic, anti-leukotriene, inhibitor of cell adhesion, anti-oxidant, cytokine agonist, cytokine antagonist, lung surfactant, antimicrobial, antiviral agent, anti-HCV agent, an anti-cancer agent, an anti-miR-122 compound, an RNAi agent or a cyclophilin inhibitor.

In certain embodiments, the one or more additional therapeutic agents may be selected from a protease inhibitor, a polymerase inhibitor, a cofactor inhibitor, an RNA polymerase inhibitor, a structural protein inhibitor, a non-structural protein inhibitor, a cyclophilin inhibitor, an entry inhibitor, a TLR7 agonist, and an interferon.

In certain embodiments, the additional therapeutic agent is a modified oligonucleotide having the structure $C_LCA_LT$-$TG_LT_LCAC_LAC_LTC_LC_L$ (SEQ ID NO: 7), where nucleosides not followed by a subscript indicate β-D-deoxyribonucleosides; nucleosides followed by a subscript "L" indicate LNA nucleosides; and each internucleoside linkage is a phosphorothioate internucleoside linkage. In certain embodiments, a therapeutic agent is a GalNAc-conjugated $C_LCA_LTTG_LT_L$-$CAC_LAC_LTC_LC_L$ (SEQ ID NO: 7). In some embodiments, all of the $C_L$ nucleosides are $^{Me}C_L$ nucleosides, wherein the superscript "Me" indicates 5-methylcytosine.

In certain embodiments, the additional therapeutic agent is selected from a protease inhibitor, an NS5A inhibitor, an NS3/4A inhibitor, a nucleoside NS5B inhibitor, a nucleotide NS5B inhibitor, a non-nucleoside NS5B inhibitor, a cyclophilin inhibitor and an interferon.

In certain embodiments, the additional therapeutic agent is selected from interferon alfa-2a, interferon alpha-2b, interferon alfacon-1, peginterferon alpha-2b, peginterferon alpha-2a, interferon-alpha-2b extensed release, interferon lambda, sofosbuvir, ribavirin, telapravir, boceprevir, vaniprevir, asunaprevir, ritonavir, setrobuvir, daclastavir, simeprevir, alisporivir, mericitabine, tegobuvir, danoprevir, sovaprevir, and neceprevir. In certain embodiments, the additional therapeutic agent is selected from faldaprevir, ABT-450, MK-5172, mericitabine, ledipasvir, ombitasvir, GS-5816, MK-8742, dasabuvir, BMS-791325, and ABT-072.

In certain embodiments, the additional therapeutic agent is selected from an interferon, ribavirin, and telapravir. In certain embodiments, the interferon is selected from interferon alfa-2a, interferon alpha-2b, interferon alfacon-1, peginterferon alpha-2b, and peginterferon alpha-2a.

In certain embodiments, the additional therapeutic agent includes peginterferon alpha-2b and ribavirin. For example, a subject may receive a therapy that comprises a compound provided herein, peginterferon alpha-2b and ribavirin. In certain embodiments, the at least one additional therapeutic agent includes peginterferon alpha-2a and ribavirin. For example, a subject may receive a therapy that comprises a compound provided herein, peginterferon alpha-2a and ribavirin. In certain embodiments, the additional therapeutic agents are ombitasvir and ABT-450. In certain embodiments, the additional therapeutic agents are asunaprevir, daclatasvir, and BMS-791325. In certain embodiments, the additional therapeutic agents are sofosbuvir and ledipasivr. In certain embodiments, the additional therapeutic agents are MK-8742 and MK-5172.

Certain subjects receiving a certain therapy, for example interferon or ribaviran therapy, may not experience a significant or therapeutically beneficial reduction in HCV RNA level. Such subjects may benefit from administration of one or more additional therapeutic agents. In certain embodiments, a subject of the methods provided herein is a non-responder. In certain embodiments, a subject is an interferon non-responder. In certain embodiments, a subject is a direct-acting anti-viral non-responder.

In certain embodiments, an additional therapeutic agent is an anti-viral agent used in the treatment of HIV infection. In certain embodiments, an additional therapeutic agent is a non-nucleoside reverse transcriptase inhibitors (NNRTIs). In certain embodiments, an additional therapeutic agent is a nucleoside reverse transcriptase inhibitors (NRTIs). In certain embodiments, an additional therapeutic agent is a protease inhibitor. In certain embodiments, an additional therapeutic agent is an entry inhibitor or fusion inhibitor. In certain embodiments, an additional therapeutic agent is an integrase inhibitor. In certain embodiments, an additional therapeutic agent is selected from efavirenz, etravirine, nevirapine, abacavir, emtricitabine, tenofovir, lamivudine, zidovudine, atazanavir, darunavir, fosamprenavir, ritonavir, enfuvirtide, maraviroc, and raltegravir.

A subject infected with HCV may experience abnormal liver function, which is assessed by measuring one or more of bilirubin, albumin, and prothombin time. Measurement of the liver enzymes alanine aminotransferase (ALT), and aspartate aminotransferase (AST) is performed to assess liver inflammation. One or more abnormal levels of these markers may indicate abnormal liver function. In certain embodiments, the methods provided herein comprise normalizing liver function. In certain embodiments, the methods provided herein comprise normalizing liver enzyme levels.

In any of the methods provided, herein, the compound may be present in a pharmaceutical composition.

The compounds provided herein may be for use in therapy. In certain embodiments, the compound is for use in treating an HCV-infected subject. In certain embodiments, the subject is a human. The compound for use in treating an HCV-infected subject may, in certain embodiments, be for use in any method of treatment described herein.

Provided herein are methods comprising administering a compound provided herein to a subject having a miR-122-associated condition. In certain embodiments, a miR-122-associated condition is HCV infection.

In certain embodiments, a miR-122-associated condition is elevated cholesterol. In certain embodiments, administration of an anti-miR-122 compound to a subject results in reduced serum cholesterol. Accordingly, in certain embodiments, provided herein are methods of lowering cholesterol in a subject, comprising administering to a subject a compound provided herein. In certain embodiments, cholesterol levels may be used as a biomarker to assess the activity of an anti-miR-122 compound provided herein, alone or in addition to another indicator of efficacy, e.g. reduction in HCV RNA levels. Accordingly, provided herein are methods comprising administering a compound provided herein to a subject, collecting a blood sample from the subject, and measuring cholesterol in the blood sample from the subject. The level of cholesterol may be used as an indicator of anti-miR-122 compound activity in the subject.

In certain embodiments, a miR-122-associated condition is steatosis. Accordingly, in certain embodiments, provided herein are methods of reducing steatosis in a subject, comprising administering to the subject a compound provided herein.

In certain embodiments, a miR-122-associated condition is an iron overload disorder. An iron overload disorder may occur as a result of a genetic mutation that causes the body to absorb excess amounts of iron. An iron overload disorder may also have non-genetic causes, including but not limited to chronic blood transfusions, chronic hepatitis, or ingestion of an excess amount of iron. In certain embodiments, an iron overload disorder is selected from transfusional iron overload, dietary iron overload, hereditary hemochromatosis, sickle cell disease, thalassemia, X-linked sideroblastic anemia, pyruvate kinase deficiency, and glucose-6-phosphate dehydrogenase deficiency. In certain embodiments, an iron overload disorder is a hereditary hemochromatosis selected from hemochromatosis type 1, hemochromatosis type 2A, hemochromatosis type 2B, hemochromatosis type 3, hemochromatosis type 4 (or ferroportin disease), African hemochromatosis, neonatal hemochromatosis, aceruloplasminemia, and atransferrinemia. In certain embodiments, administration of a compound provided herein to a subject having an iron overload disorder results in reduction of excess iron in the body of the subject.

Certain Modifications

A modified oligonucleotide may comprise one or more modifications to a nucleobase, sugar, and/or internucleoside linkage. A modified nucleobase, sugar, and/or internucleoside linkage may be selected over an unmodified form because of desirable properties such as, for example, enhanced cellular uptake, enhanced affinity for other oligonucleotides or nucleic acid targets and increased stability in the presence of nucleases.

In certain embodiments, a modified oligonucleotide comprises one or more modified nucleosides. In certain embodiments, a modified nucleoside is a stabilizing nucleoside. An example of a stabilizing nucleoside is a 2'-modified nucleoside.

In certain embodiments, a modified nucleoside comprises a modified sugar moiety. In certain embodiments, a modified nucleoside comprising a modified sugar moiety comprises an unmodified nucleobase. In certain embodiments, a modified sugar comprises a modified nucleobase. In certain embodiments, a modified nucleoside is a 2'-modified nucleoside.

In certain embodiments, a 2'-modified nucleoside comprises a bicyclic sugar moiety. In certain such embodiments, the bicyclic sugar moiety is a D sugar in the alpha configuration. In certain such embodiments, the bicyclic sugar moiety is a D sugar in the beta configuration. In certain such embodiments, the bicyclic sugar moiety is an L sugar in the alpha configuration. In certain such embodiments, the bicyclic sugar moiety is an L sugar in the beta configuration.

In certain embodiments, the bicyclic sugar moiety comprises a bridge group between the 2' and the 4'-carbon atoms. In certain such embodiments, the bridge group comprises from 1 to 8 linked biradical groups. In certain embodiments, the bicyclic sugar moiety comprises from 1 to 4 linked biradical groups. In certain embodiments, the bicyclic sugar moiety comprises 2 or 3 linked biradical groups. In certain embodiments, the bicyclic sugar moiety comprises 2 linked biradical groups. Examples of such 4' to 2' sugar substituents, include, but are not limited to: $—[C(R_a)(R_b)]_n—$, $—[C(R_a)(R_b)]_n—O—$, $—C(R_aR_b)—N(R)—O—$ or, $—C(R_aR_b)—O—N(R)—$; 4'-$CH_2$-2', 4'-$(CH_2)_2$-2', 4'-$(CH_2)_3$-2; 4'-$(CH_2)$—O-2' (LNA); 4'-$(CH_2)$—S-2; 4'-$(CH_2)_2$—O-2' (ENA); 4'-CH($CH_3$)—O-2' (cEt) and 4'-CH($CH_2OCH_3$)—O-2', and analogs thereof (see, e.g., U.S. Pat. No. 7,399,845, issued on Jul. 15, 2008); 4'-C($CH_3$)($CH_3$)—O-2' and analogs thereof, (see, e.g., WO2009/006478, published Jan. 8, 2009); 4'-$CH_2$—N($OCH_3$)-2' and analogs thereof (see, e.g., WO2008/150729, published Dec. 11, 2008); 4'-$CH_2$—O—N($CH_3$)-2' (see, e.g., US2004/0171570, published Sep. 2, 2004); 4'-$CH_2$—O—N(R)-2', and 4'-$CH_2$—N(R)—O-2'-, wherein each R is, independently, H, a protecting group, or $C_1$-$C_{12}$ alkyl; 4'-$CH_2$—N(R)—O-2', wherein R is H, $C_1$-$C_{12}$ alkyl, or a protecting group (see, U.S. Pat. No. 7,427,672, issued on Sep. 23, 2008); 4'-$CH_2$—C(H)($CH_3$)-2' (see, e.g., Chattopadhyaya, et al., *J. Org. Chem.,* 2009, 74, 118-134); and 4'-$CH_2$—C(=$CH_2$)-2' and analogs thereof (see, published PCT International Application WO 2008/154401, published on Dec. 8, 2008).

In certain embodiments, such 4' to 2' bridges independently comprise 1 or from 2 to 4 linked groups independently selected from $—[C(R_a)(R_b)]_n—$, $—C(R_a)=C(R_b)—$, $—C(R_a)=N—$, $—C(=NR_a)—$, $—C(=O)—$, $—C(=S)—$, $—O—$, $—Si(R_a)_2—$, $—S(=O)_x—$, and $—N(R_a)—$;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$acyl (C(=O)—H), substituted acyl, CN, sulfonyl ($S(=O)_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl, or a protecting group.

Nucleosides comprising bicyclic sugar moieties are referred to as bicyclic nucleosides or BNAs. In certain embodiments, bicyclic nucleosides include, but are not limited to, (A) α-L-Methyleneoxy (4'-$CH_2$—O-2') BNA; (B) β-D-Methyleneoxy (4'-$CH_2$—O-2') BNA; (C) Ethyleneoxy (4'-$(CH_2)_2$—O-2') BNA; (D) Aminooxy (4'-$CH_2$—O—N(R)-2') BNA; (E) Oxyamino (4'-$CH_2$—N(R)—O-2') BNA; (F) Methyl(methyleneoxy) (4'-CH($CH_3$)—O-2') BNA (also referred to as constrained ethyl or cEt); (G) methylene-thio (4'-$CH_2$—S-2') BNA; (H) methylene-amino (4'-CH2-N(R)-2') BNA; (I) methyl carbocyclic (4'-$CH_2$—CH($CH_3$)-2') BNA; (J) c-MOE (4'-$CH_2$—OMe-2') BNA and (K) propylene carbocyclic (4'-$(CH_2)_3$-2') BNA as depicted below.

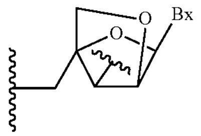
(A)

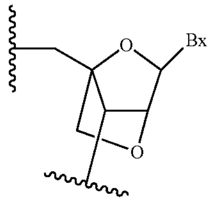
(B)

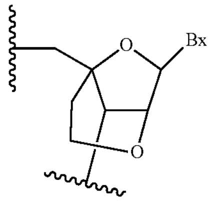
(C)

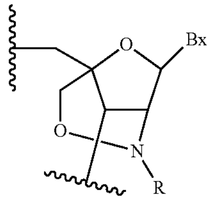
(D)

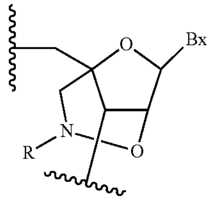
(E)

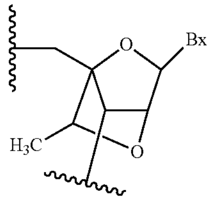
(F)

-continued (G)

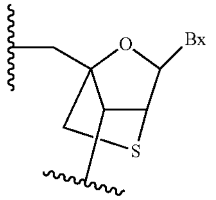

(H)

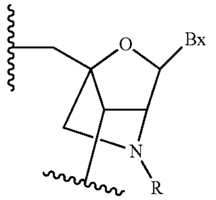

(I)

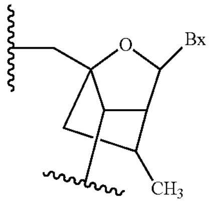

(J)

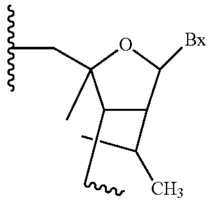

(K)

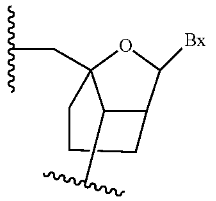

wherein Bx is a nucleobase moiety and R is, independently, H, a protecting group, or $C_1$-$C_{12}$ alkyl.

In certain embodiments, a 2'-modified nucleoside comprises a 2'-substituent group selected from halo, allyl, amino, azido, SH, CN, OCN, $CF_3$, $OCF_3$, O-, S-, or N($R_m$)-alkyl; O-, S-, or N($R_m$)-alkenyl; O-, S- or N($R_m$)-alkynyl; O-alkylenyl-O-alkyl, alkynyl, alkaryl, aralkyl, O-alkaryl, O-aralkyl, $O(CH_2)_2SCH_3$, O—$(CH_2)_2$—O—N($R_m$)($R_n$) or O—$CH_2$—C(═O)—N($R_m$)($R_n$), where each $R_m$ and $R_n$ is, independently, H, an amino protecting group or substituted or unsubstituted $C_1$-$C_{10}$ alkyl. These 2'-substituent groups can be further substituted with one or more substituent groups independently selected from hydroxyl, amino, alkoxy, carboxy, benzyl, phenyl, nitro ($NO_2$), thiol, thioalkoxy (S-alkyl), halogen, alkyl, aryl, alkenyl and alkynyl.

In certain embodiments, a 2'-modified nucleoside comprises a 2'-substituent group selected from F, $NH_2$, $N_3$, $OCF_3$, O—$CH_3$, $O(CH_2)_3NH_2$, $CH_2$—CH═$CH_2$, O—$CH_2$—CH═$CH_2$, $OCH_2CH_2OCH_3$, $O(CH_2)_2SCH_3$, O—$(CH_2)_2$—O—N($R_m$)($R_n$), —$O(CH_2)_2O(CH_2)_2N(CH_3)_2$, and N-substituted acetamide (O—$CH_2$—C(═O)—N($R_m$)($R_n$) where each $R_m$ and $R_n$ is, independently, H, an amino protecting group or substituted or unsubstituted $C_1$-$C_{10}$ alkyl.

In certain embodiments, a 2'-modified nucleoside comprises a 2'-substituent group selected from F, $OCF_3$, O—$CH_3$, $OCH_2CH_2OCH_3$, 2'-$O(CH_2)_2SCH_3$, O—$(CH_2)_2$—O—N$(CH_3)_2$, —$O(CH_2)_2O(CH_2)_2N(CH_3)_2$, and O—$CH_2$—C(═O)—N(H)$CH_3$.

In certain embodiments, a 2'-modified nucleoside comprises a 2'-substituent group selected from F, O—$CH_3$, and $OCH_2CH_2OCH_3$.

In certain embodiments, a 2'-modified nucleoside is a 4'-thio modified nucleoside. In certain embodiments, a 2'-modified nucleoside is a 4'-thio-2'-modified nucleoside. A 4'-thio modified nucleoside has a β-D-ribonucleoside where the 4'-O replaced with 4'-S. A 4'-thio-2'-modified nucleoside is a 4'-thio modified nucleoside having the 2'-OH replaced with a 2'-substituent group. Suitable 2'-substituent groups include 2'-$OCH_3$, 2'-O—$(CH_2)_2$—$OCH_3$, and 2'-F.

In certain embodiments, a modified oligonucleotide comprises one or more internucleoside modifications. In certain such embodiments, each internucleoside linkage of a modified oligonucleotide is a modified internucleoside linkage. In certain embodiments, a modified internucleoside linkage comprises a phosphorus atom.

In certain embodiments, a modified oligonucleotide comprises at least one phosphorothioate internucleoside linkage. In certain embodiments, each internucleoside linkage of a modified oligonucleotide is a phosphorothioate internucleoside linkage.

In certain embodiments, a modified internucleoside linkage does not comprise a phosphorus atom. In certain such embodiments, an internucleoside linkage is formed by a short chain alkyl internucleoside linkage. In certain such embodiments, an internucleoside linkage is formed by a cycloalkyl internucleoside linkages. In certain such embodiments, an internucleoside linkage is formed by a mixed heteroatom and alkyl internucleoside linkage. In certain such embodiments, an internucleoside linkage is formed by a mixed heteroatom and cycloalkyl internucleoside linkages. In certain such embodiments, an internucleoside linkage is formed by one or more short chain heteroatomic internucleoside linkages. In certain such embodiments, an internucleoside linkage is formed by one or more heterocyclic internucleoside linkages. In certain such embodiments, an internucleoside linkage has an amide backbone. In certain such embodiments, an internucleoside linkage has mixed N, O, S and $CH_2$ component parts.

In certain embodiments, a modified oligonucleotide comprises one or more modified nucleobases. In certain embodiments, a modified nucleobase is selected from 7-deazaguanine, 7-deazaadenine, hypoxanthine, xanthine, 7-methylguanine, 2-aminopyridine and 2-pyridone. In certain embodiments, a modified nucleobase is selected from 5-substituted pyrimidines, 6-azapyrimidines and N-2, N-6 and O-6 substituted purines, including 2 aminopropyladenine, 5-propynyluracil and 5-propynylcytosine.

In certain embodiments, a modified nucleobase comprises a polycyclic heterocycle. In certain embodiments, a modified nucleobase comprises a tricyclic heterocycle. In certain embodiments, a modified nucleobase comprises a phenoxazine derivative. In certain embodiments, the phenoxazine can be further modified to form a nucleobase known in the art as a G-clamp.

In certain such embodiments, the compound comprises a modified oligonucleotide having one or more stabilizing groups that are attached to one or both termini of a modified oligonucleotide to enhance properties such as, for example, nuclease stability. Included in stabilizing groups are cap structures. These terminal modifications protect a modified oligonucleotide from exonuclease degradation, and can help in delivery and/or localization within a cell. The cap can be present at the 5'-terminus (5'-cap), or at the 3'-terminus (3'-cap), or can be present on both termini. Cap structures include, for example, inverted deoxy abasic caps.

Suitable cap structures include a 4',5'-methylene nucleotide, a 1-(beta-D-erythrofuranosyl) nucleotide, a 4'-thio nucleotide, a carbocyclic nucleotide, a 1,5-anhydrohexitol nucleotide, an L-nucleotide, an alpha-nucleotide, a modified base nucleotide, a phosphorodithioate linkage, a threo-pentofuranosyl nucleotide, an acyclic 3',4'-seco nucleotide, an acyclic 3,4-dihydroxybutyl nucleotide, an acyclic 3,5-dihydroxypentyl nucleotide, a 3'-3'-inverted nucleotide moiety, a 3'-3'-inverted abasic moiety, a 3'-2'-inverted nucleotide moiety, a 3'-2'-inverted abasic moiety, a 1,4-butanediol phosphate, a 3'-phosphoramidate, a hexylphosphate, an aminohexyl phosphate, a 3'-phosphate, a 3'-phosphorothioate, a phosphorodithioate, a bridging methylphosphonate moiety, and a non-bridging methylphosphonate moiety 5'-aminoalkyl phosphate, a 1,3-diamino-2-propyl phosphate, 3-aminopropyl phosphate, a 6-aminohexyl phosphate, a 1,2-aminododecyl phosphate, a hydroxypropyl phosphate, a 5'-5'-inverted nucleotide moiety, a 5'-5'-inverted abasic moiety, a 5'-phosphoramidate, a 5'-phosphorothioate, a 5'-amino, a bridging and/or non-bridging 5'-phosphoramidate, a phosphorothioate, and a 5'-mercapto moiety.

Certain Synthesis Methods

Modified oligonucleotides may be made with automated, solid phase synthesis methods known in the art. During solid phase synthesis, phosphoramidite monomers are sequentially coupled to a nucleoside that is covalently linked to a solid support. This nucleoside is the 3' terminal nucleoside of the modified oligonucleotide. Typically, the coupling cycle comprises four steps: detritylation (removal of a 5'-hydroxyl protecting group with acid), coupling (attachment of an activated phosphoroamidite to the support bound nucleoside or oligonucleotide), oxidation or sulfurization (conversion of a newly formed phosphite trimester with an oxidizing or sulfurizing agent), and capping (acetylation of unreacted 5'-hydroxyl groups). After the final coupling cycle, the solid support-bound oligonucleotide is subjected to a detritylation step, followed by a cleavage and deprotection step that simultaneously releases the oligonucleotide from the solid support and removes the protecting groups from the bases. The solid support is removed by filtration, the filtrate is concentrated and the resulting solution is tested for identity and purity. The oligonucleotide is then purified, for example using a column packed with anion-exchange resin.

GalNAc-conjugated modified oligonucleotides may be made with automated solid phase synthesis, similar to the solid phase synthesis that produced unconjugated oligonucleotides. During the synthesis of GalNAc-conjugated oligonucleotides, the phosphoramidite monomers are sequentially coupled to a GalNAc conjugate which is covalently linked to a solid support. The synthesis of GalNAc conjugates and GalNAc conjugate solid support is described, for example, in U.S. Pat. No. 8,106,022, and International Application Publication No. WO 2013/033230, each of which is herein incorporated by reference in its entirety for the description of the synthesis of carbohydrate-containing conjugates, including conjugates comprising one or more GalNAc moieties, and of the synthesis of conjugate covalently linked to solid support.

Certain Pharmaceutical Compositions

Any of the compounds provided herein may be prepared as a pharmaceutical composition. In certain embodiments, a pharmaceutical composition is administered in the form of a dosage unit (e.g., tablet, capsule, bolus, etc.). In some embodiments, a pharmaceutical composition comprises a compound provided herein at a dose within a range selected from 25 mg to 800 mg, 25 mg to 700 mg, 25 mg to 600 mg, 25 mg to 500 mg, 25 mg to 400 mg, 25 mg to 300 mg, 25 mg to 200 mg, 25 mg to 100 mg, 100 mg to 800 mg, 200 mg to 800 mg, 300 mg to 800 mg, 400 mg to 800 mg, 500 mg to 800 mg, 600 mg to 800 mg, 100 mg to 700 mg, 150 mg to 650 mg, 200 mg to 600 mg, 250 mg to 550 mg, 300 mg to 500 mg, 300 mg to 400 mg, and 400 mg to 600 mg. In certain embodiments, such pharmaceutical compositions comprise a compound provided herein present at a dose selected from 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 270 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, and 800 mg. In certain such embodiments, a pharmaceutical composition of the comprises a dose compound provided herein selected from 25 mg, 50 mg, 75 mg, 100 mg, 150 mg, 200 mg, 250 mg, 300 mg, 350 mg, 400 mg, 500 mg, 600 mg, 700 mg, and 800 mg.

In certain embodiments, a pharmaceutical composition comprising a compound provided herein is administered at a dose of 10 mg/kg or less, 9 mg/kg or less, 8 mg/kg or less, 7.5 mg/kg or less, 7 mg/kg or less, 6.5 mg/kg or less, 6 mg/kg or less, 5.5 mg/kg or less, 5 mg/kg or less, 4.5 mg/kg or less, 4 mg/kg or less, 3.5 mg/kg or less, 3 mg/kg or less, 2.5 mg/kg or less, 2 mg/kg or less, 1.5 mg/kg or less, 1 mg/kg or less, 0.75 mg/kg or less, 0.5 mg/kg or less, or 0.25 mg/kg or less.

In certain embodiments, a pharmaceutical agent is sterile lyophilized compound that is reconstituted with a suitable diluent, e.g., sterile water for injection or sterile saline for injection. The reconstituted product is administered as a subcutaneous injection or as an intravenous infusion after dilution into saline. The lyophilized drug product consists of a compound which has been prepared in water for injection, or in saline for injection, adjusted to pH 7.0-9.0 with acid or base during preparation, and then lyophilized. The lyophilized compound may be 25-800 mg of an oligonucleotide. It is understood that this encompasses 25, 50, 75, 100, 125, 150, 175, 200, 225, 250, 275, 300, 325, 350, 375, 425, 450, 475, 500, 525, 550, 575, 600, 625, 650, 675, 700, 725, 750, 775, and 800 mg of modified lyophilized oligonucleotide. Further, in some embodiments, the lyophilized compound is present in an amount that ranges from 25 mg to 800 mg, 25 mg to 700 mg, 25 mg to 600 mg, 25 mg to 500 mg, 25 mg to 400 mg, 25 mg to 300 mg, 25 mg to 200 mg, 25 mg to 100 mg, 100 mg to 800 mg, 200 mg to 800 mg, 300 mg to 800 mg, 400 mg to 800 mg, 500 mg to 800 mg, 600 mg to 800 mg, 100 mg to 700 mg, 150 mg to 650 mg, 200 mg to 600 mg, 250 mg to 550 mg, 300 mg to 500 mg, 300 mg to 400 mg, or 400 mg to 600 mg. The lyophilized drug product may be packaged in a 2 mL Type I, clear glass vial (ammonium sulfate-treated), stoppered with a bromobutyl rubber closure and sealed with an aluminum FLIP-OFF® overseal.

In certain embodiments, a pharmaceutical composition provided herein comprises a compound in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, the pharmaceutical compositions provided herein may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the oligonucleotide(s) of the formulation.

Lipid moieties have been used in nucleic acid therapies in a variety of methods. In one method, the nucleic acid is introduced into preformed liposomes or lipoplexes made of mixtures of cationic lipids and neutral lipids. In another method, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, INTRALIPID is used to prepare a pharmaceutical composition comprising an oligonucleotide. Intralipid is fat emulsion prepared for intravenous administration. It is made up of 10% soybean oil, 1.2% egg yolk phospholipids, 2.25% glycerin, and water for injection. In addition, sodium hydroxide has been added to adjust the pH so that the final product pH range is 6 to 8.9.

In certain embodiments, a pharmaceutical composition provided herein comprises a polyamine compound or a lipid moiety complexed with a nucleic acid. Such preparations are described in PCT publication WO/2008/042973, which is herein incorporated by reference in its entirety for the disclosure of lipid preparations. Certain additional preparations are described in Akinc et al., Nature Biotechnology 26, 561-569 (1 May 2008), which is herein incorporated by reference in its entirety for the disclosure of lipid preparations.

In certain embodiments, pharmaceutical compositions provided herein comprise one or more compounds and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein is prepared using known techniques, including, but not limited to mixing, dissolving, granulating, dragee-making, levigating, emulsifying, encapsulating, entrapping or tableting processes.

In certain embodiments, a pharmaceutical composition provided herein is a liquid (e.g., a suspension, elixir and/or solution). In certain of such embodiments, a liquid pharmaceutical composition is prepared using ingredients known in the art, including, but not limited to, water, glycols, oils, alcohols, flavoring agents, preservatives, and coloring agents.

In certain embodiments, a pharmaceutical composition provided herein is a solid (e.g., a powder, tablet, and/or capsule). In certain of such embodiments, a solid pharmaceutical composition comprising one or more oligonucleotides is prepared using ingredients known in the art, including, but not limited to, starches, sugars, diluents, granulating agents, lubricants, binders, and disintegrating agents.

In certain embodiments, a pharmaceutical composition provided herein is formulated as a depot preparation. Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more compounds provided herein to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein comprises a sustained-release system. A non-limiting example of such a sustained-release system is a semi-permeable matrix of solid hydrophobic polymers. In certain embodiments, sustained-release systems may, depending on their chemical nature, release pharmaceutical agents over a period of hours, days, weeks or months.

In certain embodiments, a pharmaceutical composition provided herein is prepared for oral administration. In certain of such embodiments, a pharmaceutical composition is formulated by combining one or more compounds comprising a modified oligonucleotide with one or more pharmaceutically acceptable carriers. Certain of such carriers enable pharmaceutical compositions to be formulated as tablets, pills, dragees, capsules, liquids, gels, syrups, slurries, suspensions and the like, for oral ingestion by a subject. In certain embodiments, pharmaceutical compositions for oral use are obtained by mixing oligonucleotide and one or more solid excipient. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum 8tragacanth, methyl cellulose, hydroxypropylmethyl-cellulose, sodium carboxymethylcellulose, and/or polyvinylpyrrolidone (PVP). In certain embodiments, such a mixture is optionally ground and auxiliaries are optionally added. In certain embodiments, pharmaceutical compositions are formed to obtain tablets or dragee cores. In certain embodiments, disintegrating agents (e.g., cross-linked polyvinyl pyrrolidone, agar, or alginic acid or a salt thereof, such as sodium alginate) are added.

In certain embodiments, dragee cores are provided with coatings. In certain such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical compositions for oral administration are push-fit capsules made of gelatin. Certain of such push-fit capsules comprise one or more pharmaceutical agents of the present invention in admixture with one or more filler such as lactose, binders such as starches, and/or lubricants such as talc or magnesium stearate and, optionally, stabilizers. In certain embodiments, pharmaceutical compositions for oral administration are soft, sealed capsules made of gelatin and a plasticizer, such as glycerol or sorbitol. In certain soft capsules, one or more pharmaceutical agents of the present invention are be dissolved or suspended in suitable liquids, such as fatty oils, liquid paraffin, or liquid polyethylene glycols. In addition, stabilizers may be added.

In certain embodiments, pharmaceutical compositions are prepared for buccal administration. Certain of such pharmaceutical compositions are tablets or lozenges formulated in conventional manner In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, one or more modified oligonucleotides provided herein is administered as a prodrug. In certain embodiments, upon in vivo administration, a prodrug is chemically or enzymatically converted to the biologically, pharmaceutically or therapeutically more active form of an oligonucleotide. In certain embodiments, prodrugs are useful because they are easier to administer than the corresponding active form. For example, in certain instances, a prodrug may be more bioavailable (e.g., through oral administration) than is the corresponding active form. In certain embodiments, prodrugs possess superior transmittal across cell membranes. In certain embodiments, a prodrug facilitates delivery of a modified oligonucleotide to the desired cell type, tissue, or organ. In certain embodiments, a prodrug is a compound comprising a conjugated modified oligonucleotide. In certain instances, a prodrug may have improved solubility compared to the corresponding active form. In certain embodiments, prodrugs are less water soluble than the corresponding active form. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form. In certain embodiments, a prodrug is produced by modifying a pharmaceutically active compound such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

Certain Routes of Administration

In certain embodiments, administering to a subject comprises parenteral administration. In certain embodiments, administering to a subject comprises intravenous administration. In certain embodiments, administering to a subject comprises subcutaneous administration.

In certain embodiments, administering to a subject comprises intraarterial, pulmonary, oral, rectal, transmucosal, intestinal, enteral, topical, transdermal, suppository, intrathecal, intraventricular, intraperitoneal, intranasal, intraocular, intramuscular, intramedullary, and intratumoral administration.

Certain miR-122 Kits

The present invention also provides kits. In some embodiments, the kits comprise one or more compounds provided herein. In some embodiments, a compound provided herein is present within a vial. A plurality of vials, such as 10, can be present in, for example, dispensing packs. In some embodiments, the vial is manufactured so as to be accessible with a syringe. The kit can also contain instructions for using the compounds provided herein.

In some embodiments, the kits may be used for administration of a compound provided herein to a subject. In such instances, in addition to comprising at least one compound provided herein, the kit can further comprise one or more of the following: syringe, alcohol swab, cotton ball, and/or gauze pad. In some embodiments, the compounds complementary to miR-122 can be present in a pre-filled syringe (such as a single-dose syringes with, for example, a 27 gauge, ½ inch needle with a needle guard), rather than in a vial. A plurality of pre-filled syringes, such as 10, can be present in, for example, dispensing packs. The kit can also contain instructions for administering a compound provided herein.

Certain Experimental Models

In certain embodiments, the present invention provides methods of using and/or testing a compound provided herein in an experimental model. Those having skill in the art are able to select and modify the protocols for such experimental models to evaluate a compound provided herein.

The effects of antisense inhibition of a microRNA following the administration of anti-miR compounds may be assessed by a variety of methods known in the art. In certain embodiments, these methods are be used to quantitate microRNA levels in cells or tissues in vitro or in vivo. In certain embodiments, changes in microRNA levels are measured by microarray analysis. In certain embodiments, changes in microRNA levels are measured by one of several commercially available PCR assays, such as the TaqMan® MicroRNA Assay (Applied Biosystems, a Life Technologies brand).

In vitro activity of anti-miR compounds may be assessed using a luciferase cell culture assay. In this assay, a microRNA luciferase sensor construct is engineered to contain one or more binding sites of the microRNA of interest fused to a luciferase gene. When the microRNA binds to its cognate site in the luciferase sensor construct, luciferase expression is suppressed. When the appropriate anti-miR is introduced into the cells, it binds to the target microRNA and relieves suppression of luciferase expression. Thus, in this assay anti-miRs that are effective inhibitors of the microRNA of interest will cause an increase in luciferase expression.

Activity of anti-miR compounds may be assessed by measuring the mRNA and/or protein level of a target of a microRNA. A microRNA binds to a complementary site within one or more target RNAs, leading to suppression of a target RNA, thus inhibition of the microRNA results in the increase in the level of mRNA and/or protein of a target of the microRNA (i.e., derepression). The derepression of one or more target RNAs may be measured in vivo or in vitro. For example, a target of miR-122 is aldolase A (ALDOA) Inhibition of miR-122 results in an increase in the level of ALDOA mRNA, thus ALDOA mRNA levels may be used to evaluate the inhibitory activity of an anti-miR-122 compound.

The effects of anti-miR-122 compounds on HCV replication may be measured in an HCV replicon assay. In this assay, compounds are introduced into a cell line (e.g., a human hepatoma cell line) that contains a subgenomic replicon of HCV with a stable luciferase reporter and three cell culture-adaptive mutations (luc-ubi-neo/ET). The luciferase reporter is used as an indirect measure of HCV replication. The replicon used may be a parent HCV genotype or an HCV genotype with mutations that confer resistance to anti-viral agents. Anti-miR-122 compounds may be evaluated alone or in combination with other agents used in the treatment of HCV-infection. In some embodiments, a modified oligonucleotide may be tested in an in vivo or in vitro assay, and subsequently conjugated to form a compound for use in the methods described herein.

EXAMPLES

The following examples are presented in order to more fully illustrate some embodiments of the invention. They should, in no way be construed, however, as limiting the broad scope of the invention. Those of ordinary skill in the art will readily adopt the underlying principles of this discovery to design various compounds without departing from the spirit of the current invention.

Example 1

Design and Evaluation of Anti-miR-122 Compounds

To identify potent inhibitors of miR-122, numerous anti-miR-122 modified oligonucleotides were designed and synthesized. The modified oligonucleotides varied in length, and in the number, placement, and identity of bicyclic nucleosides and non-bicyclic nucleosides. The compounds were evaluated in a number of assays, to identify anti-miRs that are suitable therapeutic agents for the treatment of HCV infection. The evaluation of the compounds was performed in an iterative manner, in which highly active compounds were further optimized through design changes, and the resultant compounds were then subjected to additional screening. The compound evaluation process included assessment of potency, safety, and physicochemical characteristics.

In total, over 400 anti-miR-122 modified oligonucleotides were designed and tested in a first luciferase cell culture activity assay. Following an additional luciferase assay and for certain compounds measurement of metabolic stability, approximately 70 of these compounds were selected for further in vivo testing. Of these 70 compounds approximately 10 compounds were identified as having a suitable in vivo potency (e.g. an $ED_{50}$ of less than 5 mg/kg). A subset of these compounds was identified as having a certain safety profile in rodents and non-human primates. Thus, of the hundreds of compounds screened, only a small subset of the initial over 400 compounds met certain potency, safety and physicochemical criteria.

Certain anti-miR-122 compounds are shown in Table A. The "position on miR-122" is the position to which the nucleoside in that column is complementary to SEQ ID NO: 1, counting from the 5' end SEQ ID NO: 1.

TABLE A

Certain Anti-miR-122 Compounds

| Cmpd # Position on miR-122 | 22 | 21 | 20 | 19 | 18 | 17 | 16 | 15 | 14 | 13 | 12 | 11 | 10 | 9 | 8 | 7 | 6 | 5 | 4 | 3 | 2 | 1 | SEQ ID NO |
|---|---|---|---|---|---|---|---|---|---|---|---|---|---|---|---|---|---|---|---|---|---|---|---|
| | SEQUENCE (5' to 3') and MODIFICATIONS | | | | | | | | | | | | | | | | | | | | | | |
| 38011 | | | | | | | $C_S$ | C | A | $U_S$ | T | $G_S$ | $U_S$ | C | A | $C_S$ | A | $C_S$ | T | $C_S$ | $C_S$ | A | 3 |
| 38012 | | | | | | | $C_S$ | C | $A_S$ | T | T | G | $U_S$ | $C_S$ | A | $C_S$ | A | $C_S$ | T | $C_S$ | $C_S$ | A | 3 |
| 38013 | | | | | | | $C_S$ | C | A | $U_S$ | T | $G_S$ | T | $C_S$ | A | $C_S$ | A | $C_S$ | T | $C_S$ | $C_S$ | A | 3 |
| 38014 | | | | | | | $C_S$ | C | A | $U_S$ | T | $G_S$ | $U_S$ | C | A | $C_S$ | A | $C_S$ | T | $C_S$ | $C_S$ | $A_E$ | 3 |
| 38015 | | | | | | | $^{Me}C_S$ | C | A | $T_S$ | T | $G_S$ | $T_S$ | C | A | $^{Me}C_S$ | A | $^{Me}C_S$ | T | $^{Me}C_S$ | $^{Me}C_S$ | $A_E$ | 3 |
| 38016 | | | | | | | $^{Me}C_S$ | C | A | $T_S$ | T | G | $T_S$ | $^{Me}C_S$ | A | $^{Me}C_S$ | A | $^{Me}C_S$ | T | $^{Me}C_S$ | $^{Me}C_S$ | $A_E$ | 3 |
| 38021 | | | | | | | CL | C | A | TL | T | G | TL | CL | A | CL | A | CL | T | CL | CL | | 4 |
| 38646 | | | | $A_E$ | $^{Me}C_E$ | $A_E$ | $^{Me}C_E$ | C | $A_S$ | T | T | G | $U_S$ | $C_S$ | A | $C_S$ | A | $C_S$ | T | $C_S$ | $C_S$ | | 4 |
| 38647 | | | | $A_E$ | $^{Me}C_E$ | $A_E$ | $^{Me}C_E$ | $^{Me}C_E$ | $A_S$ | T | T | G | $U_S$ | $C_S$ | A | $C_S$ | A | $C_S$ | T | $C_S$ | $C_S$ | | 4 |
| 38648 | | | | $A_E$ | $^{Me}C_E$ | $A_E$ | $^{Me}C_E$ | $^{Me}C_E$ | $A_E$ | T | T | G | $U_S$ | $C_S$ | A | $C_S$ | A | $C_S$ | T | $C_S$ | $C_S$ | | 4 |
| 38649 | | | | $A_E$ | $^{Me}C_E$ | $A_E$ | $^{Me}C_E$ | $^{Me}C_E$ | $A_E$ | $T_E$ | T | G | $U_S$ | $C_S$ | A | $C_S$ | A | $C_S$ | T | $C_S$ | $C_S$ | | 4 |
| 38650 | | | | $A_E$ | $^{Me}C_E$ | $A_E$ | $^{Me}C_E$ | $^{Me}C_E$ | $A_E$ | $T_E$ | $T_E$ | G | $U_S$ | $C_S$ | A | $C_S$ | A | $C_S$ | T | $C_S$ | $C_S$ | | 4 |
| 38651 | | | | $A_E$ | $^{Me}C_E$ | $A_E$ | $^{Me}C_E$ | $^{Me}C_E$ | $A_E$ | $T_E$ | $T_E$ | $G_E$ | $U_S$ | $C_S$ | A | $C_S$ | A | $C_S$ | T | $C_S$ | $C_S$ | | 4 |
| 38652 | $^{Me}C_E$ | $A_E$ | $A_E$ | $A_E$ | $^{Me}C_E$ | $A_E$ | $C_S$ | C | $A_S$ | T | T | G | $U_S$ | $C_S$ | A | $C_S$ | A | $C_S$ | T | $C_S$ | $C_S$ | | 5 |
| 38660 | $^{Me}C_E$ | $A_E$ | $A_E$ | $A_E$ | $^{Me}C_E$ | $A_E$ | $C_S$ | C | $A_S$ | T | T | G | $U_S$ | $C_S$ | A | $C_S$ | A | $C_S$ | T | $C_S$ | $C_S$ | $T_E$ | 6 |
| 38872 | | | | | | | $C_S$ | C | A | $U_S$ | T | G | $U_S$ | $C_S$ | A | $C_S$ | A | $C_S$ | T | $C_S$ | $C_S$ | A | 3 |
| 38910 | | | | | | | $^{Me}C_E$ | $C_S$ | A | $U_S$ | T | G | $U_S$ | $C_S$ | A | $C_S$ | A | $C_S$ | T | $C_S$ | $C_S$ | $A_E$ | 3 |

Sugar moieties are indicated as follows: nucleosides not followed by a subscript indicate β-D-deoxyribonucleosides; nucleosides followed by a subscript "E" indicate 2'-MOE nucleosides; nucleosides followed by a subscript "S" indicate S-cEt nucleosides; nucleosides followed by a subscript "L" indicate LNA nucleosides. Each internucleoside linkage is a phosphorothioate internucleoside linkage. Superscript "Me" indicates a 5-methyl group on the base of the nucleoside.

Potency

In Vitro and In Vivo Potency

An in vitro luciferase assay was used to measure the ability of each compound to inhibit the activity of miR-122 in cell culture. In this assay, a microRNA luciferase sensor construct was engineered to contain multiple miR-122 binding sites fused to a luciferase gene. When miR-122 binds to its targetsites in the luciferase sensor construct, luciferase expression is suppressed. When an active anti-miR-122 compound is introduced into the cells, it binds to miR-122 and relieves suppression of luciferase expression. Thus, in this assay anti-miR-122 compounds that are effective inhibitors of the miR-122 will cause an increase in luciferase expression.

The luciferase sensor construct, and a second construct expressing miR-122, were introduced into Hela cells. Anti-miR-122 compounds were transfected into the cells at several different concentrations. Compounds with an $EC_{50}$ of less than 100 nM were subjected to an additional luciferase assay, at a broader range of anti-miR concentrations than in the initial luciferase assay, to confirm activity. Compounds were tested in two separate experiments, as indicated in Table B. The mean EC50 for each compound is shown in Table B. The results demonstrate that alterations to sugar moiety or nucleobase can impact in vitro potency of an anti-miR-122 compound.

TABLE B

Mean EC50 in the luciferase cell culture assay

| Compound # | Sequence and Chemistry | SEQ ID NO | Experiment # | Luciferase mean $EC_{50}$ |
|---|---|---|---|---|
| 38011 | $C_SCAU_STG_SU_SCAC_SAC_STC_SC_SA$ | 3 | 1 | 38.45 |
| 38012 | $C_SCA_STTGU_SC_SAC_SAC_STC_SC_SA$ | 3 | 1 | 43.78 |
| 38013 | $C_SCAU_STG_STC_SAC_SAC_STC_SC_SA$ | 3 | 1 | 53.27 |

TABLE B-continued

| Mean EC50 in the luciferase cell culture assay | | | | |
|---|---|---|---|---|
| Compound # | Sequence and Chemistry | SEQ ID NO | Experiment # | Luciferase mean $EC_{50}$ |
| 38014 | $C_SCAU_STG_SU_SCAC_SAC_STC_SC_SA_E$ | 3 | 1 | 42.71 |
| 38015 | $^{Me}C_SCAT_STG_ST_SCA^{Me}C_SA^{Me}C_ST^{Me}C_S{}^{Me}C_SA_E$ | 3 | 1 | 42.40 |
| 38016 | $^{Me}C_SCAT_STGT_S{}^{Me}C_SA^{Me}C_SA^{Me}C_ST^{Me}C_S{}^{Me}C_SA_E$ | 3 | 1 | 14.07 |
| 38021 | $^{Me}C_LCAT_LTGT_L{}^{Me}C_LA^{Me}C_LA^{Me}C_LT^{Me}C_L{}^{Me}C_LA_E$ | 3 | 1 | 11.18 |
| 38872 | $C_SCAU_STGU_SC_SAC_SAC_STC_SC_SA$ | 3 | 2 | 18.3 |
| 38910 | $^{Me}CC_SAU_STGU_SC_SAC_SAC_STC_SC_SA_E$ | 3 | Not tested | |
| 38646 | $A_E{}^{Me}C_EA_E{}^{Me}C_ECA_STTGU_SC_SAC_SAC_STC_SC_S$ | 4 | 2 | 77.15 |
| 38647 | $A_E{}^{Me}C_EA_E{}^{Me}C_E{}^{Me}C_EA_STTGU_SC_SAC_SAC_STC_SC_S$ | 4 | 2 | 57.44 |
| 38648 | $A_E{}^{Me}C_EA_E{}^{Me}C_E{}^{Me}C_EA_ETTGU_SC_SAC_SAC_STC_SC_S$ | 4 | 2 | 97.68 |
| 38649 | $A_E{}^{Me}C_EA_E{}^{Me}C_E{}^{Me}C_EA_ET_ETGU_SC_SAC_SAC_STC_SC_S$ | 4 | 2 | 46.76 |
| 38650 | $A_E{}^{Me}C_EA_E{}^{Me}C_E{}^{Me}C_EA_ET_ET_EGU_SC_SAC_SAC_STC_SC_S$ | 4 | 2 | 28.16 |
| 38651 | $A_E{}^{Me}C_EA_E{}^{Me}C_E{}^{Me}C_EA_ET_ET_EG_EU_SC_SAC_SAC_STC_SC_S$ | 4 | 2 | 26.12 |
| 38652 | $^{Me}C_EA_EA_EA_E{}^{Me}C_EA_EC_SCA_STTGU_SC_SAC_SAC_STC_SC_S$ | 5 | 2 | 31.86 |
| 38659 | $C_SCA_STTGU_SC_SAC_SAC_STC_SC_ST_E$ | 10 | 2 | 130.01 |
| 38660 | $^{Me}C_EA_EA_EA_E{}^{Me}C_EA_EC_SCA_STTGU_SC_SAC_SAC_STC_SC_ST_E$ | 6 | 2 | 17.02 |

To determine in vivo potency, certain compounds were evaluated for their ability to de-repress the expression of liver aldolase A (ALDOA), a gene that is normally suppressed by miR-122 activity. Inhibition of miR-122 leads to an increase in ALDOA expression, thus ALDOA mRNA levels can be used to measure miR-122 inhibitory activity in vivo. Compounds were administered to mice in a single dose at the amounts indicated in Table C, and after 7 days the study was terminated, and ALDOA mRNA levels were measured, by quantitative PCR, in RNA isolated from liver. Except for compound 38910, each compound in Table C was tested in the same study. The fold change in ALDOA mRNA, relative to saline, was calculated to determine in vivo potency ("ND" indicates "not determined).

TABLE C

| Comparison of anti-miR-122 compound structure and potency | | | | | |
|---|---|---|---|---|---|
| | | | Fold change in ALDOA relative to saline | | |
| Compound # | Sequence and Chemistry | SEQ ID | 1 mg/kg | 3 mg/kg | 10 mg/kg |
| 38011 | $C_SCAU_STG_SU_SCAC_SAC_STC_SC_SA$ | 3 | 1.47 | 2.10 | 3.89 |
| 38012 | $C_SCA_STTGU_SC_SAC_SAC_STC_SC_SA$ | 3 | 1.79 | 4.69 | 4.57 |
| 38013 | $C_SCAU_STG_STC_SAC_SAC_STC_SC_SA$ | 3 | 1.31 | 1.61 | 2.55 |
| 38014 | $C_SCAU_STG_SU_SCAC_SAC_STC_SC_SA_E$ | 3 | 1.16 | 1.82 | 2.94 |
| 38015 | $^{Me}C_SCAT_STG_ST_SCA^{Me}C_SA^{Me}C_ST^{Me}C_S{}^{Me}C_SA_E$ | 3 | 1.43 | 1.64 | 1.82 |
| 38016 | $^{Me}C_SCAT_STGT_S{}^{Me}C_SA^{Me}C_SA^{Me}C_ST^{Me}C_S{}^{Me}C_SA_E$ | 3 | 1.43 | 2.34 | 4.18 |
| 38021 | $^{Me}C_LCAT_LTGT_L{}^{Me}C_LA^{Me}C_LA^{Me}C_LT^{Me}C_L{}^{Me}C_LA_E$ | 3 | 1.46 | 3.01 | 3.91 |
| 38872 | $C_SCAU_STGU_SC_SAC_SAC_STC_SC_SA$ | 3 | 1.80 | 4.04 | 4.89 |
| 38910 | $^{Me}CC_SAU_STGU_SC_SAC_SAC_STC_SC_SA_E$ | 3 | ND | 2.35 | 3.26 |

As can be seen in Table C, single changes in the placement of a sugar moiety or nucleobase can have an impact on in vivo potency. For example, the only difference between 38872 and 38011 is the placement of a cEt sugar moiety, however the in vivo potency of 0011 is significantly lower than that of 38872, with a comparable level of ALDOA de-repression reached only at the higher dose of 10 mg/kg of 38011 compared to the 3 mg/kg dose for compound 38872. Compound 38021, relative to 38016, has LNA in place of cEt sugar moieties, and has a similar potency to 38016, thus this difference did not impact potency. Of this group of compounds, compounds 38012, 38016, 38021 and 38872 were identified as active compounds.

Additional studies were performed to evaluate certain additional anti-miR-122 compounds. The results of these studies are shown in Table D. Compounds 38646, 38647, 38648, 38649, 38650, 38651, and 38652 were tested together in one in vivo study, and compounds 38659 and 38660 were tested together in another in vivo study.

TABLE D

Comparison of anti-miR-122 compound structure and potency

| Compound # | Sequence and Structure | SEQ ID | Luciferase mean $EC_{50}$ | Fold change in ALDOA relative to saline 3 mg/kg | 10 mg/kg |
|---|---|---|---|---|---|
| 38646 | $A_E{}^{Me}C_EA_E{}^{Me}C_ECA_STTGU_SC_SAC_SAC_STC_SC_S$-- | 4 | 77.15 | ND | ND |
| 38647 | $A_E{}^{Me}C_EA_E{}^{Me}C_E{}^{Me}C_EA_STTGU_SC_SAC_SAC_STC_SC_S$-- | 4 | 57.44 | 2.61 | 4.81 |
| 38648 | $A_E{}^{Me}C_EA_E{}^{Me}C_E{}^{Me}C_EA_ETTGU_SC_SAC_SAC_STC_SC_S$-- | 4 | 97.68 | 3.28 | 4.36 |
| 38649 | $A_E{}^{Me}C_EA_E{}^{Me}C_E{}^{Me}C_EA_ET_ETGU_SC_SAC_SAC_STC_SC_S$-- | 4 | 46.76 | 2.84 | 4.46 |
| 38650 | $A_E{}^{Me}C_EA_E{}^{Me}C_E{}^{Me}C_EA_ET_ET_EGU_SC_SAC_SAC_STC_SC_S$-- | 4 | 28.16 | 1.51 | 2.03 |
| 38651 | $A_E{}^{Me}C_EA_E{}^{Me}C_E{}^{Me}C_EA_ET_ET_EG_EU_SC_SAC_SAC_STC_SC_S$-- | 4 | 26.12 | 1.26 | 1.46 |
| 38652 | ${}^{Me}C_EA_EA_EA_E{}^{Me}C_EA_EC_SCA_STTGU_SC_SAC_SAC_STC_SC_S$-- | 5 | 31.86 | 1.86 | 4.27 |
| 38659 | $C_SCA_STTGU_SC_SAC_SAC_STC_SC_ST_E$ | 10 | 130.01 | 4.44 | 4.82 |
| 38660 | ${}^{Me}C_EA_EA_EA_E{}^{Me}C_EA_EC_SCA_STTGU_SC_SAC_SAC_STC_SC_ST_E$ | 6 | 17.02 | 3.84 | 4.44 |

As above, these data illustrate that single changes to the placement of a sugar moiety can have a substantial impact on in vivo potency. Further, it is shown that in vitro and in vivo potency are not necessarily correlated. For example, compound 38659 has a low in vitro potency, but is a very potent inhibitor of miR-122 in vivo.

Comparisons of the anti-miR-122 compound structures and in vivo potency revealed an 11 nucleoside core sequence common to a group of active anti-miR-122. This core sequence, where B-D-deoxy sugar moieties and bicyclic sugar moieties are in the same position on the anti-miR-122 nucleotide sequence, is highlighted in Table D-2. The nucleobase sequence of the 11 nucleoside core is complementary to nucleobases 2 to 12 of miR-122 (SEQ ID NO: 1).

TABLE D-2

Potent anti-miR-122 modified oligonucleotides with a common core sequence

| Cmpd # | SEQUENCE (5′ to 3′) and STRUCTURE | | | | | | | | | | | | | | | | | | | | | | |
|---|---|---|---|---|---|---|---|---|---|---|---|---|---|---|---|---|---|---|---|---|---|---|---|
| Position on miR-122 | 22 | 21 | 20 | 19 | 18 | 17 | 16 | 15 | 14 | 13 | 12 | 11 | 10 | 9 | 8 | 7 | 6 | 5 | 4 | 3 | 2 | 1 | SEQ ID NO |
| 38012 | | | | | | | $C_S$ | C | $A_S$ | T | T | G | $U_S$ | $C_S$ | A | $C_S$ | A | $C_S$ | T | $C_S$ | $C_S$ | A | 3 |
| 38016 | | | | | | | ${}^{Me}C_S$ | C | A | $T_S$ | T | G | $T_S$ | ${}^{Me}C_S$ | A | ${}^{Me}C_S$ | A | ${}^{Me}C_S$ | T | ${}^{Me}C_S$ | ${}^{Me}C_S$ | $A_E$ | 3 |
| 38021 | | | | | | | $C_L$ | C | A | $T_L$ | T | G | $T_L$ | $C_L$ | A | $C_L$ | A | $C_L$ | T | $C_L$ | $C_L$ | | 4 |
| 38646 | | | | $A_E$ | ${}^{Me}C_E$ | $A_E$ | ${}^{Me}C_E$ | C | $A_S$ | T | T | G | $U_S$ | $C_S$ | A | $C_S$ | A | $C_S$ | T | $C_S$ | $C_S$ | | 4 |
| 38647 | | | | $A_E$ | ${}^{Me}C_E$ | $A_E$ | ${}^{Me}C_E$ | ${}^{Me}C_E$ | $A_S$ | T | T | G | $U_S$ | $C_S$ | A | $C_S$ | A | $C_S$ | T | $C_S$ | $C_S$ | | 4 |
| 38648 | | | | $A_E$ | ${}^{Me}C_E$ | $A_E$ | ${}^{Me}C_E$ | ${}^{Me}C_E$ | $A_E$ | T | T | G | $U_S$ | $C_S$ | A | $C_S$ | A | $C_S$ | T | $C_S$ | $C_S$ | | 4 |
| 38649 | | | | $A_E$ | ${}^{Me}C_E$ | $A_E$ | ${}^{Me}C_E$ | ${}^{Me}C_E$ | $A_E$ | $T_E$ | T | G | $U_S$ | $C_S$ | A | $C_S$ | A | $C_S$ | T | $C_S$ | $C_S$ | | 4 |
| 38652 | ${}^{Me}C_E$ | $A_E$ | $A_E$ | $A_E$ | ${}^{Me}C_E$ | $A_E$ | $C_S$ | C | $A_S$ | T | T | G | $U_S$ | $C_S$ | A | $C_S$ | A | $C_S$ | T | $C_S$ | $C_S$ | | 5 |
| 38659 | | | | | | | $C_S$ | C | $A_S$ | T | T | G | $U_S$ | $C_S$ | A | $C_S$ | A | $C_S$ | T | $C_S$ | $C_S$ | $T_E$ | 10 |
| 38660 | ${}^{Me}C_E$ | $A_E$ | $A_E$ | $A_E$ | ${}^{Me}C_E$ | $A_E$ | $C_S$ | C | $A_S$ | T | T | G | $U_S$ | $C_S$ | A | $C_S$ | A | $C_S$ | T | $C_S$ | $C_S$ | $T_E$ | 6 |
| 38872 | | | | | | | $C_S$ | C | A | $U_S$ | T | G | $U_S$ | $C_S$ | A | $C_S$ | A | $C_S$ | T | $C_S$ | $C_S$ | A | 3 |
| 38910 | | | | | | | ${}^{Me}C_E$ | $C_S$ | A | $U_S$ | T | G | $U_S$ | $C_S$ | A | $C_S$ | A | $C_S$ | T | $C_S$ | $C_S$ | $A_E$ | 3 |

These data illustrate the discovery of a certain core nucleoside pattern that yields a potent inhibitor of miR-122 in vivo.

HCV Replicon Studies

An HCV replicon assay was used to determine the ability of an anti-miR-122 compound to inhibit the replication of HCV, including parent HCV genotypes and HCV genotypes with mutations that confer resistance to anti-viral agents. Compound 38649 was tested in this assay, to determine its ability to inhibit the replication of HCV sub-genomic replicons of genotype 1a (H77 strain), genotype 1b, and several variants of genotype 1b (A156T, A156S, D168a, and V36M).

For this assay, the cell line used was the cell line ET, a Huh7 human hepatoma cell line that contains a subgenomic replicon of HCV with a stable luciferase reporter and three cell culture-adaptive mutations (luc-ubi-neo/ET). The luciferase reporter is used as an indirect measure of HCV replication. The HCV replicon antiviral evaluation assay examined the effects of the compound at six half-log concentrations of each compound. Human interferon alpha-2b was included as a positive control compound. Sub-confluent cultures of the ET line were plated into 96-well plates and the next day anti-miR-122 compound was transfected into the cells with cationic lipid. Cells were processed 72 hours later when the cells were still sub-confluent. HCV replicon levels were assessed as HCV RNA replicon-derived luciferase activity. The $EC_{50}$ (concentration at which 50% inhibition was observed) was calculated for each HCV genotype, and is shown in Table E. The selectivity index ($SI_{50}$, a ratio of the $EC_{50}$ for viral replication to the $EC_{50}$ for innate cytotoxicity) was also calculated and is shown in Table E.

TABLE E

Anti-Viral Activity of Compound 38649

| HCV Genotype | Antiviral Activity $EC_{50}$ (nM) | Selectivity Index $SI_{50}$ |
|---|---|---|
| HCV Genotype 1b | 57.8 nM | 4.0 |
| HCV Genotype 1b variant V36M | 139.6 nM | >2.0 |
| HCV Mutant A156S | 45.9 nM | 5.7 |
| HCV Mutant A156T | 26.7 nM | 10.0 |
| HCV Mutant D168A | 16.2 nM | 12.0 |
| HCV Genotype 1a (H77 strain) | 14.1 nM | 15.0 |

The results from the replicon assay demonstrate anti-viral activity of compound 38649 against multiple HCV genotypes. The anti-viral activity was sustained for the period of time for which the assay was performed (18 days). The activity of compound 38649 is similarly robust against HCV replicons comprising mutations known to be resistant to certain protease inhibitors prescribed to treat HCV infection.

Single Dose Studies of Anti-miR-122

Compound 38649 was tested in a single dose study in mice, to determine the onset of action, maximal target derepression, and duration of action, at doses ranging from 0.3 mg/kg to 30 mk/kg. An $ED_{50}$ was also calculated from this study.

Anti-miR compound was administered intraperitoneally to groups of 5 mice each, at doses of 0.3, 1.0, 3.0, 10, and 30 mg/kg. For the 0.3 and 1.0 doses, groups of animals were sacrificed at days 3, 7, and 28. For the 3.0, 10 and 30 mg/kg doses, groups of animals were sacrificed at days 3, 5, 7, 14, 21, and 2838649. ALDOA mRNA levels in liver were measured by quantitative PCR, and compared to ALDOA mRNA levels in liver of saline-treated mice, to calculate the fold change in ALDOA expression.

Figure 1B:
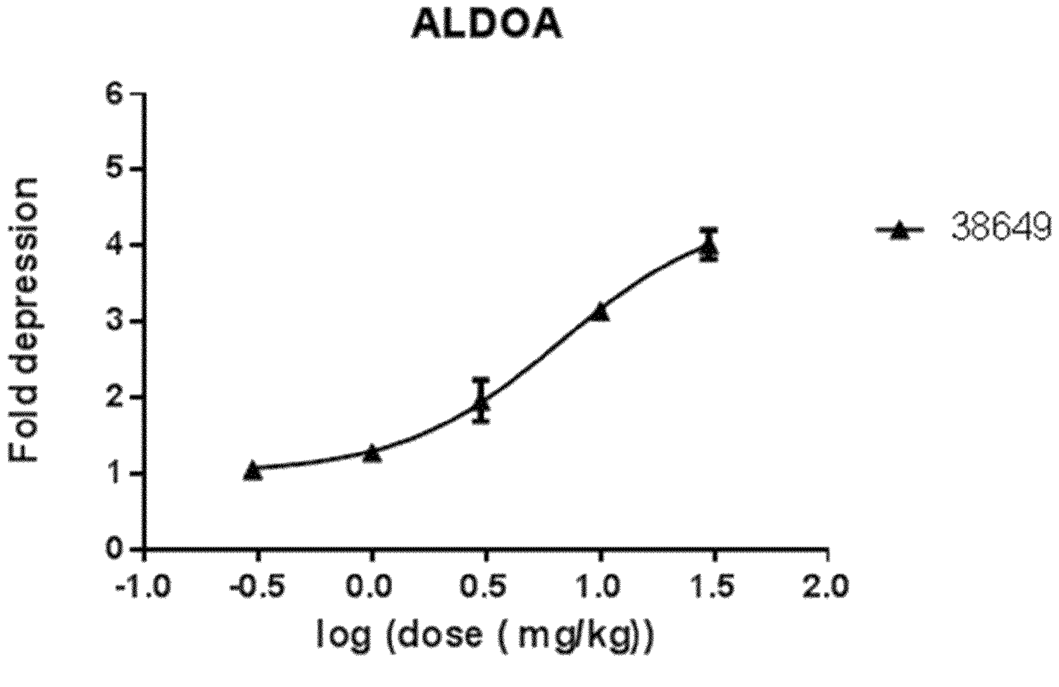

As shown in FIG. 1A, ALDOA derepression was observed as early as day 3 and maintained for more than 28 days after dosing of compound 38649. Maximal target derepression was achieved at 10 mg/kg. An $ED_{50}$ of 6.7 mg/kg was calculated from the day 7 data (FIG. 1B).

Physicochemical Characteristics

Evaluation of physicochemical characteristics may include: measurement of viscosity, to determine whether a solution of the anti-miR is suitable for administration via certain types of parenteral administration, for example subcutaneous administration; calculation of anti-miR half life in liver, to estimate the frequency at which the anti-miR-122 compound could be administered in human subjects; and metabolic stability assay, to identify compounds which may be susceptible to cleavage by nucleases.

Metabolic stability was evaluated by incubating anti-miR-122 compound with non-human primate liver lysate. Nuclease activity in the liver tissue homogenate was confirmed by using reference oligonucleotides, which included a compound with known resistance to nuclease activity, a compound susceptible to 3'-exonuclease activity, and a compound susceptible to endonuclease activity. An internal standard compound was used to control for extraction efficiency. At the 0 hour and 24 hour time points, each sample was subjected to high-performance liquid chromatography time-of-flight mass spectrometry (HPLC-TOF MS) to measure oligonucleotide lengths and amounts. The percentage loss is determined by comparing the amount of full-length compound at the 0 hour and 24 hour time points. Compounds 38646, 38647, 38648, 38649, 38650, 38651, 38652, 38659, and 38660 exhibited a percentage loss of 10% or less at the 24 hour time point. Compound 38012 exhibited a percentage loss of approximately 50% at the 24 hour time point.

An additional single dose study was performed in mice, to estimate the half-life of compound 38649. The half-life in liver was estimated to be at least two weeks.

Safety

To assess various safety parameters, an in vivo study in rodents was performed for certain of the compounds described herein, to evaluate the potential the compounds to trigger a pro-inflammatory response. Parameters assessed included changes in organ weights, such as spleen weight and liver weight, and the expression of interferon-inducible genes, such as IFIT and OASL, in the liver. Serum chemistries were also evaluated. Additionally, for certain compounds, safety parameters were evaluated in non-human primates and included hematological endpoints, serum chemistry, organ weights, coagulation, complement activation, cytokine/chemokine changes, and pro-inflammatory gene expression.

While the tested compounds exhibited some variability amongst the safety parameters evaluated, several of the compounds, including compound 38649, were found to have particularly suitable safety profiles.

Example 2

Conjugated Anti-miR-122 Modified Oligonucleotides

Anti-miR-122 modified oligonucleotides were conjugated to a GalNAc-containing moiety, to determine whether the conjugation would improve the potency of the oligonucleotides.

Figure 2:
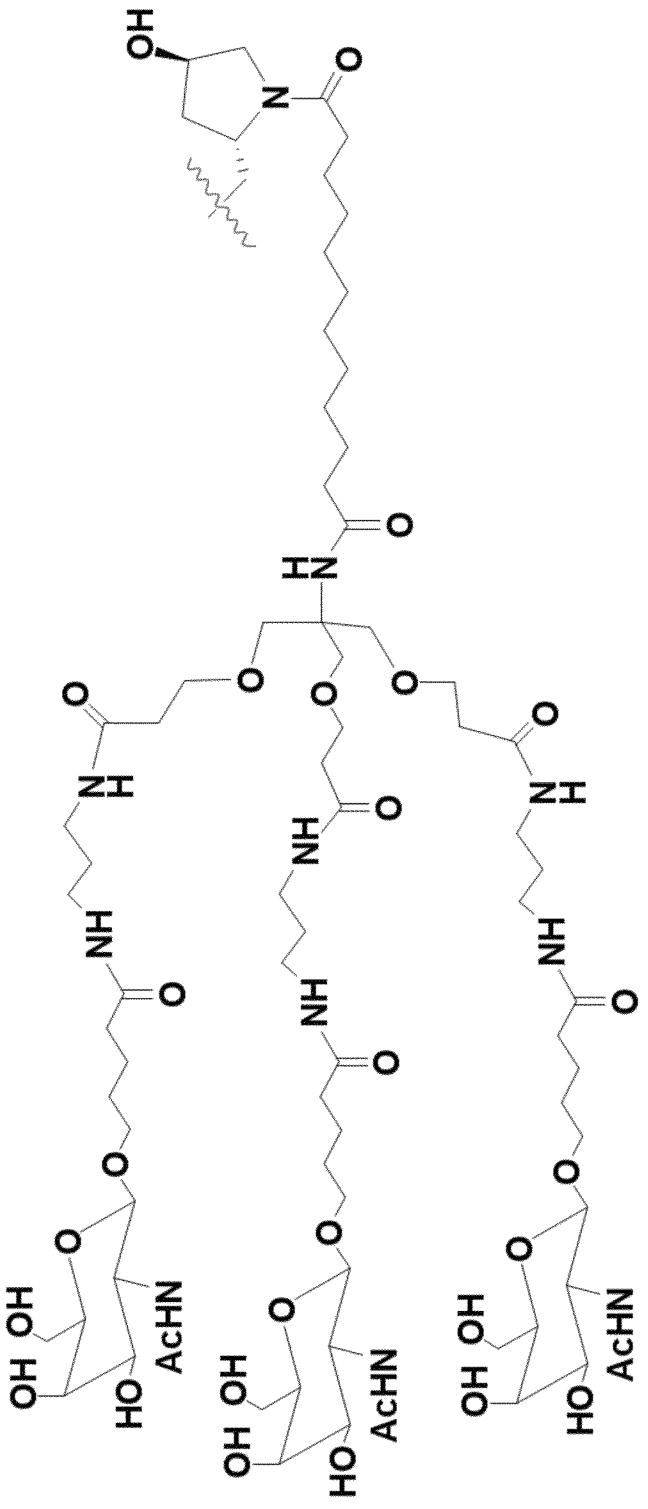
FIG. 2. Structure of a conjugate moiety comprising three GalNAc ligands.

GalNAc-containing compounds were formed by conjugating the structure in FIG. 2 to the 3' end of the 38649 modified oligonucleotide. The linkage between the GalNAc-containing moiety and the 3'-end of 38649 varied, as shown in Table F-1. For example, in compound 38368, the GalNAc-containing moiety is linked directly to the 3'-terminal nucleoside of 38649 through a phosphodiester linkage, as shown in FIG. 3C, where X is a phosphodiester linkage and MO is compound 38649. In compound 38458, the GalNAc-containing moiety is linked to the 3'-terminal nucleoside of 38649 through a β-D-deoxynucleoside, with a phosphorothioate linkage between the 3'-terminal nucleoside of 38649 and a phosphodiester linkage between the β-D-deoxynucleoside and the GalNAc-containing moiety, as shown in FIG. 3A, where $X_2$ is a phosphorothioate linkage, m is 1, $N_m$ is a β-D-deoxynucleoside, $X_1$ is a phosphodiester linkage, and MO is compound 38649.

TABLE F-1

GalNAc-containing compounds

| Compound # | Compound structure |
|---|---|
| 38368 | Structure III of FIG. 3C, where X is a phosphodiester linkage and MO is compound 38649 |
| 38371 | Structure III of FIG. 3C, where X is a phosphorothioate linkage and MO is compound 38649 |
| 38458 | Structure I of FIG. 3A, where $X_2$ is a phophorothioate linkage, m is 1, $N_m$ is a β-D-deoxynucleoside, $X_1$ is a phosphodiester linkage, and MO is compound 38649 |
| 38459 | Structure I of FIG. 3A, where $X_2$ is a phophodiester linkage, m is 1, $N_m$ is a β-D-deoxynucleoside (dA), $X_1$ is a phosphodiester linkage, and MO is compound 38649 |
| 38597 | Structure I of FIG. 3A, where $X_2$ is a phosphothioate linkage, m is 1, $N_m$ is a 2'-O-methoxyethyl nucleoside, $X_1$ is a phosphodiester linkage, and MO is compound 38649 |
| 38598 | Structure I of FIG. 3A, where $X_2$ is a phophorothioate linkage, m is 1, $N_m$ is a $X_1$ is a phosphodiester linkage, and MO is compound 38649 |

The GalNAc-conjugated modified oligonucleotides were assessed for in vivo potency, release of unconjugated modified oligonucleotide from the GalNAc-conjugated modified oligonucleotide, and liver and tissue concentration.

Potency studies were conducted according to the protocol used to evaluate the unconjugated modified oligonucleotides, described above. Compound was injected into mice, and in vivo potency was assessed at day 7 by measuring the de-repression of ALDOA. The dosages of conjugated compounds indicate the dosage of modified oligonucleotide administered.

Figure 4A:
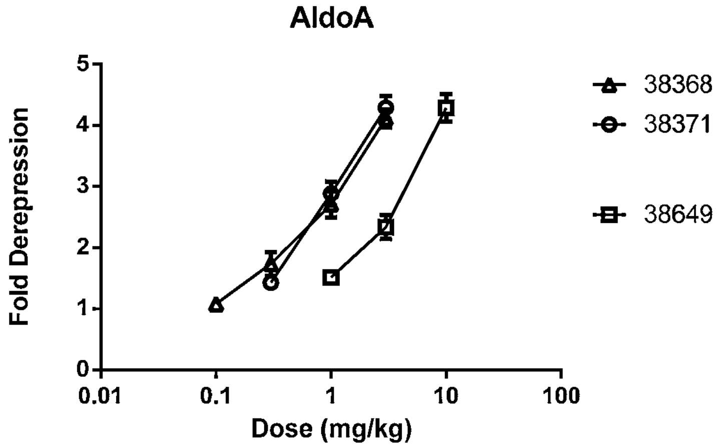
FIGS. 4A, 4B, and 4C. In vivo potency of GalNAc-conjugated anti-miR-122 modified oligonucleotides.
Figure 4B:
Figure 4C:
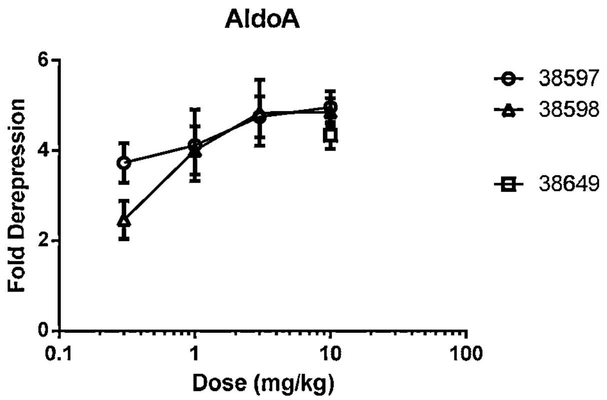

As shown in FIG. 4, each of the three GalNAc-conjugated modified oligonucleotides tested was more potent than the unconjugated modified oligonucleotide. Compounds 38368 and 38371 exhibited an increase in potency of approximately 3-fold, relative to unconjugated 38649 (FIG. 4A). Compounds 38458 and 38459, each of which has a β-D-deoxyribonucleoside linking group, exhibited at least a 10-fold increase in potency (FIG. 4B). Compounds 38597 and 38598, each of which has a 2'-sugar modified linking group, also exhibited at least a 10-fold increase in potency (FIG. 4C). In additional studies, potency increases of up to 20-fold have been observed for compounds 38459, 38458, 38597, and 38598.

An additional experiment was conducted to include a wider range of doses of compound 38459. Compound 38459 (n=6) or compound 38649 (n=3) was administered to mice, and ALDOA levels in liver and cholesterol levels in blood were measured seven days later. Average ALDOA and cholesterol levels were calculated and are shown in Table F-2. As shown in Table F-2, a single, subcutaneous dose of compound 38459 exhibited increased potency relative to unconjugated compound 38649, with respect to increasing ALDOA levels and lowering cholesterol levels. In this experiment, the calculated $ED_{50}$ for compound 38459 was 0.19 mg/kg, and the calculated $ED_{50}$ for compound 38649 was 3.5 mg/kg (an 18-fold difference in potency).

TABLE F-2

Increased potency of conjugated anti-miR-122 compound

| Compound | Dose | ALDOA Fold change | Cholesterol mg/dL |
|---|---|---|---|
| 38649 (unconjugated) | 1.0 mg/kg | 1.2 | 100.2 |
| | 3.0 mg/kg | 2.2 | 81.2 |
| | 10 mg/kg | 3.3 | 73.4 |
| 38459 (GalNAc-conjugated) | 0.03 mg/kg | 1.1 | 95.4 |
| | 0.1 mg/kg | 1.7 | 84.4 |
| | 0.3 mg/kg | 2.8 | 74 |
| | 1 mg/kg | 3.5 | 59.2 |
| | 3 mg/kg | 3.8 | 61.8 |
| | 10 mg/kg | 3.8 | 61.4 |

Also measured was the amount of unconjugated modified oligonucleotide in the liver and kidney tissue 7 days following a single subcutaneous dose of compounds 38368 and 38371 at doses of 1 mg/kg and 3 mg/kg, and compounds 38458 and 38459 at doses of 0.3 mg/kg, 1 mg/kg, and 3 mg/kg. Each sample was subjected to high-performance liquid chromatography time-of-flight mass spectrometry (HPLC-TOF MS) to measure oligonucleotide lengths and amounts. The lower limit of quantitation (LLOQ) by this method is 0.2-1.0 μg/g.

The GalNAc-conjugated modified oligonucleotides were found to have varying rates of formation of unconjugated modified oligonucleotide. For example, following administration of compound 38368, less than 10% of compound 38649 (an unconjugated modified oligonucleotide) is detected in the liver. Following administration of compound 38371, compound 38649 was not detected in the liver at either dose of compound 38371. Conversely, seven days following subcutaneous administration of compound 38459, the only unconjugated modified oligonucleotide species detected was unconjugated 38649; the parent compound 38459 was not detected. Following administration of compound 38458, unconjugated modified oligonucleotide was detected in two forms: 38649, as well as 38649-PO-A (a metabolite of compound 38458). This metabolite was detected at higher levels than unconjugated 38649.

Also measured was the amount of unconjugated modified oligonucleotide in the liver 24 hours following a single subcutaneous dose of compounds 38458 and 38459 at doses of 0.3 mg/kg, 1 mg/kg, and 3 mg/kg. Anti-miR levels were measured by LC-TOF. The lower limit of quantitation (LLOQ) by this method is 0.2-1.0 μg/g. It was observed that following administration of compound 38459, 90% of the total compound present in the liver was unconjugated compound 38649. Following administration of 38458, approximately 46% of total compound present in the liver was unconjugated compound 38649. Thus, unconjugated compound 38649 is released more rapidly from compound 38459 than from compound 38458. These data suggest that the metabolism of the conjugated compound is influenced by the attachment between the linker and the modified oligonucleotide.

Oligonucleotides generally accumulate to the highest levels in kidney tissue, followed by liver tissue. To determine whether the GalNAc conjugate altered the accumulation of compound in liver tissue compared to kidney tissue, relative to unconjugated compound, the amount of unconjugated 38649 was also measured in the kidney tissue. As described above, following administration of compound 38459, 100% of the total compound found in the liver is unconjuated 38649, indicating complete release of 38649 from the GalNAc-conjugated compound 38459. Following administration of compound 38459, compound 38649 accumulated less in the kidney compared to the liver, (i.e. exhibited a lower kidney:liver ratio), relative to accumulation of compound 38649 following administration of compound 38649. Thus, compound 38459 can preferentially deliver compound 38649 to the liver, while minimizing delivery to the kidney, as compared to unconjugated 38649.

The onset and duration of action for compound 38459 was evaluated in an in vivo study. Groups of mice were given a single, subcutaneous (SC) dose of compound 38459 at 0.1 mg/kg, 0.3 mg/kg, 1 mg/kg, and 3 mg/kg. An additional group of mice was administered compound 38649 at a dose of 10 mg/kg. A group of animals from each treatment was sacrificed on each of days 1, 2, 3, 4, 5, 6, 14, 21, 28, and 56. RNA was isolated from liver and ALDOA mRNA levels were measured by real-time PCR. The mean ALDOA level for each group was calculated. The fold change relative to the control group (PBS-treated) is shown in Table G.

TABLE G

Onset and duration of action of compound 38459

| Days following single SC dose | Fold change in ALDOA 38459 3 mg/kg | 38459 1 mg/kg | 38459 0.3 mg/kg | 38459 0.1 mg/kg | 38649 10 mg/kg |
|---|---|---|---|---|---|
| 1 | 4.9 | 3.6 | 1.7 | 1.4 | 2.2 |
| 2 | 4.2 | 3.2 | 2.4 | 1.4 | 4.7 |
| 3 | 4.4 | 4.6 | 3.5 | 1.6 | 3.4 |
| 4 | 5.1 | 4.9 | 3.3 | 2.2 | 4.6 |
| 5 | 5.9 | 4.9 | 3.9 | 2.1 | 4.5 |
| 6 | 5.1 | 4.5 | 3.2 | 2.2 | 3.6 |
| 14 | 4.8 | 4.3 | 3.4 | 1.7 | 3.1 |
| 21 | 5.9 | 4.9 | 4.0 | 2.2 | 3.6 |
| 28 | 4.8 | 4.7 | 2.9 | 2.0 | 4.2 |
| 56 | 5.6 | 4.6 | 2.6 | 1.7 | 3.2 |

The data in Table G demonstrate that compound 38459, as well as compound 38649, has a rapid onset of action, as evidenced by ALDOA derepression as early as 1 day following a single dose of compound. Further, ALDOA derepression is maintained for at least 8 weeks following a single dose of compound.

These data demonstrate that the GalNAc-conjugated compound 38459, which is at least 10-fold more potent than the unconjugated 38649 compound, achieves this potency at significantly lower liver tissue concentrations, with preferential delivery to the liver tissue. Additionally, compound 38459 exhibits a rapid onset of action, and a duration of action of at least 8 weeks.

Also tested were LNA-containing unconjugated and conjugated modified oligonucleotides, shown in Table H.

TABLE H

LNA-containing compounds

| Compound # | Sequence (5' to 3') and Modifications | Structure | SEQ ID NO |
|---|---|---|---|
| 36848 | $C_LCA_LTTG_LT_LCAC_L$ $AC_LTC_LC_L$, | Unconjugated | 7 |
| 36852 | $C_LCA_LTTG_LT_LCAC_L$ $AC_LTC_LC_L$ | Conjugated as in Structure III of Figure 3C, where X is PO and MO is 36848 | 7 |
| 36632 | $C_LCA_LTTG_LT_LCAC_L$ $AC_LTC_LC_L$ | Conjugated as in Structure I of Figure 3A, where $X_2$ is a phophodiester linkage, m is 1, $N_m$ is a β-D-deoxynucleoside (dA), $X_1$ is a phosphodiester linkage, and MO is compound 36848 | 7 |

Sugar and linkage moieties are indicated as follows: where nucleosides not followed by a subscript indicate β-D-deoxyribonucleosides; nucleosides followed by a subscript "L" indicate LNA nucleosides; and each internucleoside linkage is a phosphorothioate internucleoside linkage.

Compounds 36848 and 36852 were tested for in vivo potency according to the same protocol as described above, to evaluate the ability of the compounds to inhibit miR-122 activity and increase ALDOA expression. While each compound was a potent inhibitor of miR-122, the GalNAc-conjugated compound 36852 exhibited greater potency than unconjugated compound 36848 (approximately 3-fold greater).

Compound 36632 was also tested for in vivo potency in a single dose administration study, following a similar protocol as described above, at doses of 0.03 mg/kg, 0.1 mg/kg, 0.3 mg/kg, 1.0 mg/kg, 3.0 mg/kg, and 10.0 mg/kg. Compound 36632 demonstrated fold increases in ALDOA expression of 1.6, 2.7, 3.7, 4.3, 4.7, 6.0, respectively, relative to PBS-treated control. Compound 36848, at doses of 1.0 mg/kg, 3.0 mg/kg, and 10 mg/kg resulted in fold increases in ALDOA expression of 1.6, 2.5, and 5.3, respectively. A comparison of compound 36632 to compound 36848 revealed an increase in potency of approximately 30-fold for the conjugated compound, relative to the unconjugated compound.

Example 3

Mouse Model of HCV Infection

Due to host-pathogen specificity, HCV can only infect humans and chimpanzees. As such, smaller species, such as mice, that are typically used for experimental in vivo studies cannot be infected with HCV for testing of candidate agents for the treatment of HCV infection. To address this problem, human liver chimeric mouse models may be utilized (see, e.g., Bissig et al., *Proc Natl Acad Sci USA,* 2007, 104:20507-20511; Bissig et al., *J Clin Invest.,* 2010, 120: 924-930). In this model, the livers of immunodeficient mice are repopulated with human hepatocytes, resulting in a chimeric liver in which most of the hepatocytes are human hepatocytes. The mice are then infected with HCV and treated with anti-HCV agents. This mouse model is commercially available from, for example, PhoenixBio.

Anti-miR-122 compounds are tested in mice with human chimeric livers that have been infected with HCV. Groups of animals (n=5-10) receive one or more doses of anti-miR-122 compound, e.g., at a dose identified from the treatment regimen study. For pharmacokinetic analyses and measurement of HCV RNA levels, plasma is collected at various time-points. Liver tissue is collected when the study is terminated.

In some embodiments, inhibition of miR-122 is confirmed by measuring human ALDOA mRNA levels. It is expected that administration of an anti-miR-122 compound reduces HCV RNA levels in the serum of the mouse.

Example 4

HCV RNA Level Reduction in Response to miR-122 Inhibition

A human chimeric mouse liver model was used to evaluate the effects of miR-122 inhibition on miR-122 target gene expression and HCV viral titer.

Human Chimeric Liver Mice

The effects of miR-122 inhibition on target gene expression were evaluated in human chimeric liver mice without HCV infection. Groups of mice (n=6) were treated with a single dose of PBS, 0.3 mg/kg, 1.0 mg/kg, 3.0 mg/kg, or 10 mg/kg of compound 38459. Seven days following treatment, the study was terminated and liver tissue was collected for measurement of ALDOA expression and compound tissue concentration. ALDOA mRNA levels were increased relative to ALDOA mRNA levels in PBS-treated mice, however the derepression of ALDOA expression was 3-fold to 5-fold less than that observed in wild-type mice. Compound 38459 levels were approximately 3-fold lower in chimeric liver mice, relative to concentrations in wild-type mice. These observations are consistent with the reduced expression of the asialoglycoprotein receptor (ASGPR) in the human chimeric liver mice, relative to wild-type mice. As the accumulation of compound in the liver cell is dependent upon uptake by the ASGPR, a reduced expression of ASGPR would be expected to result in reduced accumulation of GalNAc-conjugated modified oligonucleotide, and consequently reduced sensitivity to the ability of compound 38459 to de-repress endogenous targets of miR-122, such as ALDOA. Accordingly, the human chimeric liver mouse model may underpredict the activity of compound 38459 in a subject where ASGPR expression is maintained. Preliminary data suggest that ASGPR expression is maintained at similar levels in livers of HCV-infected patients relative to livers of non-HCV infected subjects.

Treatment of HCV-Infected Human Chimeric Liver Mice

Anti-miR-122 compounds were tested in a human chimeric liver mouse model of HCV infection. The livers of immunodeficient mice were repopulated with human hepatocytes, resulting in a chimeric liver in which most of the hepatocytes are human hepatocytes. Approximately 3.5 weeks following inoculation with HCV genotype 1a, mice with an HCV RNA level of $>1\times10^6$ copies/ml were selected for inclusion in this study (Day −7).

For a single week study, a group of 3 animals was treated with a single 10 mg/kg dose of 38459 on Day 0. Blood was collected on Day −7, 0, 3, and 7. The study was terminated on day 7, when in addition to blood, liver tissue and kidney tissue were collected. In this study, HCV RNA levels were reduced at Days 3 and 7.

Figure 5A:
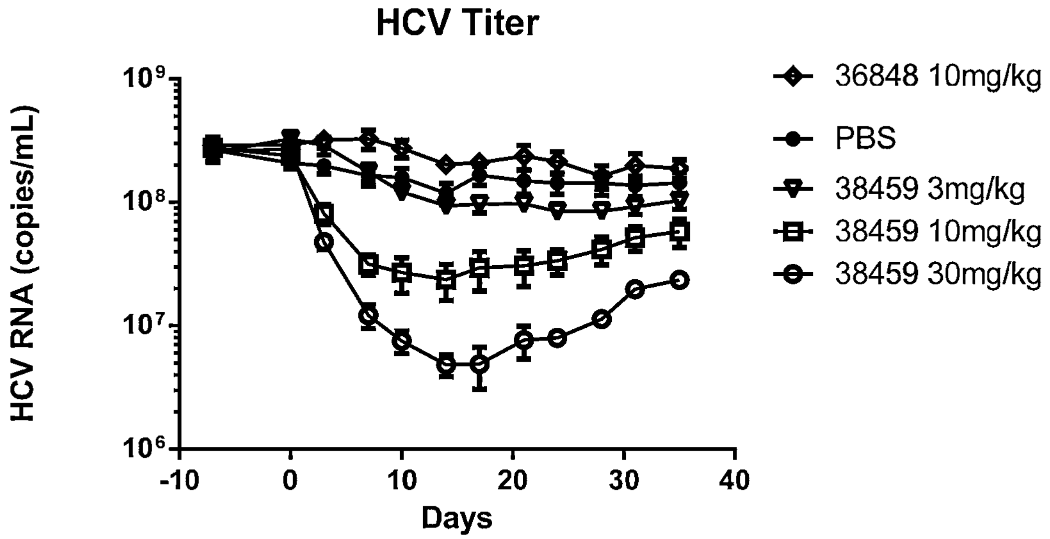
FIGS. 5A and 5B. Antisense inhibition of miR-122 reduces HCV titer.

For a multiple week study, groups of 5 animals each were treated as follows: PBS (n=5); 3 mg/kg 38459 (n=5); 10 mg/kg 38459 (n=4-5); or 30 mg/kg 38459 (n=4-5). An additional group of animals was treated with 10 mg/kg unconjugated compound 36848 (n=5). Treatment was administered as a single, subcutaneous injection on Day 0. Blood was collected on Days −7, 0, 3, 7, 10, 14, 17, 21, 24, 28, and 35. HCV RNA levels in blood were measured by real-time PCR according to routine methods, and are shown in Table I. Unless otherwise indicated, each treatment group contained 5 animals. As shown in Table I, HCV RNA levels were significantly reduced as early as Day 3 in the groups treated with 10 mg/kg or 30 mg/kg of compound 38459, which reduction was sustained through at least Day 35. Statistical significance was calculated by 2way ANOVA analysis of mean HCV RNA levels in compound-treated animals, normalized to mean HCV RNA levels in PBS-treated animals. In this study, unconjugated compound 36848 did not reduce HCV RNA levels. These results are also illustrated in graphic form in FIG. 5A.

TABLE I

GalNAc-conjugated anti-miR-122 reduces HCV titer

| Day | PBS Average | 36848 10 mg/kg | 38459 3 mg/kg | 38459 10 mg/kg | 38459 30 mg/kg |
|---|---|---|---|---|---|
| −7 | 2.66E+08 | 2.90E+08 | 2.54E+08 | 2.76E+08 | 2.60E+08 |
| 0 | 2.08E+08 | 2.92E+08 | 3.26E+08 | 2.38E+08 | 2.70E+08 |
| 3 | 1.97E+08 | 3.20E+08 | 2.90E+08 | 8.10E+07* | 4.76E+07**** |
| 7 | 1.65E+08 | 3.26E+08 | 1.76E+08 | 3.16E+07**** | 1.22E+07**** |
| 10 | 1.59E+08 | 2.74E+08 | 1.21E+08 | 2.70E+07**** | 7.52E+06**** |
| 14 | 1.19E+08 | 2.02E+08 | 9.34E+07 | 2.37E+07**** | 4.82E+06**** |
| 17 | 1.67E+08 | 2.10E+08 | 9.68E+07 | 2.94E+07**** | 4.89E+06**** |
| 21 | 1.49E+08 | 2.36E+08 | 9.72E+07 | 3.06E+07**** | 7.65E+06**** (n = 4) |
| 24 | 1.43E+08 | 2.14E+08 | 8.46E+07 | 3.35E+07**** | 7.95E+06**** (n = 4) |
| 28 | 1.43E+08 | 1.63E+08 | 8.48E+07 | 4.16E+07*** | 1.13E+07**** (n = 4) |
| 31 | 1.37E+08 | 1.99E+08 | 9.22E+07 | 5.18E+07* (n = 4) | 1.98E+07**** (n = 4) |
| 35 | 1.44E+08 | 1.88E+08 | 1.03E+08 | 5.80E+07* (n = 4) | 2.35E+07**** (n = 4) |

****p < .0001;

***p < 0.0005;

*p < 0.05

These results demonstrate that, following a single administration of GalNAc-conjugated modified oligonucleotide 38459, HCV viral titer was significantly reduced in HCV-infected animals, with an early onset and sustained duration of action.

Figure 5B:
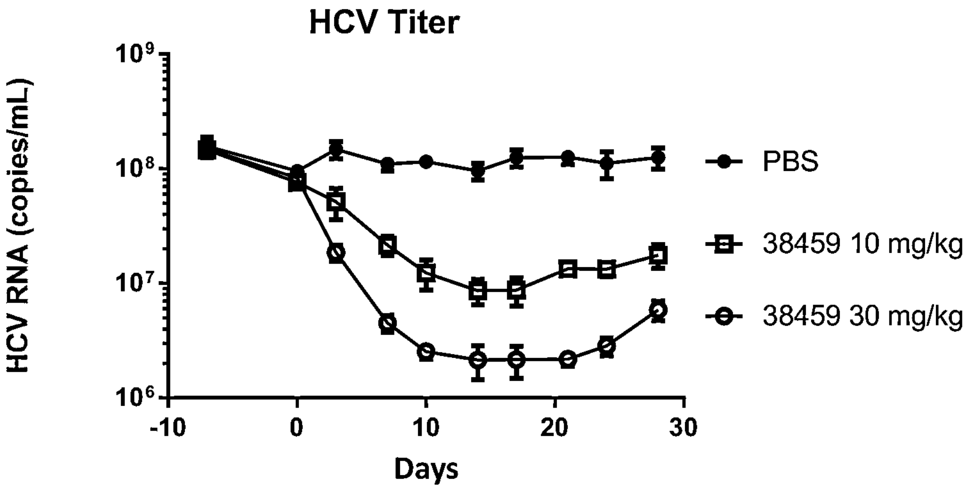
Figure 6A:
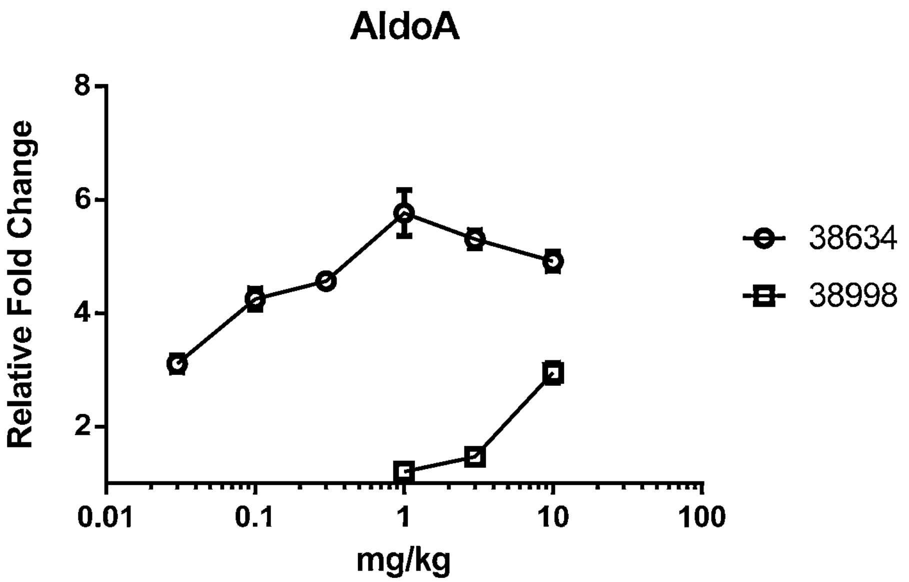
FIGS. 6A and 6B. In vivo potency of GalNAc-conjugated anti-miR-122 modified oligonucleotides.
Figure 6B:
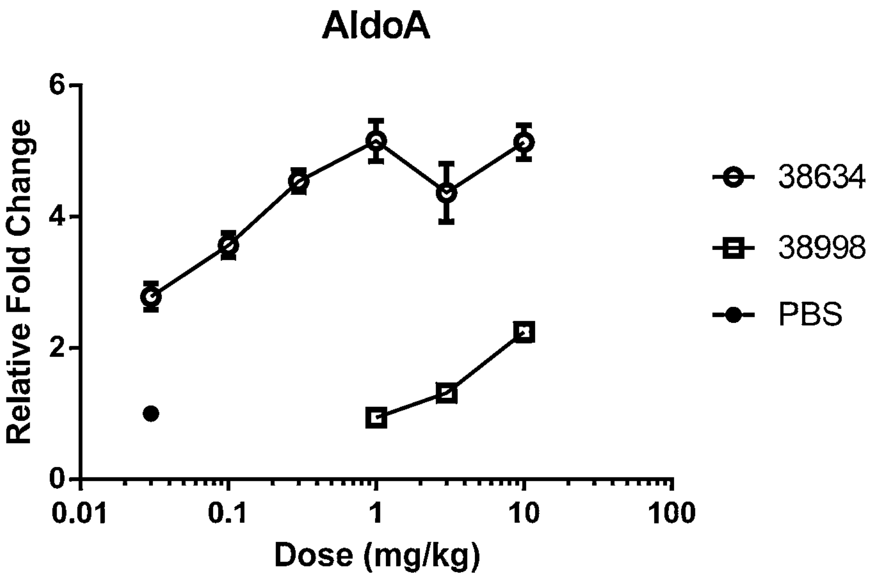
Figure 7A:
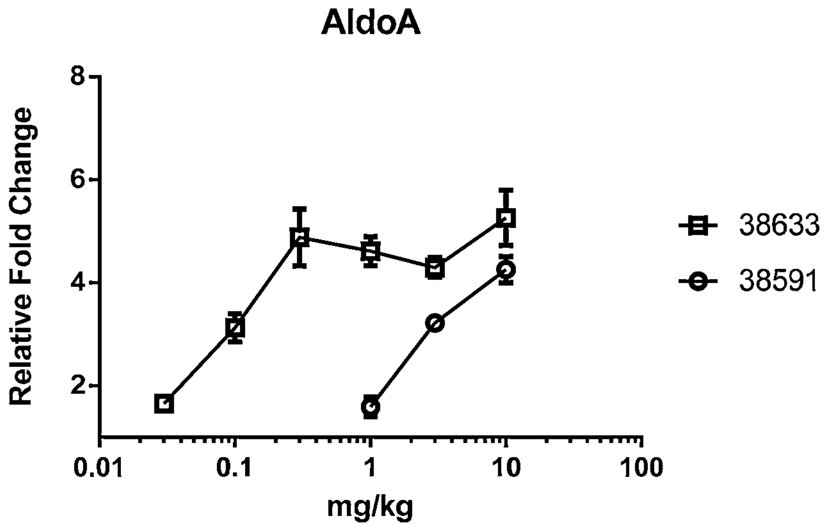
FIGS. 7A and 7B. In vivo potency of GalNAc-conjugated anti-miR-122 modified oligonucleotides.
Figure 7B:
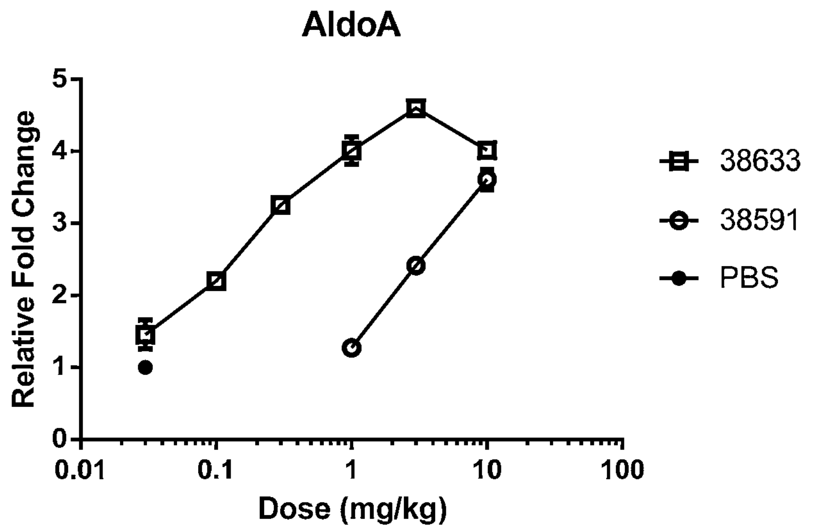

An additional study was performed to evaluate the effects of compound 38459 in the human chimeric liver mouse model of HCV infection, where the mice are infected with HCV genotype 3a. Groups of 5 animals each were treated as follows: PBS (n=4); 10 mg/kg 38459 (n=5); or 30 mg/kg 38459 (n=5). Mice were inoculated with HCV genotype 3a. Seven days prior to treatment, blood was collected from mice for measurement of viral titer. Treatment was administered as a single, subcutaneous injection on Day 0. Blood was collected on Days 0, 3, 7, 10, 14, 17, 21, 24, and 28 following treatment. HCV RNA levels in blood were measured by real-time PCR according to routine methods. As shown in FIG. 5B, HCV RNA levels were significantly reduced early as Day 3 in the groups treated with 10 mg/kg or 30 mg/kg of compound 38459, and this reduction was sustained through at least Day 28.

Also observed was a substantial reduction in steatosis in the livers of the mice treated with compound 38459. The reduced steatosis was observed in mice infected with HCV, and in uninfected mice, suggesting that inhibition of miR-122 can reduce steatosis both in the presence and absence of HCV infection.

Example 5

Conjugated Shorter Modified Oligonucleotides

GalNAc-containing compounds were formed by conjugating a structure in FIG. 3 to the 3' end of the modified oligonucleotides shown in Table J. Sugar moieties, internucleoside linkages, and nucleobases are indicated as follows: nucleosides not followed by a subscript are β-D-deoxyribonucleosides; nucleosides followed by a subscript "S" are S-cEt nucleosides; and each internucleoside linkage is a phosphorothioate internucleoside linkage.

TABLE J

Unconjugated and Conjugated Modified Oligonucleotides

| | Sequence and Modifications | Structure | SEQ ID NO |
|---|---|---|---|
| 38591 | $U_STGU_SC_SAC_SAC_STC_SC_SA_S$ | Unconjugated | 8 |
| 38633 | $U_STGU_SC_SAC_SAC_STC_SC_SA_S$ | Structure I of Figure 3A, where $X_2$ is a phophodiester linkage, m is 1, $N_m$ is a β-D-deoxynucleoside (dA), $X_1$ is a phosphodiester linkage | 8 |
| 38998 | $C_SA_SC_SA_SC_SU_SC_SC_S$ | Unconjugated | 9 |
| 38634 | $C_SA_SC_SA_SC_SU_SC_SC_S$ | Structure I of Figure 3A, where $X_2$ is a phophodiester linkage, m is 1, $N_m$ is a β-D- deoxynucleoside (dA), $X_1$ is a phosphodiester linkage | 9 |

To determine in vivo potency, the compounds were evaluated for their ability to de-repress the expression of liver aldolase A (ALDOA). Compounds were administered to mice, and ALDOA mRNA levels were measured, by quantitative PCR, in RNA isolated from liver. The fold change in ALDOA mRNA, relative to saline, was calculated to determine in vivo potency (FIGS. 6A and 6B and 7A and 7B). The ED50 (concentration of compound at which ALDOA derepression is 50% of maximum) and ED90 (concentration of compound at which ALDOA derepression is 90% of maximum) calculated from the results of those experiments are shown in Table K and L.

TABLE K

In vivo potency of conjugated and unconjugated anti-miR-122 compounds

| Compound | ED50 (mg/kg) | Fold change | ED90 (mg/kg) | Fold change |
|---|---|---|---|---|
| Experiment 1 (FIG. 6A) | | | | |
| 38634 | 0.03 | 456 | 0.3 | 212 |
| 38998 | 13.7 | | 63.8 | |
| Experiment 2 (FIG. 6B) | | | | |
| 38634 | 0.04 | 290 | 0.43 | 99.3 |
| 38998 | 11.6 | | 42.7 | |

TABLE L

In vivo potency of conjugated and unconjugated anti-miR-122 compounds

| Compound | ED50 (mg/kg) | Fold change | ED90 (mg/kg) | Fold change |
|---|---|---|---|---|
| Experiment 1 (FIG. 7A) | | | | |
| 38633 | 0.08 | 27 | 0.25 | 26 |
| 38591 | 2.2 | | 6.62 | |
| Experiment 2 (FIG. 7B) | | | | |
| 38633 | 0.15 | 20 | 0.94 | 10 |
| 38591 | 3.0 | | 8.9 | |

As shown in Table K, GalNAc conjugation according to the present invention improved the $ED_{50}$ and $ED_{90}$ of an 8-mer anti-miR-122 compound by at least 100-fold. As shown in Table L, GalNAc conjugation according to the present invention improved the $ED_{50}$ and $ED_{90}$ of a 13-mer anti-miR-122 compound by at least 10-fold.

Derepression of another miR-122 target gene, CD320, was also determined for compounds 38634 and 38998. The results were similar to the results obtained for ALDOA shown in Table K: GalNAc conjugation according to the present invention improved the $ED_{50}$ by 343-fold and 272-fold in experiments 1 and 2, respectively, and improved the $ED_{90}$ by 492-fold and 545-fold in experiments 1 and 2, respectively.

Figure 8A:
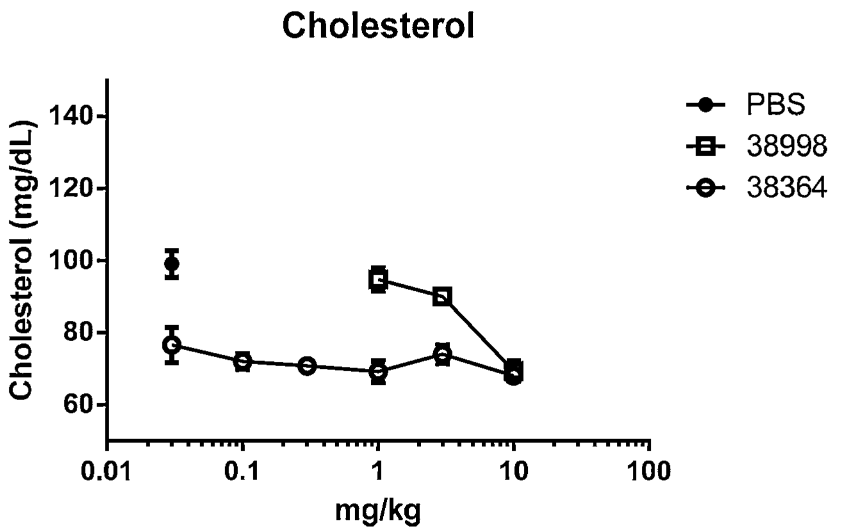
FIGS. 8A and 8B. In vivo potency of GalNAc-conjugated anti-miR-122 modified oligonucleotides.
Figure 8B:
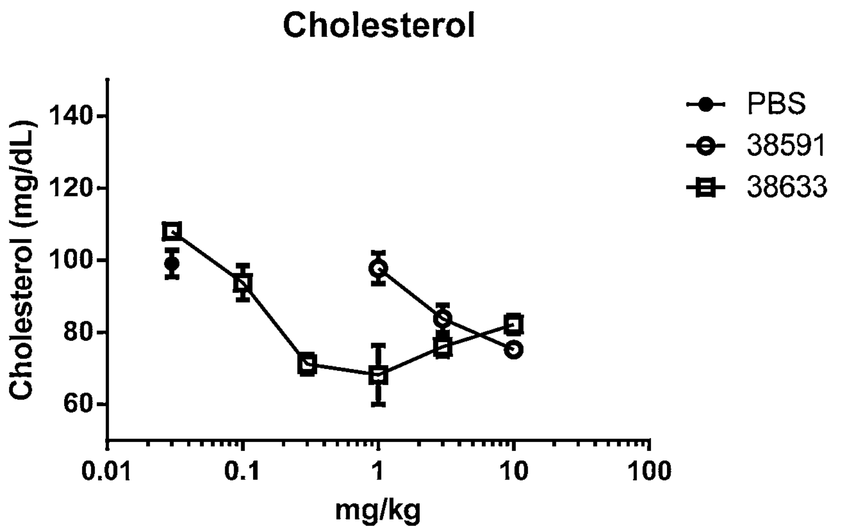

GalNAc conjugation described herein also improved cholesterol-lowering potency was also observed for the compounds comprising GalNAc. Exemplary results from experiment 1 are shown in FIGS. 8A and 8B. Compounds 38633 and 38634, which are GalNAc conjugates, were more potent than compounds 38591 and 38998, which lack GalNAc. Similar results were obtained for experiment 2 (data not shown).

Example 6

Pharmacodynamic Activity of Anti-miR-122 Compounds in Non-Human Primates

Anti-miR-122 compounds were tested in normal non-human primates (cynomolgus monkeys). A single dose of GalNAc-conjugated compound 38459 or unconjugated compound 38649 was administered subcutaneously (n=3 for each compound). PBS was administered as a control treatment (n=5). On day 4 and day 8 following administration of compound, liver tissue was collected, and RNA was isolated for measurement of ALDOA levels. Total cholesterol in blood was measured on day 8. As shown in Table L, ALDOA derepression is observed at day 4 and day 8, at each dose of compound 38459, including the lowest dose of 1 mg/kg. Cholesterol lowering was also observed with the lowest dose of compound 38459. Thus, GalNAc-conjugated compound 38459 is significantly more potent in non-human primates, relative to unconjugated compound 38649. Additionally, both compounds have a duration of action of at least one week following a single dose in non-human primates.

TABLE L

Inhibition of miR-122 in non-human primates

| Treatment | ALDOA (Day 4) fold change | ALDOA (Day 8) fold change | Cholesterol (Day 8) mg/dL |
|---|---|---|---|
| PBS | 1.0 | | 95.3 |
| 38649, 100 mg/kg | 3.4 | 4.0 | 67.0 |
| 38459, 1 mg/kg | 5.0 | 3.9 | 64.3 |
| 38459, 10 mg/kg | 3.0 | 3.6 | 66.7 |
| 38459, 100 mg/kg | 4.0 | 4.1 | 65.3 |

Example 7

Pharmacokinetic Activity of Conjugated Anti-miR-122 Compounds

The plasma and tissue pharmacokinetics of anti-miR-122 compounds were evaluated in mice and non-human primates.

A single, subcutaneous dose of compound 38649 or GalNAc-conjugated compound 38459 was administered to CD-1 mice. Blood was collected a multiple time points over a 24 hour period following administration, and the total amount of compound in the blood was measured by hybridization-based ELISA.

A single, subcutaneous dose of compound 38649 or GalNAc-conjugated compound 38459 was administered to non-human primates. Blood was collected at multiple time points over a 24 hour period following administration, and the total amount of compound in the blood was measured by LC-MS.

Figure 9A:
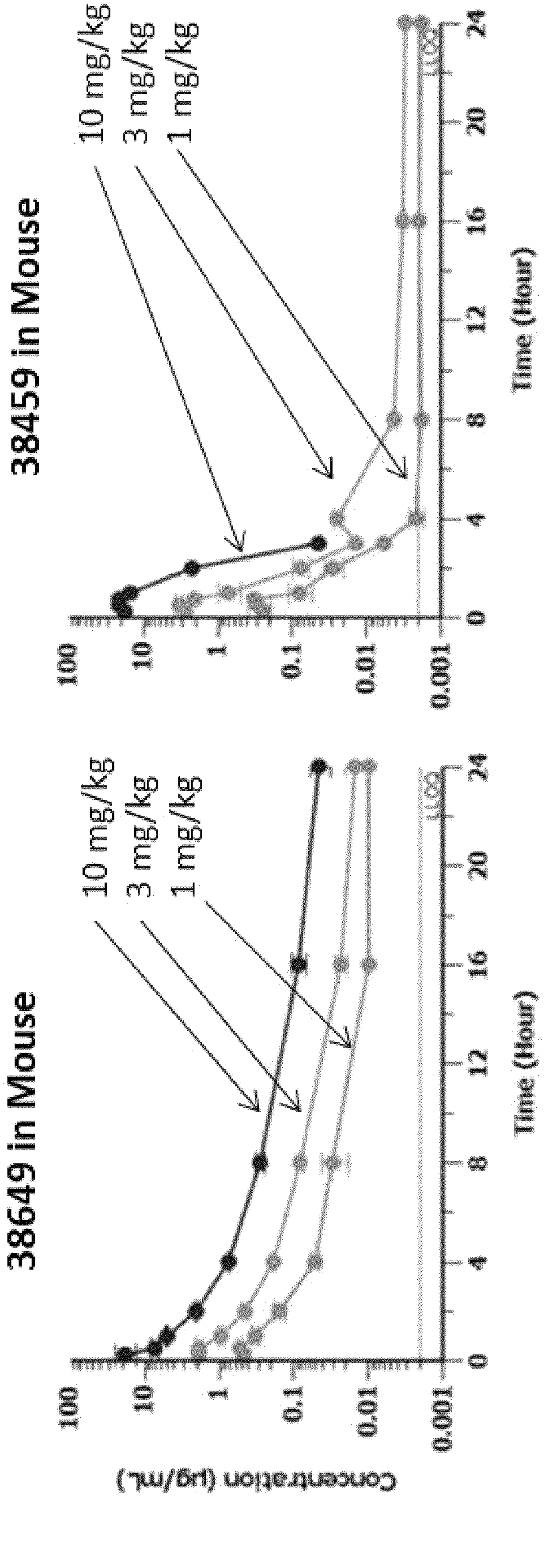
FIGS. 9A and 9B. Pharmacokinetics of anti-miR-122 compounds.
Figure 9B:
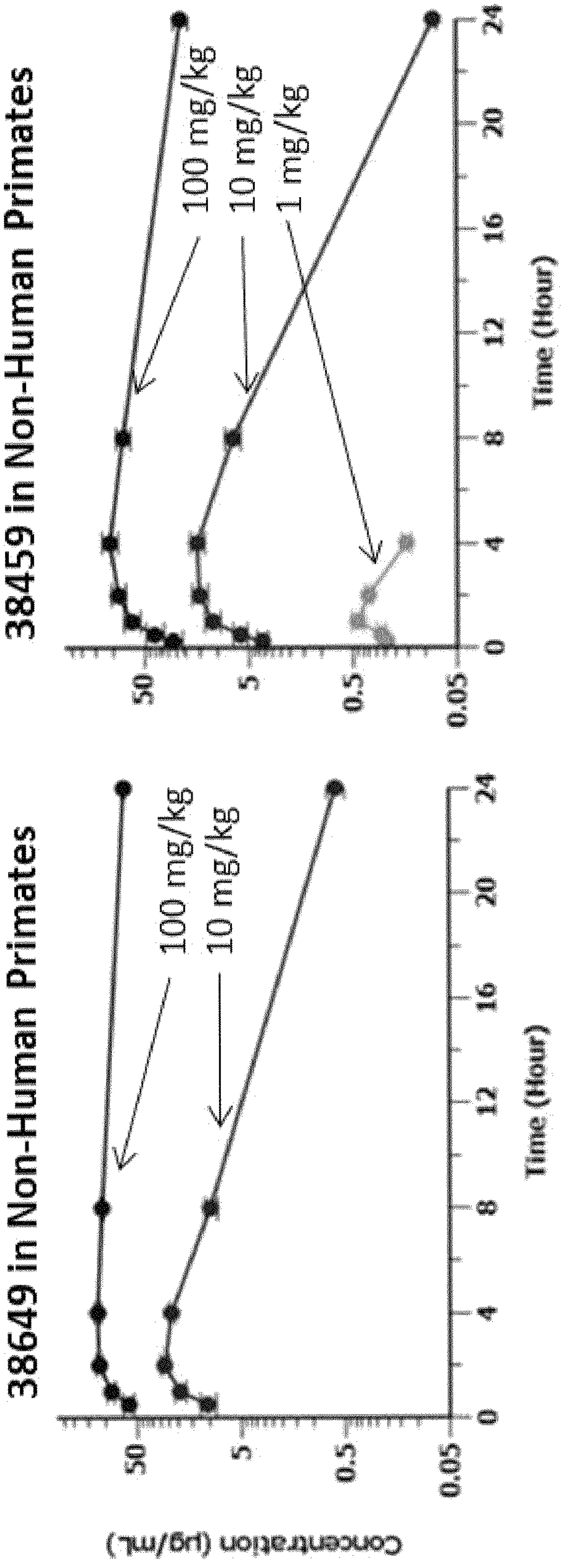

As shown in FIG. 9, in mouse (FIG. 9A) and non-human primates (FIG. 9B), GalNAc-conjugated compound 38459 is cleared more rapidly from plasma, compared to unconjugated compound 38649. Following administration of GalNAc-conjugated compound 38459, unconjugated compound 38649 is not detected, indicating that conjugated compound 38459 is not metabolized in the blood (data not shown)

In this study, tissue levels of compounds were also measured in the liver and kidney of mice (Table M) and non-human primates (Table N).

TABLE M

Compound tissue levels in mice 24 hours after single dose

| | | Compound Administered: | | | | | |
|---|---|---|---|---|---|---|---|
| | | 38459 (+GalNAc) | | | 38649 | | |
| | | Tissue: | | | | | |
| Dose | Compound detected | Kidney Mean (μg/g) | Liver Mean (μg/g) | K/L Ratio | Kidney Mean (μg/g) | Liver Mean (μg/g) | K/L Ratio |
| 1 mg/kg | 38649 | 1.1 | 5.7 | 0.19 | 18.4 | 4 | 4.6 |
| | Total compound | 1.1 | 7.4 | 0.15 | | | |
| 3 mg/kg | 38649 | 8.2 | 15.8 | 0.52 | 83.9 | 10.8 | 7.6 |
| | Total compound | 16.8 | 27.7 | 0.61 | | | |

TABLE N

Compound tissue levels in non-human primates 72 hours after single dose

| | | Compound Administered: | | | | | |
|---|---|---|---|---|---|---|---|
| | | 38459 (+GalNAc) | | | 38649 | | |
| | | Tissue: | | | | | |
| Dose | Compound detected | Kidney Mean (μg/g) | Liver Mean (μg/g) | K/L Ratio | Kidney Mean (μg/g) | Liver Mean (μg/g) | K/L Ratio |
| 1 mg/kg | 38649 | 5.6 | 27.2 | 0.21 | | | |
| | Total compound | 31.3 | 34 | 0.92 | | | |
| 10 mg/kg | 38649 | 124 | 148 | 0.84 | 283.3 | 61.2 | 4.6 |
| | Total compound | 513.5 | 186.3 | 2.7 | | | |
| 100 mg/kg | 38649 | 374.1 | 418.8 | 0.89 | 1430 | 242.3 | 5.9 |
| | Total compound | 2129.1 | 547.2 | 3.9 | | | |

Following administration, compound 38459 is rapidly metabolized to unconjugated compound 38649 in liver and kidney. Additionally, consistent with the data from the mouse study described above, the kidney to liver ratio of compound 38459 is significantly lower than that of compound 38649.

Based on the concentration of compound in the liver 24 hours following administration, it was estimated that approximately 6 μg/g of GalNAc-conjugated compound 38459 and approximately 30 μg/g of unconjugated compound 38459 results in 90% maximal potency at day 7 (as measured by ALDOA derepression). Thus, compound 38459 results in greater potency at a lower liver tissue concentration, relative to unconjugated compound 38649.

These data demonstrate that in non-human primates and mice, conjugation to a GalNAc-containing moiety results in significantly enhanced delivery of modified oligonucleotide to the liver. Further, a low $ED_{50}$ coupled with a lower kidney to liver ratio suggests that GalNAc-conjugated compound 38459 may have a high therapeutic index.

Example 8

Toxicology and Safety Studies of Anti-miR-122 Compounds

Multiple studies were conducted in mice, rodents and non-human primates, to evaluate the safety and tolerability of GalNAc-conjugated compound 38459.

For example, compound 38459 was evaluated in a pro-inflammatory study in rats. Male Sprague Dawley rats were administered a single, subcutaneous dose of compound 38459. At day 14 following administration, expression of ALDOA and CXCL13 (an interferon-inducible gene) was measured in liver.

As shown in Table O, no increase in CXCL13 expression was detected at a dose as high as 100 mg/kg, while ALDOA levels were elevated starting at the 1 mg/kg dose. A known inflammatory anti-miR-122 compound was also tested, and resulted in increases of CXCL13 levels of 2- to 2.5-fold at the 10, 30 and 100 mg/kg doses.

TABLE O

Compound 38459 does not increase pro-inflammatory gene expression

| Dose of compound 38459 | ALDOA Fold-change | CXCL13 Fold-change |
|---|---|---|
| 0.1 mg/kg | 1.2 | 1.4 |
| 0.3 mg/kg | 1.6 | 1.6 |
| 1 mg/kg | 2.5 | 1.5 |
| 3 mg/kg | 2.9 | 0.8 |
| 10 mg/kg | 2.8 | 0.6 |
| 30 mg/kg | 3.2 | 0.8 |
| 100 mg/kg | 3.4 | 0.7 |

Additional toxicology studies were conducted in mice and non-human primates (cynomolgus monkeys), and no significant adverse effects were observed at therapeutically relevant doses.

Example 9

Conjugated Shorter Modified Oligonucleotides

Cholesterol-containing compounds were formed by conjugating cholesterol to the 3' end of the modified oligonucleotides shown in Table P. Sugar moieties, internucleoside linkages, and nucleobases are indicated as follows: nucleosides not followed by a subscript are β-D-deoxyribonucleosides; nucleosides followed by a subscript "S" are S-cEt nucleosides; and each internucleoside linkage is a phosphorothioate internucleoside linkage, except the internucleoside linkages indicated by subscript (0), which are phosphodiester linkages.

TABLE P

Unconjugated and Conjugated Modified Oligonucleotides

| | Sequence and Modifications | Structure | SEQ ID NO |
|---|---|---|---|
| 38998 | $C_SA_SC_SA_SC_SU_SC_SC_S$ | Unconjugated | 9 |
| 38070 | $C_SA_SC_SA_SC_SU_SC_SC_S$ | 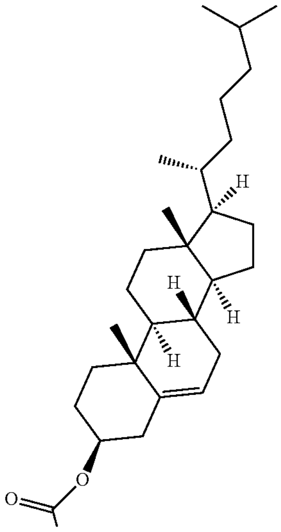 | 9 |

TABLE P-continued

| Unconjugated and Conjugated Modified Oligonucleotides | | |
|---|---|---|
| Sequence and Modifications | Structure | SEQ ID NO |
| | 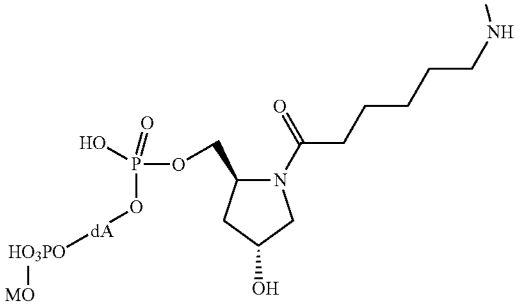 MO is $C_SA_SC_SA_SC_SU_SC_SC_S$ | |

To determine in vivo potency, the compounds were evaluated for their ability to de-repress the expression of liver aldolase A (ALDOA). Compounds were administered to mice, and ALDOA mRNA levels were measured, by quantitative PCR, in RNA isolated from liver. The fold change in ALDOA mRNA, relative to saline, was calculated to determine in vivo potency. The ED50 (concentration of compound at which ALDOA derepression is 50% of maximum) and ED90 (concentration of compound at which ALDOA depression is 90% of maximum) calculated from the results of those experiments are shown in Table Q.

TABLE Q

In vivo potency of conjugated and unconjugated anti-miR-122 compounds

| Compound | ED50 (mg/kg) | Fold change | ED90 (mg/kg) | Fold change |
|---|---|---|---|---|
| 38070 | 0.08 | 78.8 | 1.27 | 31.6 |
| 38998 | 6.3 | | 40.1 | |

As shown in Table Q, cholesterol conjugation according to the present invention improved the $ED_{50}$ and $ED_{90}$ of an 8-mer anti-miR-122 compound by at least 30-fold.

Derepression of another miR-122 target gene, CD320, was also determined for compounds 38070 and 38998. The results were similar to the results obtained for ALDOA (data not shown).

Cholesterol conjugation described herein also improved cholesterol-lowering potency. At most concentrations tested, compound 38070 reduced cholesterol to a greater extent than the same concentration of compound 38998 (data not shown).

Various modifications of the invention, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, GENBANK® accession numbers, and the like) cited in the present application is specifically incorporated herein by reference in its entirety.

What is claimed is:

1. A compound comprising a modified oligonucleotide having the structure:

$A_E{}^{Me}C_EA_E{}^{Me}C_E{}^{Me}C_EA_ET_ETGU_SC_SAC_SAC_STC_SC_S$ (SEQ ID NO: 4)

wherein the superscript "Me" indicates 5-methylcytosine; nucleosides not followed by a subscript are β-D-deoxyribonucleosides; nucleosides followed by a subscript "E" are 2'-MOE nucleosides; nucleosides followed by a subscript "S" are S-cEt nucleosides; and each internucleoside linkage is a phosphorothioate internucleoside linkage.

2. The compound of claim 1, wherein the compound comprises a conjugate moiety linked to the 5' terminus or the 3' terminus of the modified oligonucleotide.

3. The compound of claim 2, wherein the conjugate moiety comprises at least one ligand selected from a carbohydrate, cholesterol, a lipid, a phospholipid, an antibody, a lipoprotein, a hormone, a peptide, a vitamin, a steroid, and a cationic lipid.

4. The compound of claim 2, wherein the compound has the structure:

$L_n$-linker-MO wherein each L is, independently, a ligand and n is from 1 to 10; and MO is the modified oligonucleotide.

5. The compound of claim 2, wherein the compound has the structure:

$L_n$-linker-X-MO wherein each L is, independently, a ligand and n is from 1 to 10; X is a phosphodiester linkage or a phosphorothioate linkage; and MO is the modified oligonucleotide.

6. The compound of claim 2, wherein the compound has the structure:

$L_n$-linker-$X_1$-$N_m$-$X_2$-MO wherein each L is, independently, a ligand and n is from 1 to 10; each N in $N_m$ is, independently, a modified or unmodified nucleoside and m is from 1 to 5; $X_1$ and $X_2$ are each, independently, a phosphodiester linkage or a phosphorothioate linkage; and MO is the modified oligonucleotide.

7. The compound of claim 6, wherein the compound has the structure:

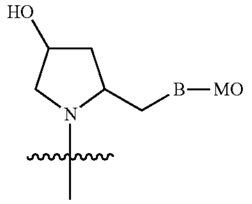

wherein:

B is selected from —O—, —S—, —N($R^N$)—, —Z—P(Z')(Z")O—, —Z—P(Z')(Z")O—$N_m$—X—, and —Z—P(Z')(Z")O—$N_m$—Y—;

MO is the modified oligonucleotide;

$R^N$ is selected from H, methyl, ethyl, propyl, isopropyl, butyl, and benzyl;

Z, Z', and Z" are each independently selected from O and S;

each N in $N_m$ is, independently, a modified or unmodified nucleoside;

m is from 1 to 5;

X is selected from a phosphodiester linkage and a phosphorothioate linkage;

Y is a phosphodiester linkage; and the wavy line indicates the connection to the rest of the linker and ligand(s).

8. The compound of claim 6 wherein n is from 1 to 5.

9. The compound of claim 6, wherein at least one ligand is a carbohydrate.

10. The compound of claim 6, wherein at least one ligand is selected from mannose, glucose, galactose, ribose, arabinose, fructose, fucose, xylose, D-mannose, L-mannose, D-galactose, L-galactose, D-glucose, L-glucose, D-ribose, L-ribose, D-arabinose, L-arabinose, D-fructose, L-fructose, D-fucose, L-fucose, D-xylose, L-xylose, alpha-D-mannofuranose, beta-D-mannofuranose, alpha-D-mannopyranose, beta-D-mannopyranose, alpha-D-glucofuranose, Beta-D-glucofuranose, alpha-D-glucopyranose, beta-D-glucopyranose, alpha-D-galactofuranose, beta-D-galactofuranose, alpha-D-galactopyranose, beta-D-galactopyranose, alpha-D-ribofuranose, beta-D-ribofuranose, alpha-D-ribopyranose, beta-D-ribopyranose, alpha-D-fructofuranose, alpha-D-fructopyranose, glucosamine, galactosamine, sialic acid, and N-acetylgalactosamine.

11. The compound of claim 6, wherein each ligand is N-acetylgalactosamine.

12. The compound of claim 6, wherein the compound has the structure:

(I)

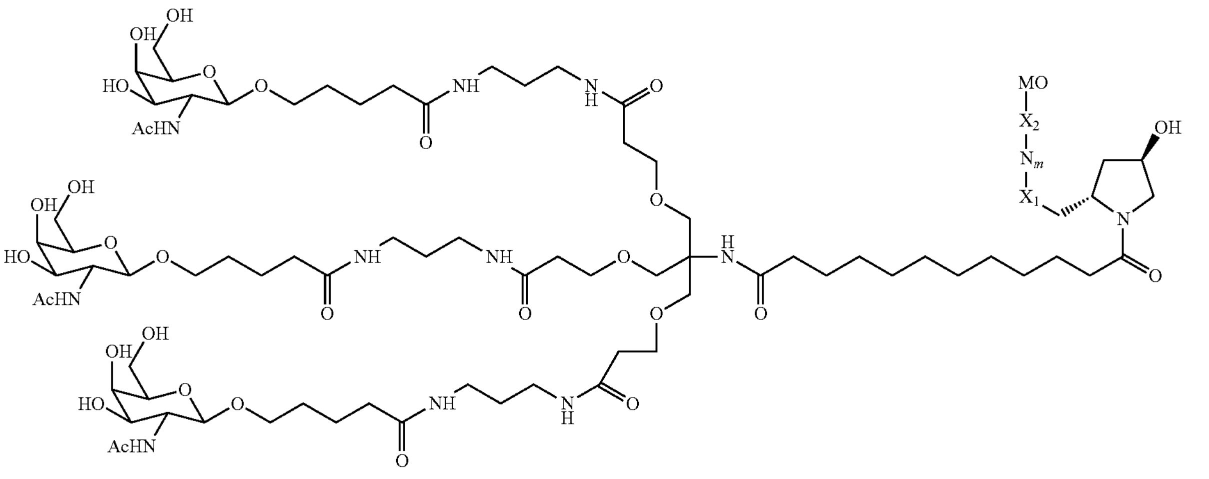

wherein each N in $N_m$ is, independently, a modified or unmodified nucleoside and m is from 1 to 5; $X_1$ and $X_2$ are each, independently, a phosphodiester linkage or a phosphorothioate linkage; and MO is the modified oligonucleotide.

13. The compound of claim 12, wherein at least one of $X_1$ and $X_2$ is a phosphodiester linkage.

14. The compound of claim 6, wherein $N_m$ is $N'_pN''$, wherein each N' is, independently, a modified or unmodified nucleoside and p is from 0 to 4; and N'' is a nucleoside comprising an unmodified sugar moiety.

15. The compound of claim 14, wherein each N' comprises an unmodified sugar moiety.

16. The compound of claim 14, wherein N'' is a β-D-deoxyriboadenosine or a β-D-deoxyriboguanosine.

17. The compound of claim 6, wherein the sugar moiety of each N in $N_m$ is independently selected from a β-D-ribose, a β-D-deoxyribose, a 2'-O-methoxy sugar, a 2'-O-methyl sugar, a 2'-fluoro sugar, and a bicyclic sugar moiety.

18. A conjugate having the structure wherein X is a phosphodiester linkage; m is 1; N in $N_m$ is a β-D-deoxyriboadenosine; Y is a phosphodiester linkage; and MO is a modified oligonucleotide having the structure $A_E{}^{Me}C_EA_E{}^{Me}C_E{}^{Me}C_EA_ET_ETGU_SC_S AC_STC_SC_S$ (SEQ ID NO: 4), wherein the superscript "Me" indicates 5-methylcytosine, wherein nucleosides not followed by a subscript are β-D-deoxyribonucleosides, nucleosides followed by a subscript "E" are 2'-MOE nucleosides, nucleosides followed by a subscript "S" are S-cEt nucleosides, and each internucleoside linkage is a phosphorothioate internucleoside linkage; and wherein Y is linked to the 3' terminus of the modified oligonucleotide.

19. A pharmaceutical composition comprising a conjugate having the structure:

(II)

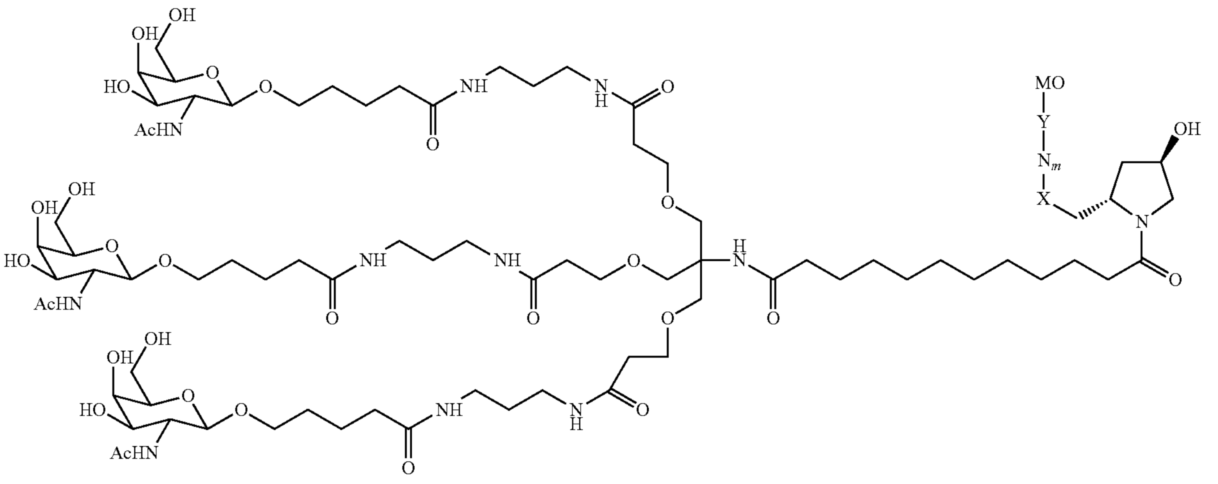

(II)

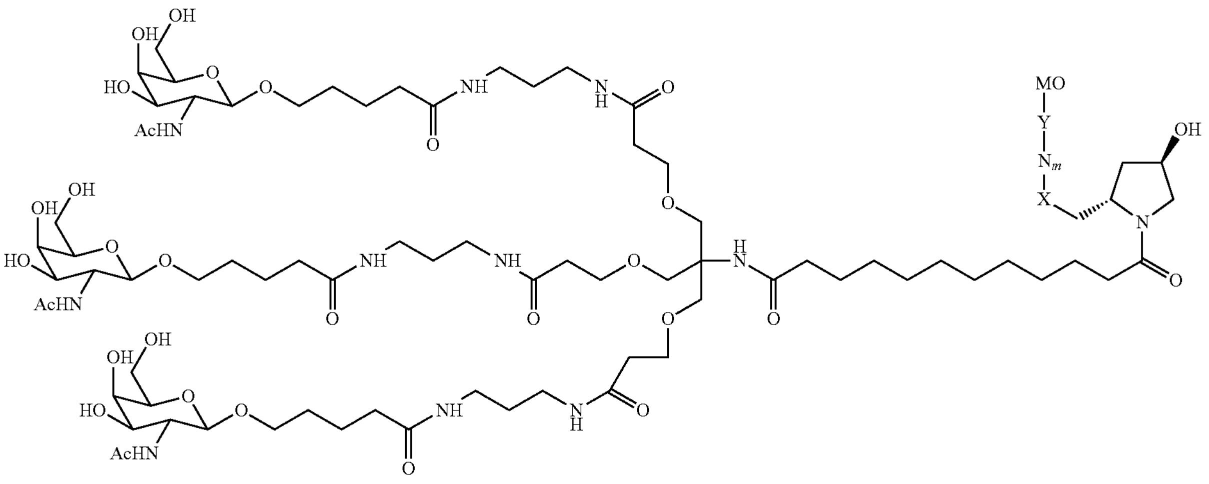

wherein X is a phosphodiester linkage; m is 1; N in $N_m$ is a β-D-deoxyriboadenosine; Y is a phosphodiester linkage; and MO is a modified oligonucleotide having the structure $A_E{}^{Me}C_EA_E{}^{Me}C_E{}^{Me}C_EA_ET_ETGU_SC_SAC_SAC_STC_SC_S$ (SEQ ID NO: 4), wherein the superscript "Me" indicates 5-methylcytosine, wherein nucleosides not followed by a subscript are β-D-deoxyribonucleosides, nucleosides followed by a subscript "E" are 2'-MOE nucleosides, nucleosides followed by a subscript "S" are S-cEt nucleosides, and each internucleoside linkage is a phosphorothioate internucleoside linkage; and wherein Y is linked to the 3' terminus of the modified oligonucleotide;

and one or more pharmaceutically acceptable excipients.

20. The pharmaceutical composition of claim 19, which is a sterile aqueous solution.

* * * * *